(12) United States Patent
Tew et al.

(10) Patent No.: US 10,493,159 B2
(45) Date of Patent: Dec. 3, 2019

(54) PROTEIN TRANSDUCTION DOMAINS MIMICS

(71) Applicant: University of Massachusetts, Boston, MA (US)

(72) Inventors: Gregory N. Tew, Amherst, MA (US); Gregory J. Gabriel, Marietta, GA (US); Abhigyan Som, Sunderland, MA (US); Arife Ozgul Tezgel, Amherst, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/168,787

(22) Filed: Oct. 23, 2018

(65) Prior Publication Data

US 2019/0091337 A1    Mar. 28, 2019

Related U.S. Application Data

(63) Continuation of application No. 15/682,738, filed on Aug. 22, 2017, now Pat. No. 10,143,753, which is a continuation of application No. 15/175,643, filed on Jun. 7, 2016, now Pat. No. 9,770,511, which is a continuation of application No. 13/703,645, filed as application No. PCT/US2011/041906 on Jun. 24, 2011, now Pat. No. 9,382,366.

(60) Provisional application No. 61/358,533, filed on Jun. 25, 2010.

(51) Int. Cl.
| | |
|---|---|
| A61K 9/00 | (2006.01) |
| A61K 47/32 | (2006.01) |
| C08G 61/08 | (2006.01) |
| C08G 61/12 | (2006.01) |
| C08F 234/02 | (2006.01) |
| G01N 33/58 | (2006.01) |
| G01N 33/60 | (2006.01) |

(52) U.S. Cl.
CPC ............ *A61K 47/32* (2013.01); *C08F 234/02* (2013.01); *C08G 61/08* (2013.01); *C08G 61/12* (2013.01); *G01N 33/582* (2013.01); *G01N 33/588* (2013.01); *G01N 33/60* (2013.01); *C08G 2261/126* (2013.01); *C08G 2261/143* (2013.01); *C08G 2261/1426* (2013.01); *C08G 2261/3324* (2013.01); *C08G 2261/3342* (2013.01); *C08G 2261/418* (2013.01)

(58) Field of Classification Search
CPC ..................................................... A61K 47/32
See application file for complete search history.

*Primary Examiner* — Paul W Dickinson
(74) *Attorney, Agent, or Firm* — Milstein Zhang & Wu LLC

(57) ABSTRACT

The invention generally relates to synthetic mimics of cell penetrating peptides. More particularly, the invention relates to certain novel monomers, oligomers and polymers (e.g., co-polymers) that are useful for the preparation of synthetic mimics of cell penetrating peptides, their compositions, preparations and use.

13 Claims, 47 Drawing Sheets

PROTEIN TRANSDUCTION DOMAINS MIMICS

PRIORITY CLAIMS AND RELATED APPLICATIONS

This application claims the benefit of priority to and is a continuation of U.S. Ser. No. 15/682,738, filed Aug. 22, 2017, which claims the benefit of priority to and is a continuation of U.S. Ser. No. 15/175,643, filed Jun. 7, 2016, which claims the benefit of priority to and is a continuation of U.S. Ser. No. 13/703,645, filed Jun. 26, 2013, which is the U.S. National Phase application of and claims the benefit of priority to international application PCT/US2011/041906, filed Jun. 24, 2011, which claims the benefit of priority from U.S. Provisional Application Ser. No. 61/358,533, filed Jun. 25, 2010, each of which is incorporated herein by reference in its entirety.

TECHNICAL FIELD OF THE INVENTION

The invention generally relates to synthetic mimics of protein transduction domains. More particularly, the invention relates to certain novel monomers, oligomers and polymers (including co-polymers) that are useful for the preparation of synthetic mimics of protein transduction domains, related compositions and methods of preparation and use.

BACKGROUND OF THE INVENTION

Protein transduction domains (PTDs), also known as cell penetrating peptides (CPPs), are oligo- or poly-cationic peptides that can facilitate cellular uptake of many different cargos such as small molecules, proteins, DNA/RNA and nanoparticles.

In 1988, Frankel and Pabo, and Green and Lowestein independently reported that TAT protein from HIV is able to cross cellular membranes and localize inside cells. (Frankel, et al. 1988 Cell 55, 1189-1193; Green, et al. 1988 Cell 55, 1179-1188.) Since then, protein transduction domains have been under intense study for two major reasons. First, it is well known that the plasma membrane limits the transport of highly charged molecules. The fact that PTDs, with multiple cationic centers, readily transverse the membrane is important for a fundamental understanding of membrane transport. Second, the ability of PTDs to deliver cargo (proteins, antibodies, and nucleic acids) into mammalian cells offers possibilities for both new therapies and new tools to study cell biology. (Fonseca, et al. 2009 Adv. Drug. Deliv. Rev. 61, 953-964; Gump, et al. 2007 TRENDS Mol Med 13, 443-448; Sebbage, 2009 Bioscience Horizons 2, 64-72.)

PTDs primarily consist of cationic amino acid sequences such as arginines and/or lysines. Early studies showed that the translocation abilities of PTDs were directly associated with the presence of arginine residues. (Schwarze, et al. 2000 Trends Pharmacol Sci 21, 45-48; Futaki, et al. 2003 J. Mol. Recog. 16, 260-264; Fischer, et al. 2000 J. Peptide Res. 55, 163-172; Mitchell, et al. 2000 J. Peptide Res. 56, 318-325; Futaki, et al. 2001 J. Biol. Chem. 276, 5836-5840; Wender, et al. 2000 Proc. Natl. Acad. Sci. USA 97, 13003-13008.) For example, in the case of $TAT_{49-57}$ (RKKRRQRRR), replacement of the arginine amino acids with alanine or other cationic residues (lysine, histidine, and orthonine), led to reduced cellular uptake. In contrast, substitution of all non-arginine residues with arginine (i.e. Arg-replacement) resulted in enhanced internalization efficiency (e.g., R9 was reported to be 20-fold more efficient than $TAT_{49-57}$). In addition to arginine content, the peptide length sets another parameter for cellular uptake. It was reported that there is an optimum length for maximum activity. (Rothbard, et al. 2002 J. Med. Chem. 45, 3612-3618.)

Although the number of known PTDs has increased significantly and small molecule synthetic analogues have been attempted, design and synthesis of simple structures that capture the biological activity of peptides, proteins, and oligonucleotides remains an important challenge. (e.g., Lienkamp, et al. 2008 J A. Chem. Soc. 130, 9836-9843; Gabriel, et al. 2008 Biomacromolecules 9, 2980-2983.) There is a significant unmet need for novel approaches, compositions and methods that provide synthetic mimics of PTDs having improved cell-penetrating properties.

SUMMARY OF THE INVENTION

The invention is based in part on the discovery of that, unlike certain known PTDs, such as heptaarginine and polyarginine that require counterion for activation, a number of guanidinium-containing polymers and block copolymers are self-activating in anion transport across lipid bilayers. The invention provides novel monomers, oligomers and polymers (e.g., co-polymers) that are useful for the preparation of synthetic mimics of cell penetrating peptides. The invention additionally provides related-compositions and methods of preparations and use of the novel monomers, oligomers and polymers disclosed herein.

In one aspect, the invention generally relates to a block co-polymer having the Formula of (I):

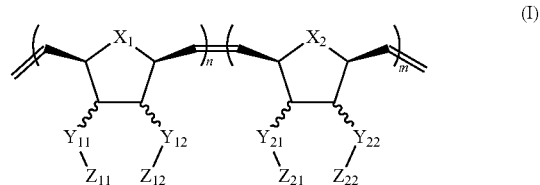

wherein
$X_1$, $X_2$ each is independently O, $CH_2$ or substituted $CH_2$;
$Y_{11}$, $Y_{12}$ each is independently a single bond or a linking group;
$Z_{11}$, $Z_{12}$ each is independently hydrogen, or an $-N(R_z)_2$, alkyl, substituted alkyl, aryl, substituted aryl group, with the proviso that at least one of $Z_{11}$ and $Z_{12}$ comprises $N(R_z)_2$ or

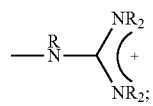

$Y_{21}$, $Y_{22}$ each is independently a single bond or a linking group;
$Z_{21}$, $Z_{22}$ each is independently hydrogen, or an $-OR_z$, alkyl, substituted alkyl, aryl, substituted aryl group;
$R_z$ each is independently hydrogen, or an alkyl, substituted alkyl, aryl, substituted aryl, poly(ethylene oxide) group;
R is hydrogen, a $C_1$-$C_6$ alkyl or a poly(ethylene oxide) group; and m, n each is independently an integer from about 2 to about 300.

In another aspect, the invention generally relates to a composition that includes: a polymer having a structural unit of Formula (II):

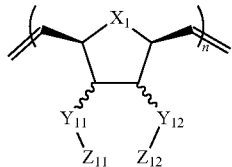

(II)

wherein $X_1$ is independently O, $CH_2$ or substituted $CH_2$;

$Y_{11}, Y_{12}$ each is independently a single bond or a linking group;

$Z_{11}, Z_{12}$ each is independently hydrogen, or an $—N(R_z)_2$, alkyl, substituted alkyl, aryl, substituted aryl group, with the proviso that at least one of $Z_{11}$ and $Z_{12}$ comprises $—N(R_z)_2$ or

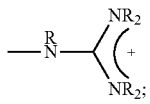

$R_z$ each is independently hydrogen, or an alkyl, substituted alkyl, aryl, substituted aryl, poly(ethylene oxide) group;

R is hydrogen, a $C_1$-$C_6$ alkyl group or a poly(ethylene oxide) group; and n is independently an integer from about 2 to about 300; and a therapeutic agent having a biological effect under physiological conditions.

In yet another aspect, the invention generally relates to a composition that includes: a polymer having a structural unit of Formula (II):

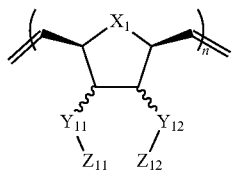

(II)

wherein $X_1$ is independently O, $CH_2$ or substituted $CH_2$;

$Y_{11}, Y_{12}$ each is independently a single bond or a linking group;

$Z_{11}, Z_{12}$ each is independently hydrogen, or an $—N(R_z)_2$, alkyl, substituted alkyl, aryl, substituted aryl group, with the proviso that a least one of $Z_{11}$ and $Z_{12}$ comprises $—N(R_z)_2$ or

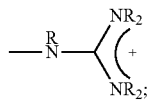

$R_z$ each is independently hydrogen, or an alkyl, substituted alkyl, aryl, substituted aryl, poly(ethylene oxide) group;

R is hydrogen, a $C_1$-$C_6$ alkyl group or a poly(ethylene oxide) group; and n is independently an integer from about 2 to about 300; and a diagnostic agent capable of emitting a detectable signal In yet another aspect, the invention generally relates to a block co-polymer having the Formula of (III):

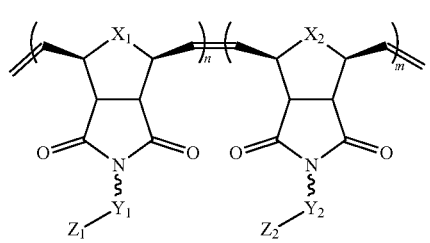

(III)

wherein $X_1, X_2$ each is independently O, $CH_2$ or substituted $CH_2$;

$Y_1$ is a linking group;

$Z_1$ is comprises $—N(R_z)_2$ or

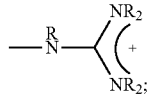

$Y_2$ is a single bond or a linking group;

$Z_2$ is hydrogen, or an alkyl or substituted alkyl group;

$R_z$ is hydrogen, or an alkyl, substituted alkyl, aryl, substituted aryl group;

R is hydrogen, a $C_1$-$C_{12}$ alkyl group or a poly(ethylene oxide) group; and m, n each is independently an integer from about 2 to about 300.

In yet another aspect, the invention generally relates to a block copolymer that includes a structural unit of the formula:

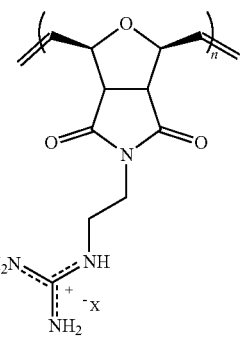

wherein X is an anion.

In yet another aspect, the invention generally relates to a composition that includes: a polymer having a structural unit of Formula (IV):

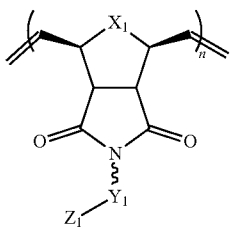

(IV)

wherein
$X_1$ is O, $CH_2$ or substituted $CH_2$;
$Y_1$ is a linking group;
$Z_1$ is comprises —N($R_z)_2$ or

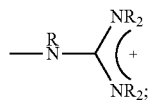

$R_z$ is hydrogen, or an alkyl, substituted alkyl, aryl, substituted aryl group;
R is hydrogen, a $C_1$-$C_{12}$ alkyl group or a poly(ethylene oxide) group; and
n is independently an integer from about 2 to about 300.
a therapeutic agent having a biological effect under physiological conditions.

In yet another aspect, the invention generally relates to a composition that includes: a polymer having a monomer of Formula (IV):

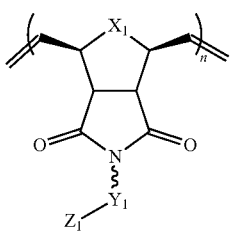

(IV)

wherein
$X_1$ is O, $CH_2$ or substituted $CH_2$;
$Y_1$ is a linking group;
$Z_1$ is comprises —N($R_z)_2$ or

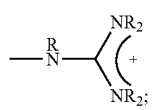

$R_z$ is hydrogen, or an alkyl, substituted alkyl, aryl, substituted aryl group;

R is hydrogen, a $C_1$-$C_{12}$ alkyl group or a poly(ethylene oxide) group; and
n is independently an integer from about 2 to about 300.
a diagnostic agent capable of emitting a detectable signal

BRIEF DESCRIPTION OF THE DRAWINGS

FIG. 14: GPC-UV trace of NBD-labeled polymer 6a.

FIG. 47: GPC IR-trace of $1^{st}$ (red curve) and $2^{nd}$ (black curve) blocks of Polymer 5a.

DEFINITIONS

Figure 1:
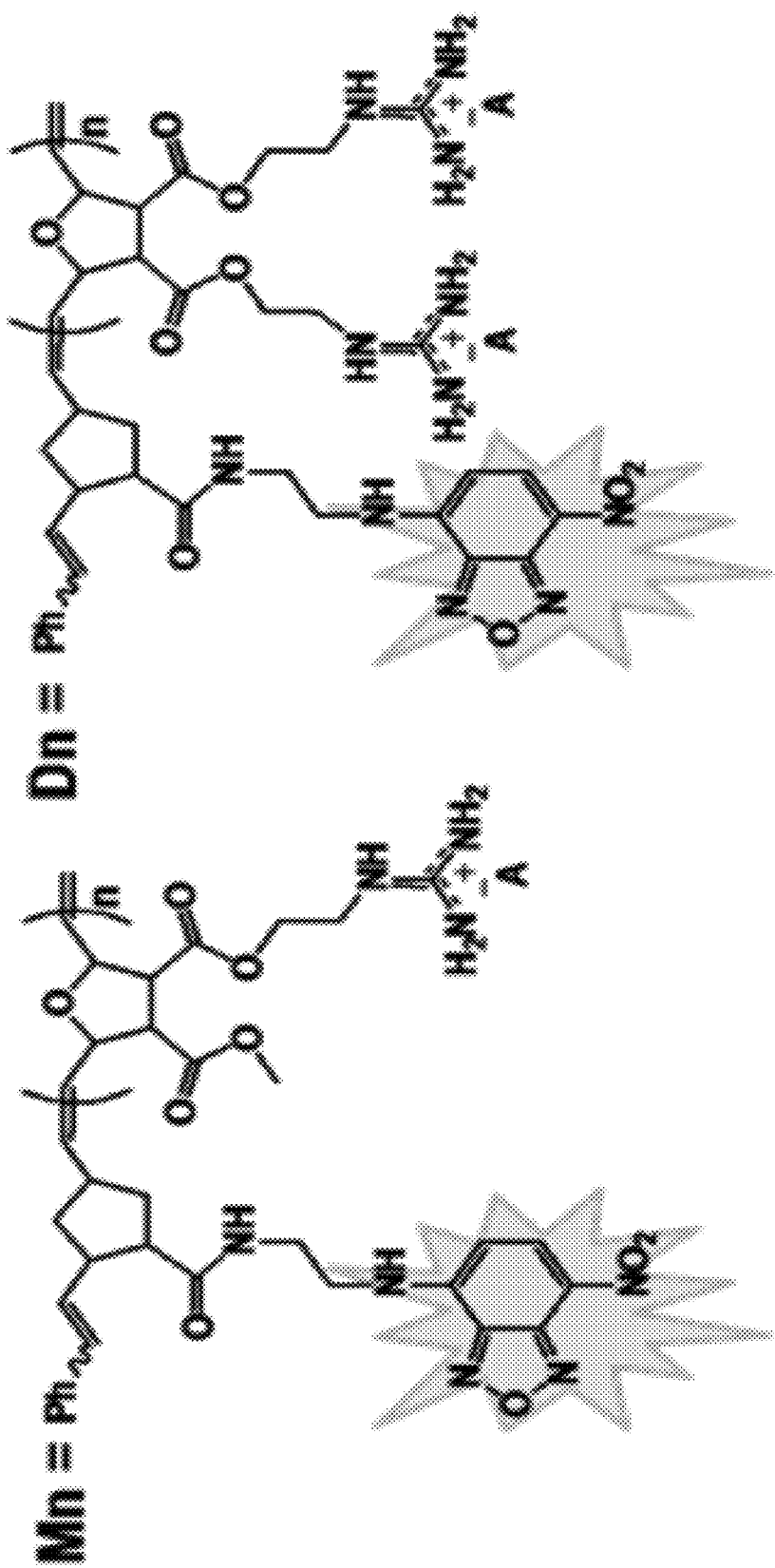
FIG. 1: Structures of Methyl-(Mn) and Di-(Dn) guanidinium polymers.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties.

As used herein, $(C_x-C_y)$ refers in general to groups that have from x to y (inclusive) carbon atoms. Therefore, for example, $C_1-C_6$ refers to groups that have 1, 2, 3, 4, 5, or 6 carbon atoms, which encompass $C_1-C_2$, $C_1-C_3$, $C_1-C_4$, $C_1-C_5$, $C_2-C_3$, $C_2-C_4$, $C_2-C_5$, $C_2-C_6$, and all like combinations. $(C_1-C_{20})$ and the likes similarly encompass the various combinations between 1 and 20 (inclusive) carbon atoms, such as $(C_1-C_6)$, $(C_1-C_{12})$ and $(C_3-C_{12})$.

As used herein, the term "$(C_x-C_y)$alkyl" refers to a saturated linear or branched free radical consisting essentially of x to y carbon atoms, wherein x is an integer from 1 to about 10 and y is an integer from about 2 to about 20. Exemplary $(C_x-C_y)$alkyl groups include "$(C_1-C_{20})$alkyl," which refers to a saturated linear or branched free radical consisting essentially of 1 to 20 carbon atoms and a corresponding number of hydrogen atoms. Exemplary $(C_1-C_{20})$alkyl groups include methyl, ethyl, n-propyl, isopropyl, n-butyl, isobutyl, dodecanyl, etc. Of course, other $(C_1-C_{20})$alkyl groups will be readily apparent to those of skill in the art given the benefit of the present disclosure.

DESCRIPTION OF THE INVENTION

The invention is based in part on the discovery that, unlike certain known PTDs (e.g., heptaarginine and polyarginine) that require counterion for activation, a number of novel guanidinium-containing polymers and block copolymers are self-activating in anion transport across lipid bilayers.

In one aspect, the invention generally relates to a block co-polymer having the Formula of (I):

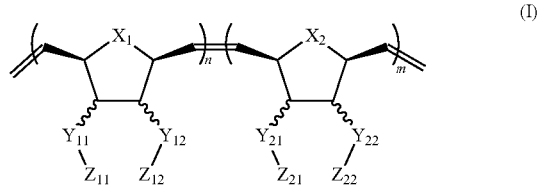

wherein $X_1$, $X_2$ each is independently O, $CH_2$ or substituted $CH_2$;

$Y_{11}$, $Y_{12}$ each is independently a single bond or a linking group;

$Z_{11}$, $Z_{12}$ each is independently hydrogen, or an —$N(R_z)_2$, alkyl, substituted alkyl, aryl, substituted aryl group, with the proviso that at least one of $Z_{11}$ and $Z_{12}$ comprises $N(R_z)_2$ or

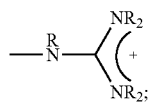

$Y_{21}$, $Y_{22}$ each is independently a single bond or a linking group;

$Z_{21}$, $Z_{22}$ each is independently hydrogen, an —$OR_z$, alkyl, substituted alkyl, aryl, substituted aryl group;

$R_z$ each is independently hydrogen, an alkyl, substituted alkyl, aryl, substituted aryl, poly(ethylene oxide) group;

R is hydrogen, a $C_1-C_6$ alkyl group or a poly(ethylene oxide) group; and m, n each is independently an integer from about 2 to about 300.

In certain embodiments, m and n are independently integers from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In certain embodiments of the block co-polymer, each of $X_1$ and $X_2$ is O; each of $Y_{11}$ and $Y_{12}$ is independently a linking group comprising a carbonyl group; each of $Z_{11}$ and $Z_{12}$ comprises

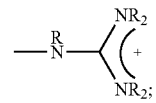

each of $Y_{21}$ and $Y_{22}$ is independently a linking group comprising a carbonyl group; each of $Z_{21}$, $Z_{22}$ is —$OR_z$, wherein at least one —$OR_z$ comprises an aryl group; each R is hydrogen; and each of m and n is selected from an integer from about 2 to about 24.

In certain embodiments of the block co-polymer, each of $X_1$ and $X_2$ is O; each of $Y_{11}$ and $Y_{12}$ is independently a linking group comprising a carbonyl group; each of $Z_{11}$ and $Z_{12}$ comprises $N(R_z)_2$; each of $Y_{21}$ and $Y_{22}$ is independently a linking group comprising a carbonyl group; each of $Z_{21}$, $Z_{22}$ is —$OR_z$, wherein at least one —$OR_z$ comprises an aryl group; each R is hydrogen; and each of m and n is selected from an integer from about 2 to about 24.

In certain embodiments of the block co-polymer, each of $X_1$ and $X_2$ is $CH_2$; each of $Y_{11}$ and $Y_{12}$ is independently a linking group comprising a carbonyl group; one of $Z_{11}$ and $Z_{12}$ comprises

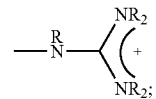

each of $Y_{21}$ and $Y_{22}$ is independently a linking group comprising a carbonyl group; each of $Z_{21}$, $Z_{22}$ is —$OR_z$, wherein at least one —$OR_z$ comprises an aryl group; each R is hydrogen; and each of m and n is selected from an integer from about 2 to about 24.

In certain embodiments of the block co-polymer, each of $X_1$ and $X_2$ is $CH_2$; each of $Y_{11}$ and $Y_{12}$ is independently a linking group comprising a carbonyl group; one of $Z_{11}$ and $Z_{12}$ comprises $N(R_z)_2$; each of $Y_{21}$ and $Y_{22}$ is independently a linking group comprising a carbonyl group; each of $Z_{21}$, $Z_{22}$ is —$OR_z$, wherein at least one —$OR_z$ comprises an aryl group; each R is hydrogen; and each of m and n is selected from an integer from about 2 to about 24.

In certain embodiments of the block co-polymer, each of $Y_{11}$, $Y_{12}$, $Y_{21}$ and $Y_{22}$ is independently a linking group comprising a carbonyl group and comprising a —O(CH$_2$)$_q$— or a —O(CH$_2$)$_q$—, wherein each q is independently an integer from about 1 to about 6 (e.g., 1, 2, 3, 4, 5, 6).

In certain embodiments, the block co-polymer is a component of a composition. The composition may further include a therapeutic agent having a biological effect under physiological conditions. The therapeutic agent may be a small molecule compound, a peptide, an antibody, a protein or a nucleic acid.

In certain embodiments, the block co-polymer is a component of a composition. The composition may further include a diagnostic agent capable of emitting a detectable signal. The diagnostic agent may include a fluorescent label, a radioactive label, or a quantum dot of label.

In another aspect, the invention generally relates to a composition that includes: a polymer having a structural unit of Formula (II):

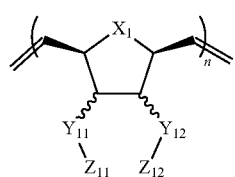

(II)

wherein
$X_1$ is independently O, CH$_2$ or substituted CH$_2$;
$Y_{11}$, $Y_{12}$ each is independently a single bond or a linking group;
$Z_{11}$, $Z_{12}$ each is independently hydrogen, or an —N(R$_z$)$_2$, alkyl, substituted alkyl, aryl, substituted aryl group, with the proviso that a least one of $Z_{11}$ and $Z_{12}$ comprises —N(R$_z$)$_2$ or

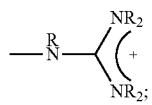

R$_z$ each is independently hydrogen, an alkyl, substituted alkyl, aryl, substituted aryl, poly(ethylene oxide) group;
R is hydrogen, a C$_1$-C$_6$ alkyl group, or a poly(ethylene oxide); and
n is independently an integer from about 2 to about 300; and
a therapeutic agent having a biological effect under physiological conditions.

In certain embodiments, n is an integer from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In some embodiments of the composition, the therapeutic agent comprises a small molecule compound. In some embodiments of the composition, the therapeutic agent comprises a peptide. In some embodiments of the composition, the therapeutic agent comprises an antibody. In some embodiments of the composition, the therapeutic agent comprises a protein. In some embodiments of the composition, the therapeutic agent comprises a nucleic acid.

In some embodiments of the composition, the polymer comprises a structural unit selected from:

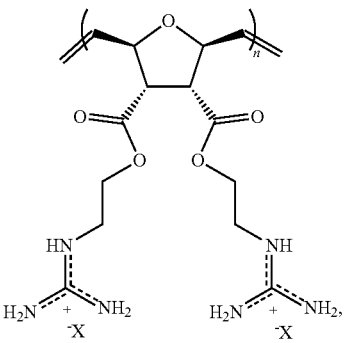

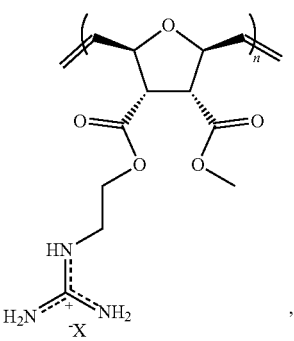

,

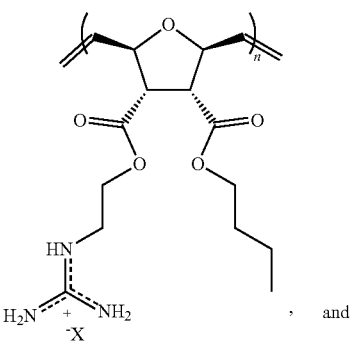

, and

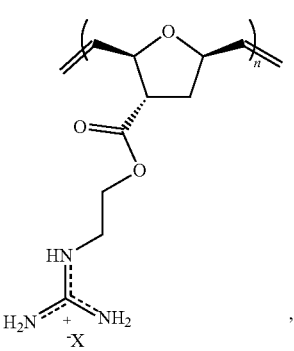

, wherein each X is independently a counter anion.

In some embodiments of the composition, the polymer comprises a structural unit of the formula:

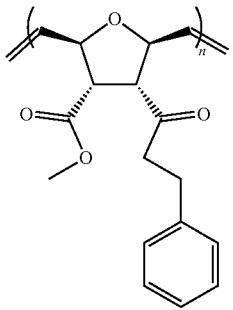

Each of $Y_{11}$ and $Y_{12}$ may be independently a linking group that includes a carbonyl group and —O(CH$_2$)$_q$—, wherein q is an integer from about 1 to about 6 (e.g., 1, 2, 3, 4, 5, 6).

In some embodiments, each of m and n is an integer from about 4 to about 16.

In another aspect, the invention generally relates to a composition comprising: a polymer having a monomer of Formula (II):

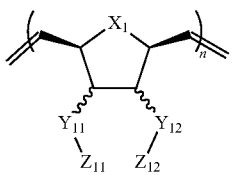

(II)

wherein
$X_1$ is independently O, CH$_2$ or substituted CH$_2$;
$Y_{11}$, $Y_{12}$ each is independently a single bond or a linking group;
$Z_{11}$, $Z_{12}$ each is independently hydrogen, an —N(R$_z$)$_2$, alkyl, substituted alkyl, aryl, substituted aryl group, with the proviso that a least one of $Z_{11}$ and $Z_{12}$ comprises —N(R$_z$)$_2$ or

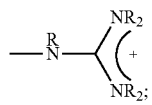

$R_z$ each is independently hydrogen, an alkyl, substituted alkyl, aryl, substituted aryl, poly(ethylene oxide) group;
R is hydrogen, a C$_1$-C$_6$ alkyl group or a poly(ethylene oxide); and
n is independently an integer from about 2 to about 300; and
a diagnostic agent capable of emitting a detectable signal.

In some embodiments of the composition, the diagnostic agent includes a fluorescent label. In some embodiments of the composition, the diagnostic agent includes a radioactive label. In some embodiments of the composition, the diagnostic agent includes a quantum dot label.

In some embodiments, the composition includes the polymer comprising a structural unit selected from:

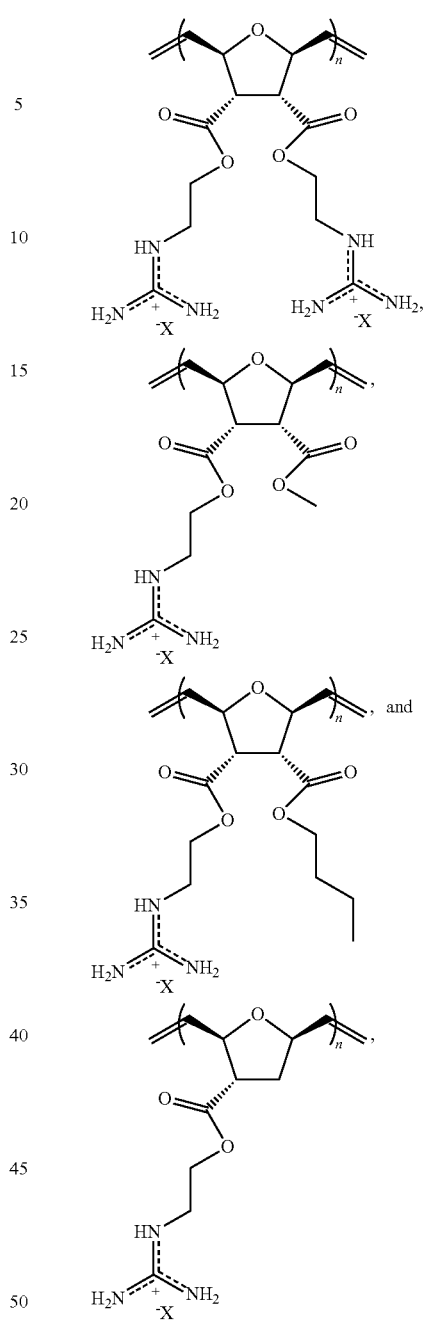

wherein each X is independently a counter anion.

$Y_{11}$ and $Y_{12}$ may be independently a linking group comprising a carbonyl group and comprising a —O(CH$_2$)$_q$— or a —O(CH$_2$)$_q$—, wherein q is an integer from about 1 to about 6. Each of m and n may be an integer from about 4 to about 16, for example.

The therapeutic or diagnostic agent may be covalently bonded to or non-covalently associated with the polymer of the invention.

In yet another aspect, the invention generally relates to a block co-polymer having the Formula of (III):

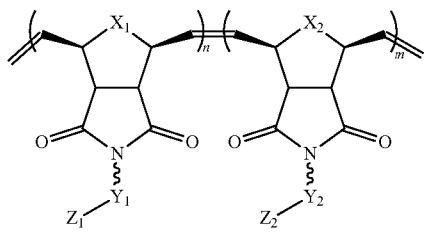

(III)

wherein
$X_1$, $X_2$ each is independently O, $CH_2$ or substituted $CH_2$;
$Y_1$ is a linking group;
$Z_1$ is comprises —$N(R_z)_2$ or

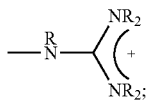

$Y_2$ is a single bond or a linking group;
$Z_2$ is hydrogen, an alkyl or substituted alkyl group;
$R_z$ is hydrogen, an alkyl, substituted alkyl, aryl, substituted aryl group;
R is hydrogen, a $C_1$-$C_{12}$ alkyl group or a poly(ethylene oxide) group; and
m, n each is independently an integer from about 2 to about 300.

In certain embodiments, m and n are independently integers from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In some embodiments of the block co-polymer, each of $X_1$ and $X_2$ is O; $Y_1$ is a linking group comprising a carbonyl group; $Y_2$ is a single bond; $Z_1$ comprises

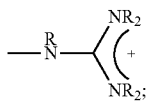

$Z_2$ is R; each R is hydrogen, an alkyl or substituted alkyl group; and each of m and n is selected from an integer from about 4 to about 24.

In some embodiments of the block co-polymer, each of $X_1$ and $X_2$ is O; $Y_1$ is a linking group comprising a carbonyl group; $Y_2$ is a single bond; $Z_1$ comprises —$N(R_z)_2$; $Z_2$ is R; each R is hydrogen, an alkyl or substituted alkyl group; and each of m and n is selected from an integer from about 4 to about 24.

In some embodiments of the block co-polymer, each of $X_1$ and $X_2$ is O; each of $Y_1$ and $Y_2$ is a linking group comprising a carbonyl group; $Z_1$ comprises

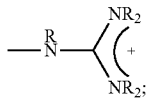

$Z_2$ comprises —$N(R_z)_2$; each R is hydrogen, an alkyl or substituted alkyl group; and each of m and n is selected from an integer from about 4 to about 24.

In certain embodiments, the block co-polymer has the formula of:

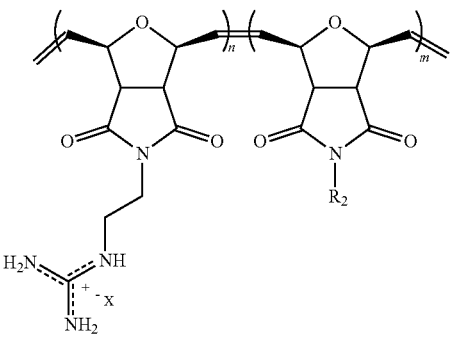

wherein $R_2$ is a $C_1$-$C_{12}$ alkyl or substituted alkyl group, an aryl or substituted aryl group, or a poly(ethylene oxide) group; X is a counter anion.

In yet another aspect, the invention generally relates to a block copolymer that includes the structural unit of the formula:

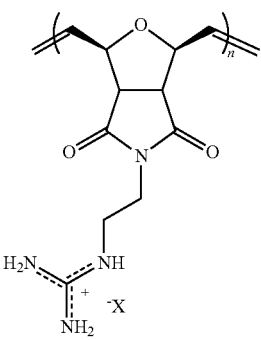

wherein X is a counter anion.

In certain embodiments, the block co-polymer may further include a structural unit of the formula:

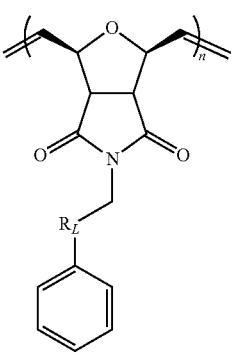

wherein $R_L$ is a —$(CH_2)_q$—, wherein q is an integer from about 1 to about 6 (e.g., 1, 2, 3, 4, 5, 6).

In certain embodiments, the block co-polymer may further include a structural unit of the formula:

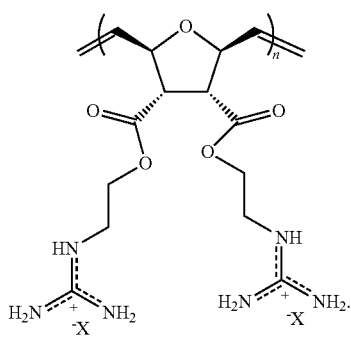

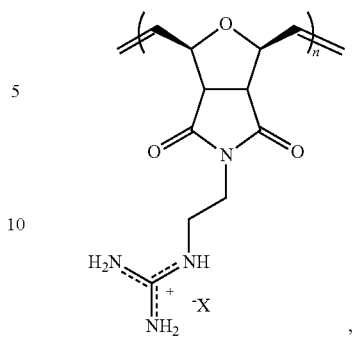

In yet another aspect, the invention generally relates to a composition that includes: a polymer having a structural unit of Formula (IV):

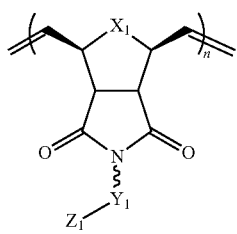
(IV)

wherein X is a counter anion.

In yet another aspect, the invention generally relates to a composition that includes a polymer comprising a structural unit of Formula (IV):

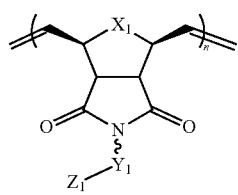
(IV)

wherein $X_1$ is O, $CH_2$ or substituted $CH_2$;

$Y_1$ is a linking group;

$Z_1$ is comprises —$N(R_z)_2$ or

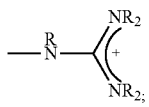

$R_z$ is hydrogen, an alkyl, substituted alkyl, aryl, substituted aryl group;

R is hydrogen or a $C_1$-$C_{12}$ alkyl group or a poly(ethylene oxide) group; and n is independently an integer from about 2 to about 300. a therapeutic agent having a biological effect under physiological conditions.

In some embodiments of the composition, the therapeutic agent is a small molecule compound. In some embodiments of the composition, the therapeutic agent is a peptide. In some embodiments of the composition, the therapeutic agent is an antibody. In some embodiments of the composition, the therapeutic agent is a protein. In some embodiments of the composition, the therapeutic agent a nucleic acid.

In certain embodiments, the polymer comprises a structural unit of the formula:

wherein $X_1$ is O, $CH_2$ or substituted $CH_2$;

$Y_1$ is a linking group;

$Z_1$ is comprises —$N(R_z)_2$ or

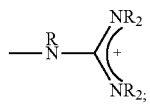

$R_z$ is hydrogen, an alkyl, substituted alkyl, aryl, substituted aryl group;

R is hydrogen or a $C_1$-$C_{12}$ alkyl group or a poly(ethylene oxide) group; and n is independently an integer from about 2 to about 300. a diagnostic agent capable of emitting a detectable signal.

In some embodiments of the composition, the diagnostic agent includes a fluorescent label. In some embodiments of the composition, the diagnostic agent includes a radioactive label. In some embodiments of the composition, the diagnostic agent includes a quantum dot label.

In certain embodiments, the polymer comprises a structural unit of the formula:

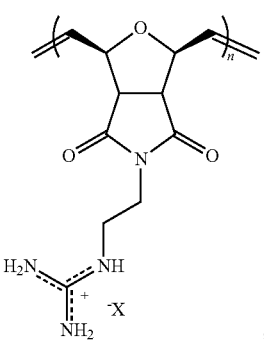

wherein X is a counter anion.

Figure 33:
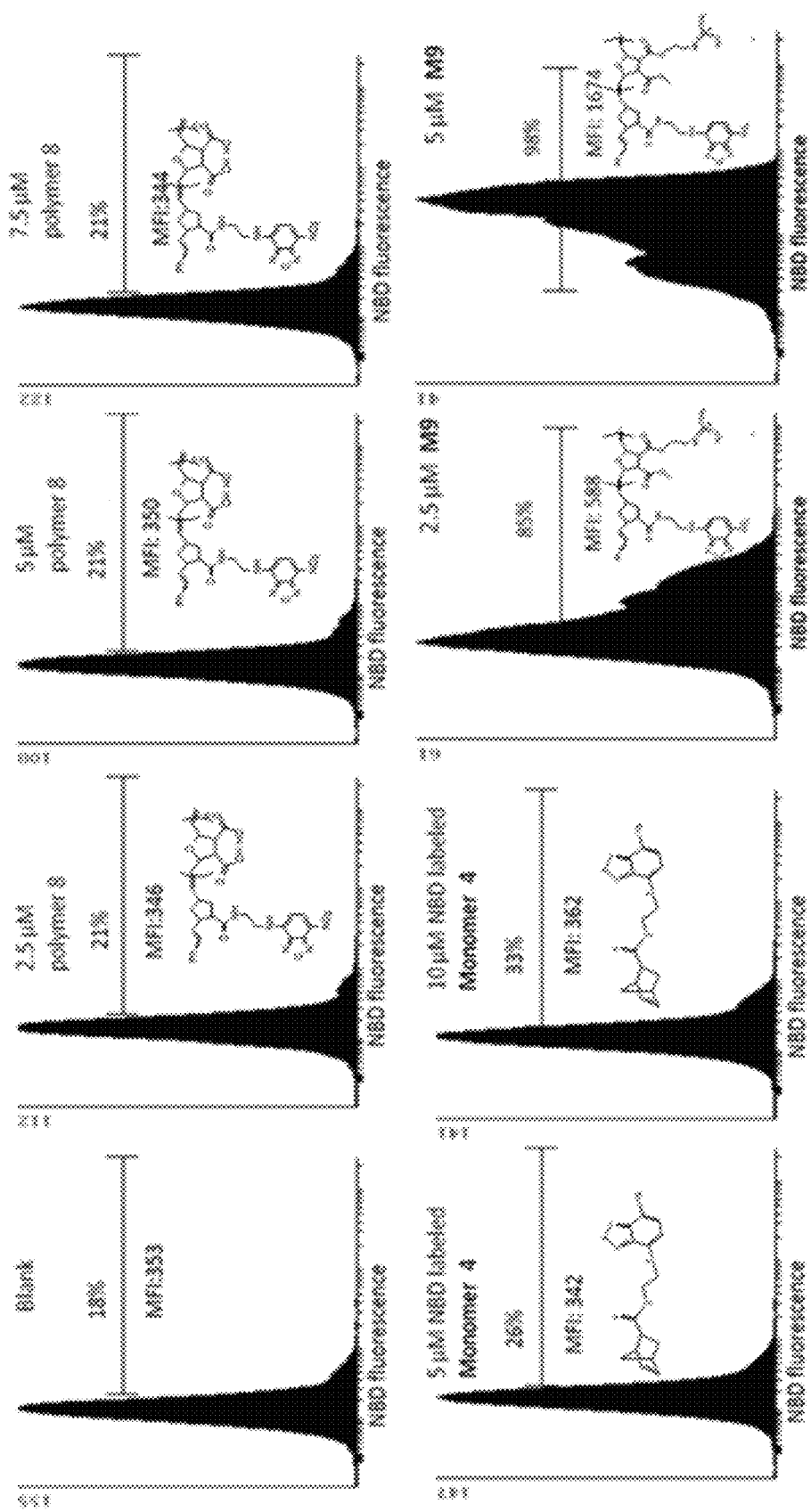
FIG. 33: Cellular uptake assay for negative controls. Jurkat T cells were treated with NBD-labeled polymer 8, monomer 4 or M9 to demonstrate that NBD dye does not have an effect on the internalization of molecules. Neither NBD-labeled polymer 8 nor the monomer 4 were able enter to the cells even at higher concentrations. On the other hand, M9 had superior uptake efficiency at a concentration of 2.5 μM, and furthermore its internalization efficiency was doubled at 5 μM.
Figure 34:
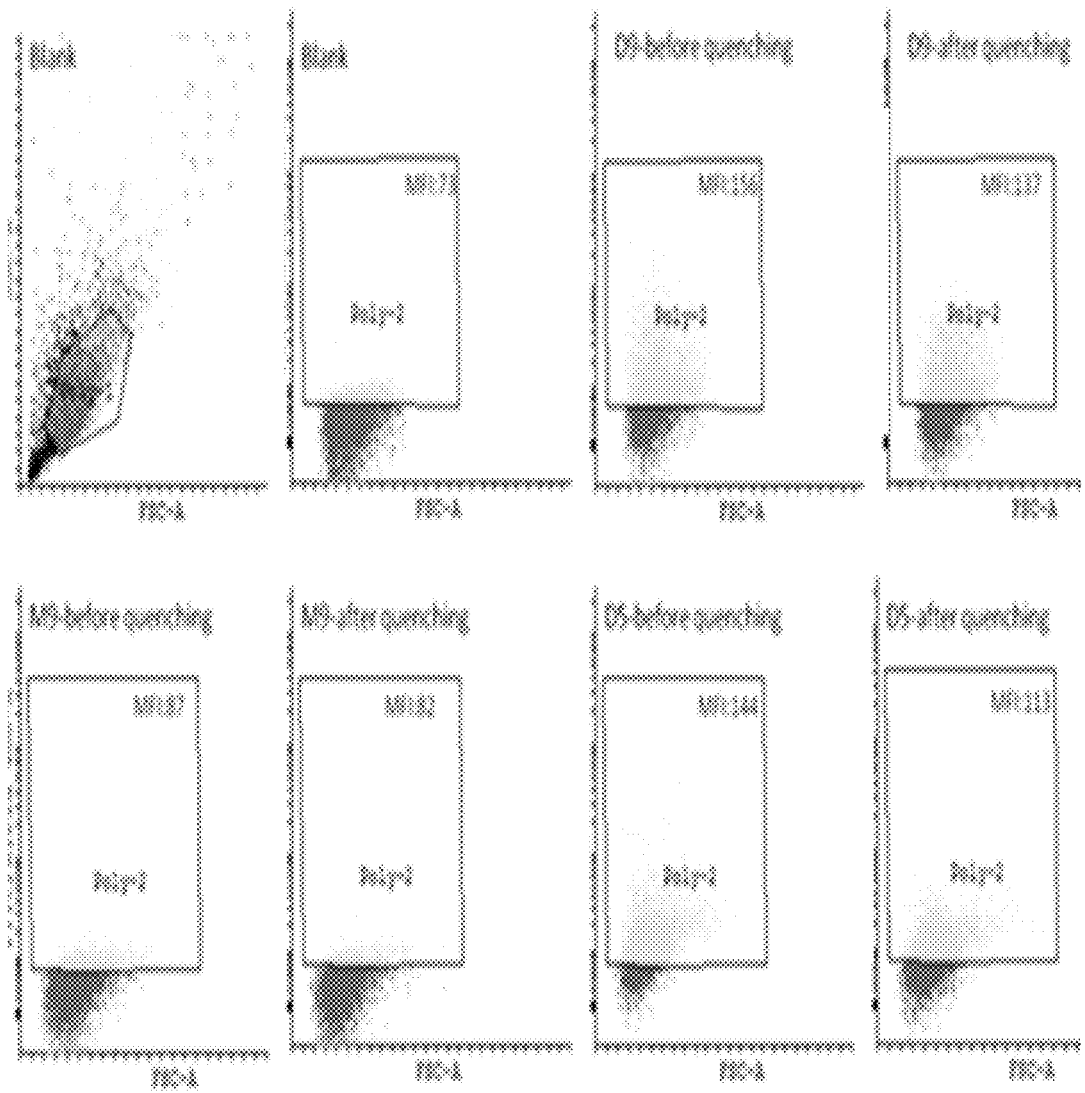
FIG. 34: HEK293T cells dot plots showing NBD-positive cells.
Figure 34:
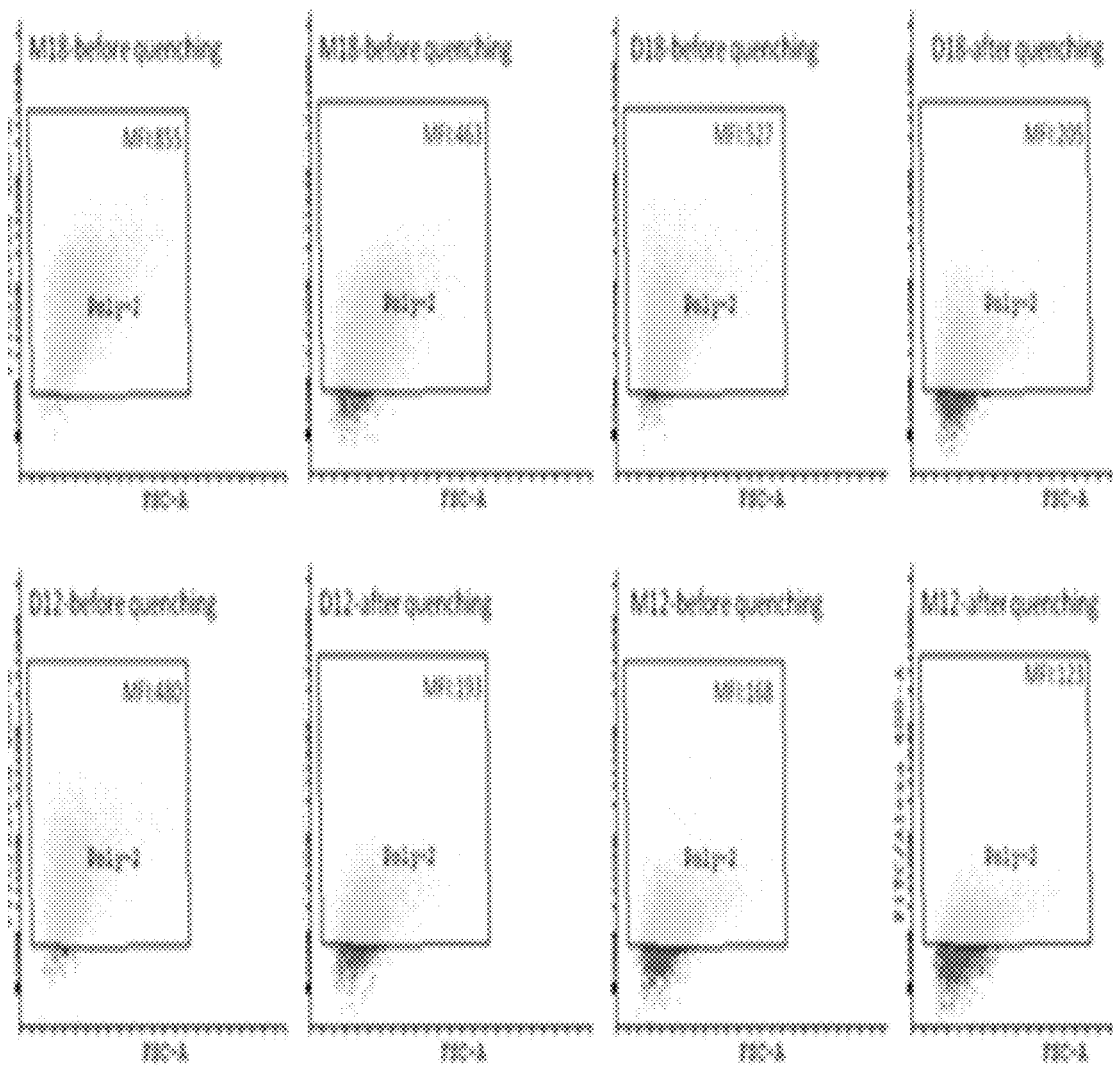
Figure 35:
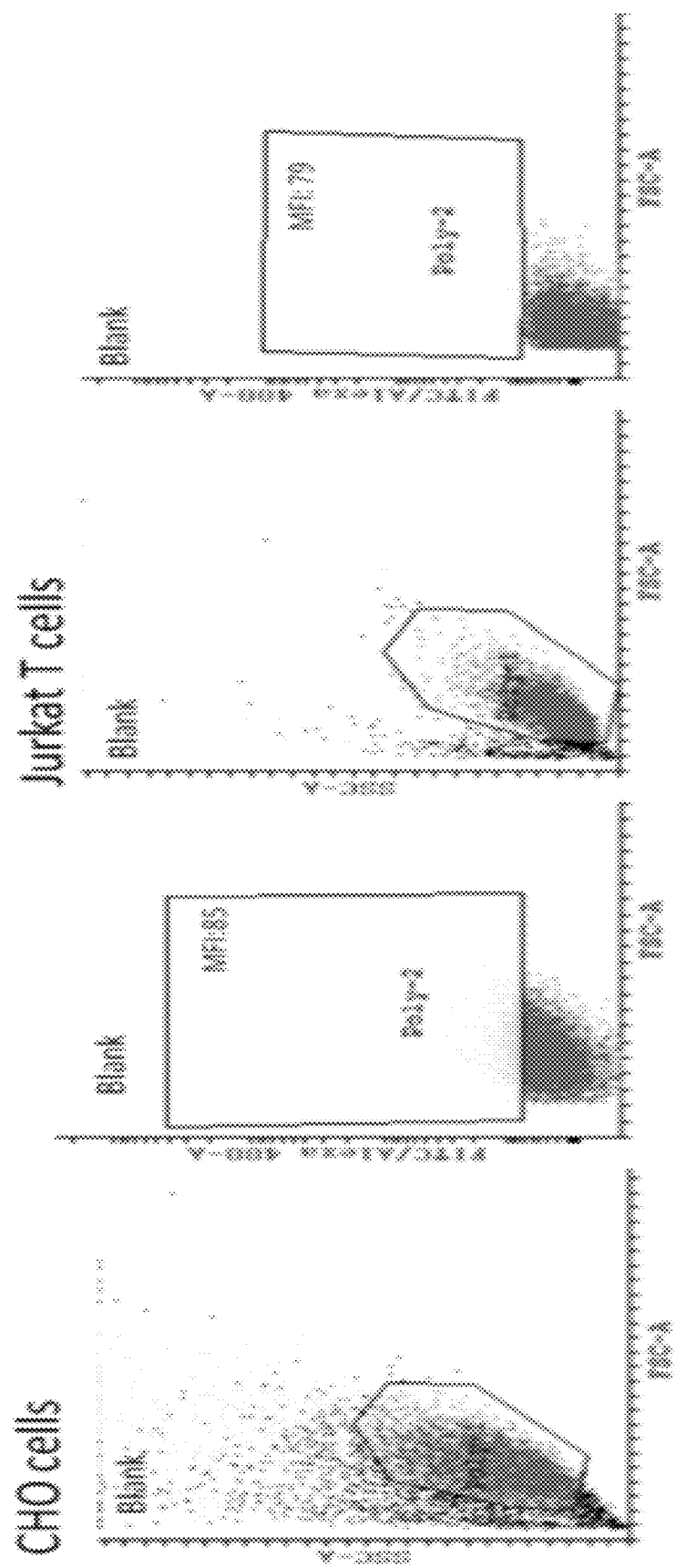
FIG. 35: Untreated controls, CHO and Jurkat T cells. FIG. S31: CHO cells dot plots showing NBD-positive cells.
Figure 36:
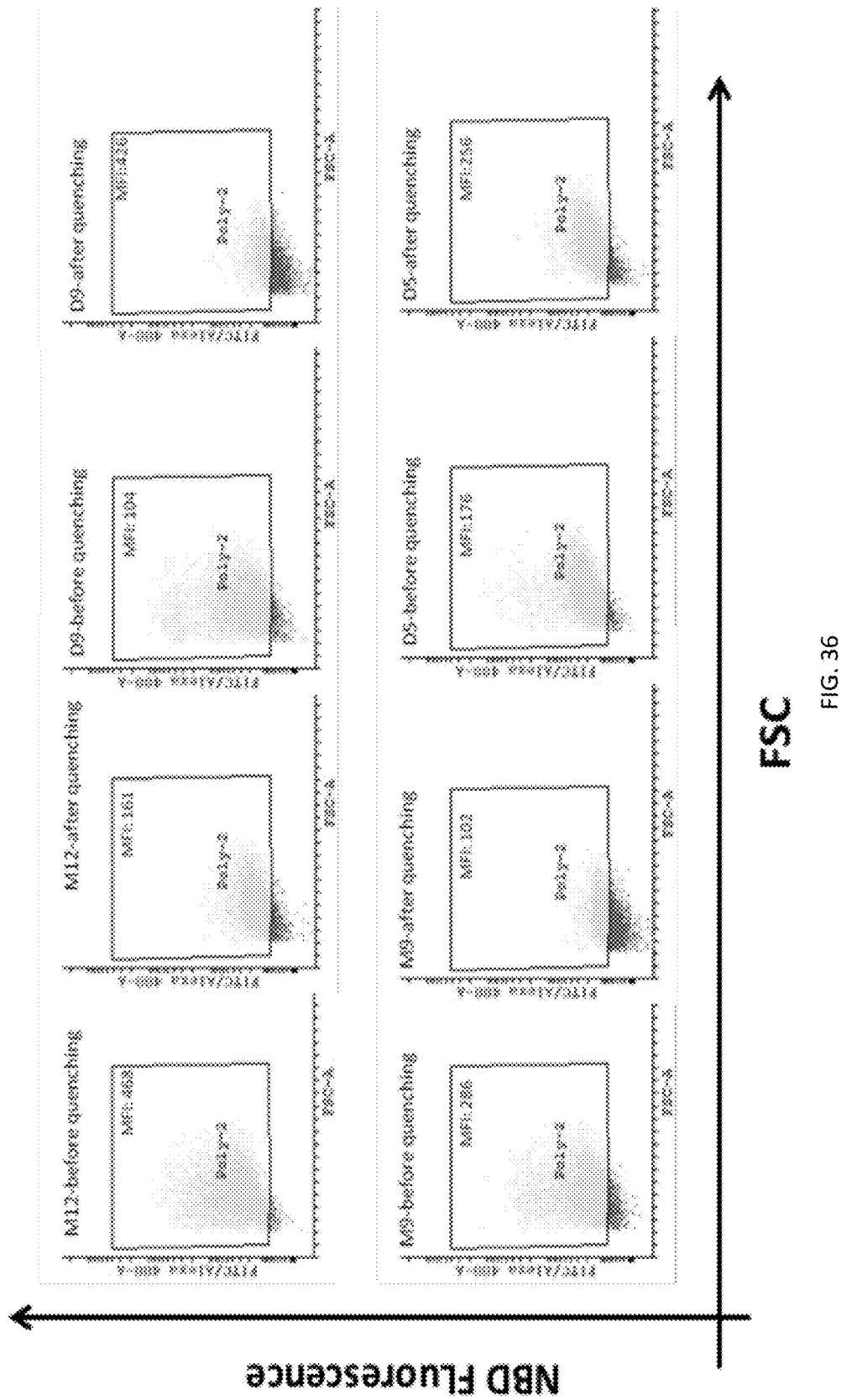
FIG. 36: CHO cells dot plots showing NBD-positive cells.
Figure 37:
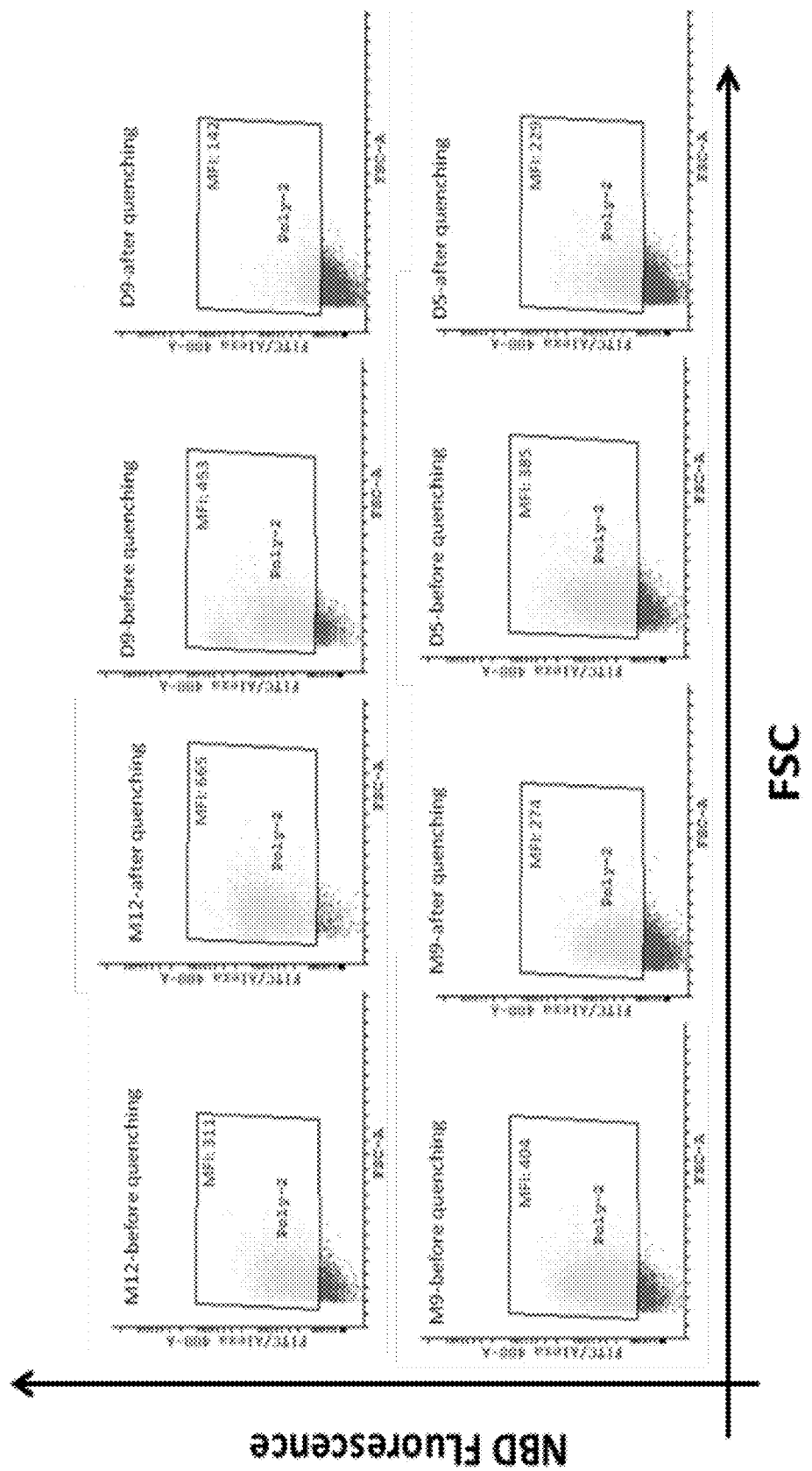
FIG. 37: Jurkat T cells dot plots showing NBD-positive cells.

With this understanding of PTD activity as background, the cellular uptake properties of the guanidinium-rich structures shown in FIG. 1 were designed, synthesized and studied. In order to track the polymers inside cells, they were labeled with a green fluorescent molecule, 7-chloro-4-nitrobenzo-2-oxa-1,3-diazole (NBD), by a post-functionalization method. (Roberts, et al. 2004 Org. Lett. 63, 253-3255.) Since most PTDs have relatively short sequences, the choice of dye molecule is important, as it can significantly impact the overall molecular structure. Recently, the effect of fluorescein on cellular uptake and distribution of an octaarginine (R8) derivative was described. In the presence of the fluorescein tag, these R8 derivatives were observed in both the cytoplasm and nucleus. Without fluorescein, however, only punctuate cytoplasmic staining was observed. (Puckett, et al. 2009 J. Am. Chem. Soc. 131, 8738-8739.) This is an illustrative example on how the addition of a large dye molecule can easily alter the cellular uptake properties of a molecular transporter. NBD was chosen as it is one of the smallest dyes available and, therefore, has a limited impact on the internalization activity of these polymers (FIG. 33).

In addition to evaluating the importance of chain length on internalization efficiency, this synthetic scaffold also allows us to study the effect of 'guanidine density' on intracellular uptake in a way that previous structures could not. For example, FIG. 1 shows two chemical structures, Mn and Dn, in which two sequences with the same chain length (n=degree of polymerization) were prepared but those based on Dn have twice the density of guanidine groups as those based on Mn. Testing these newly designed PTDMs in three different cell lines, HEK293T, CHO and Jurkat T cells, demonstrated internalization was universal, while the best synthetic transporter showed a small dependence on cell type. Internalization assays at 4° C. highlighted the presence of energy- and temperature-independent pathways, implying that these PTDMs may be excellent delivery vectors as they avoid the endosomal entrapment which is known to decrease the efficiency and bioavailability of both the transporters and the cargo. (Cheung, et al. 2009 J Control Release 137, 2-7; Abes, et al. 2006 J Control Release 110, 595-604.) These results demonstrate that it is possible to introduce biological character to synthetic polymers so that they can act like PTDs and, in fact, are more efficient than one of the best peptides, R9.

Figure 5:
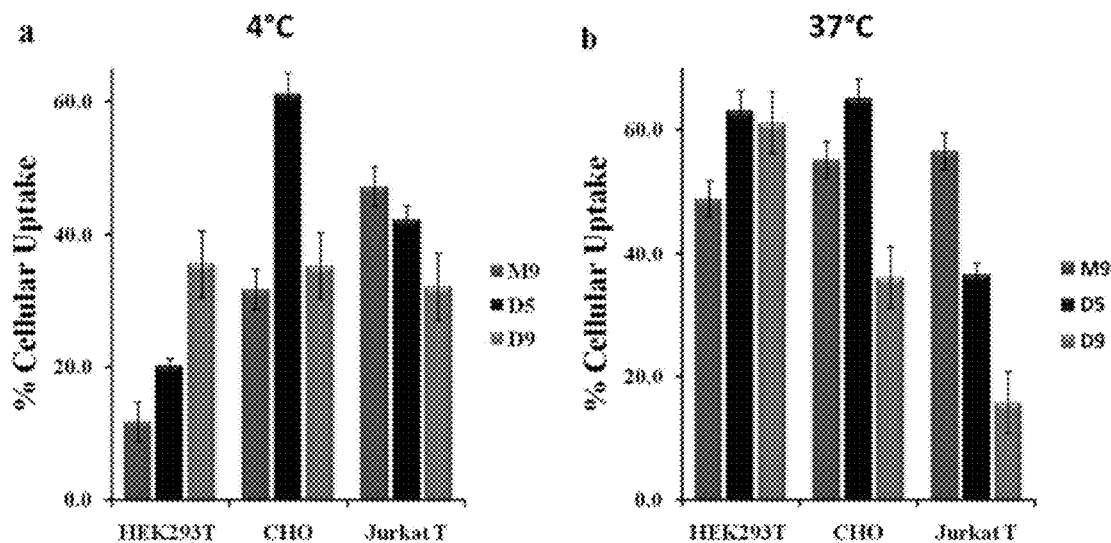
FIG. 5: Comparison of the percent cellular uptake of NBD-labeled M9, D5 and D9 in HEK293T, CHO and Jurkat T cells at (a) 4° C. and (b) 37° C. HEK293T and CHO cells were incubated with 5 μM NBD-labeled polymers, and Jurkat T cells were incubated with 2.5 μM NBD-labeled polymers. For the calculation of % internalization, experiments were done with dithionite quenched and without dithionite treated cells and the percent ratio of internalization represents the transduction efficiency of the molecules. Each point is the mean±S.D. of three separate determinations.
Figure 6:
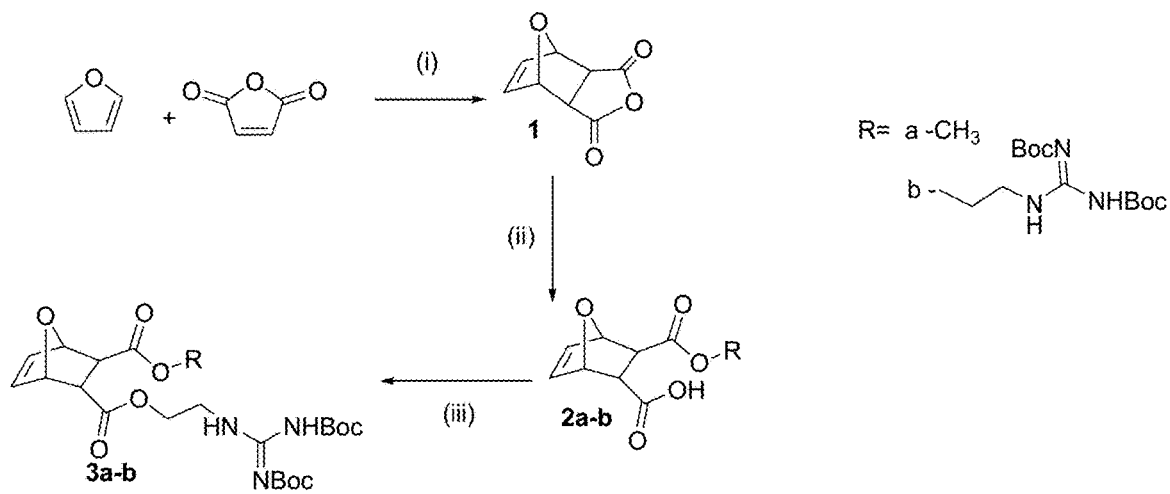
FIG. 6: Synthesis of monomers.
Figure 7:
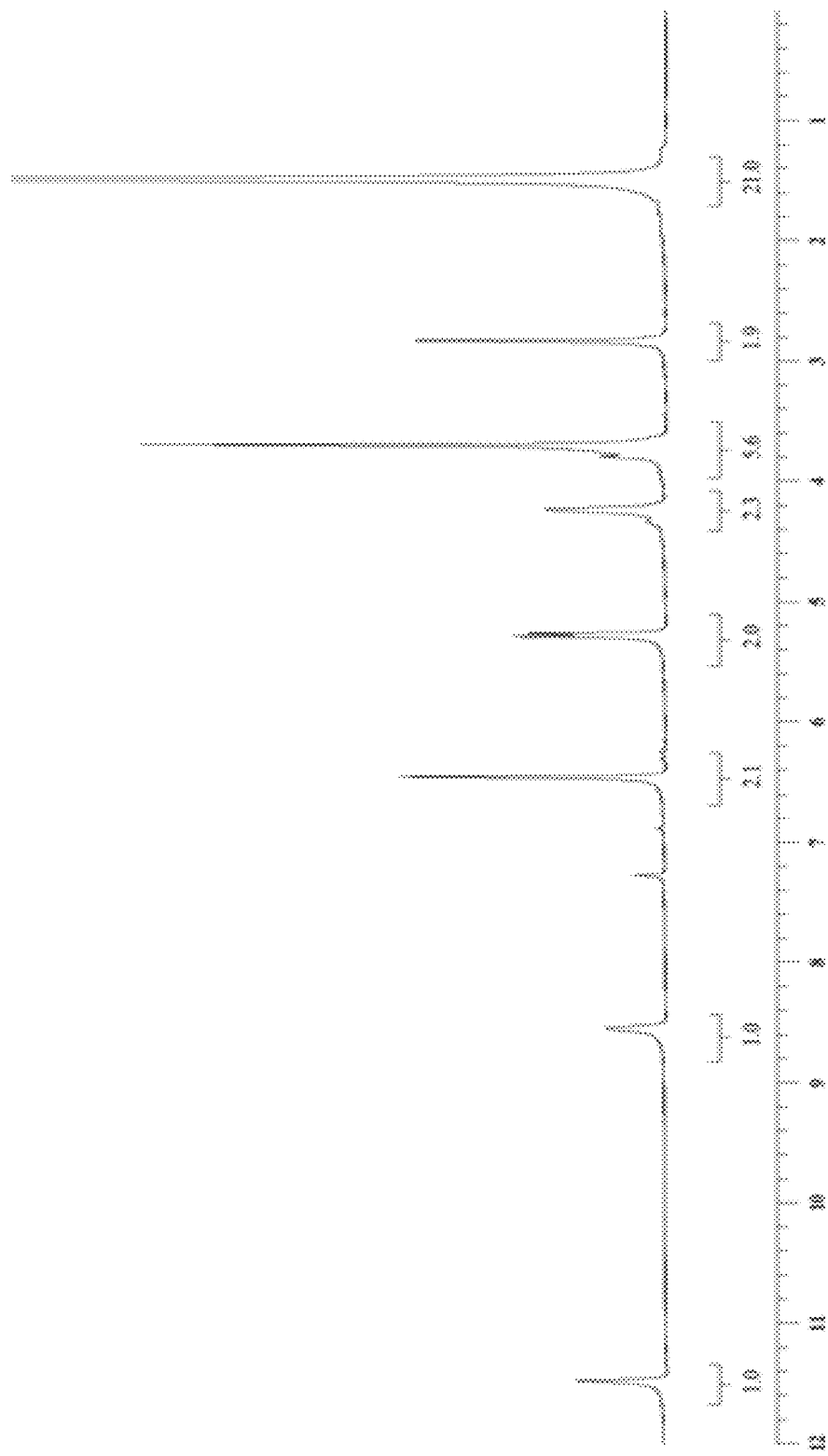
FIG. 7: $^1$H NMR of Compound 3a, $CDCl_3$.
Figure 8:
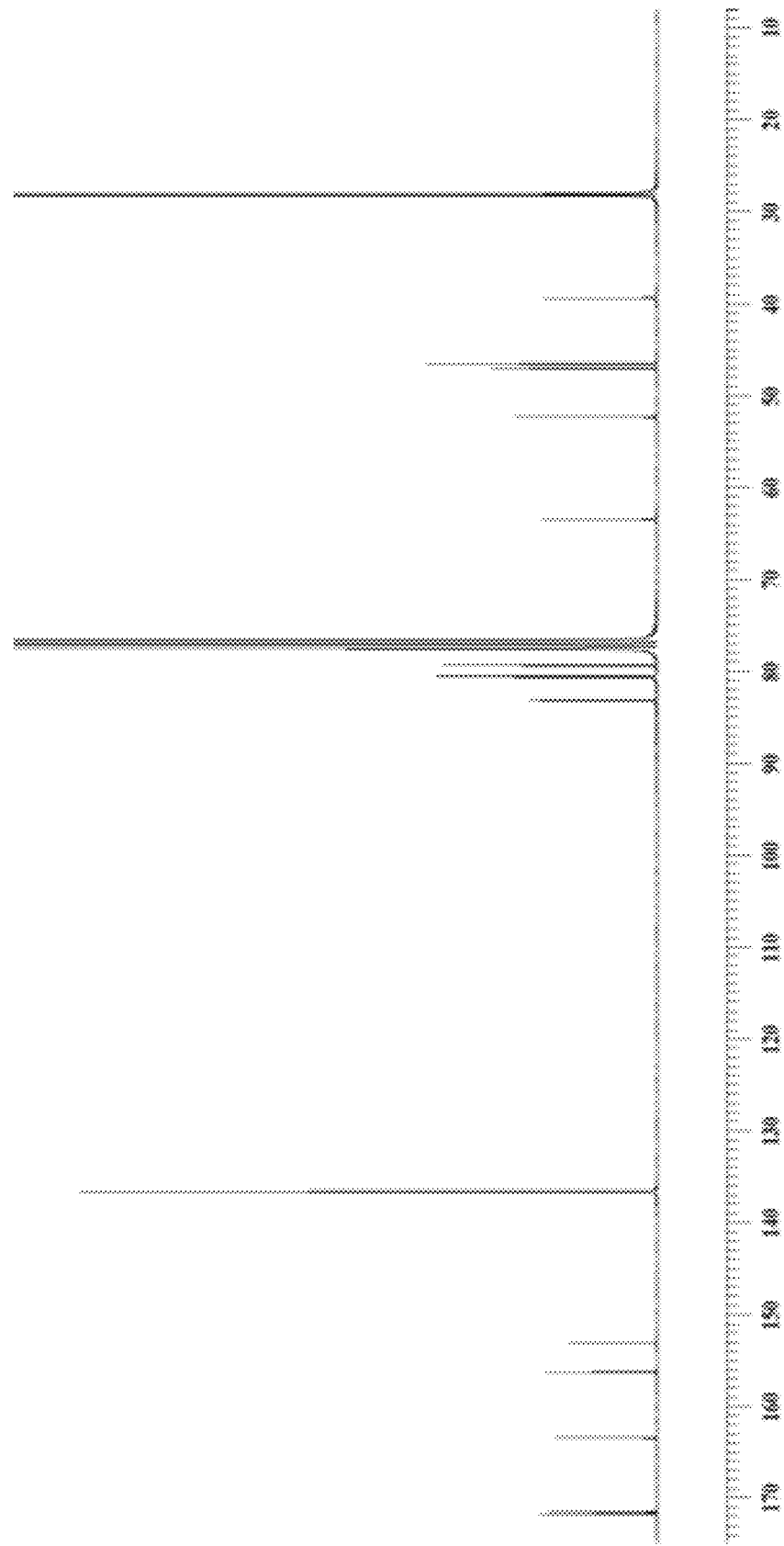
FIG. 8: $^{13}$C NMR of Compound 3a, $CDCl_3$.
Figure 9:
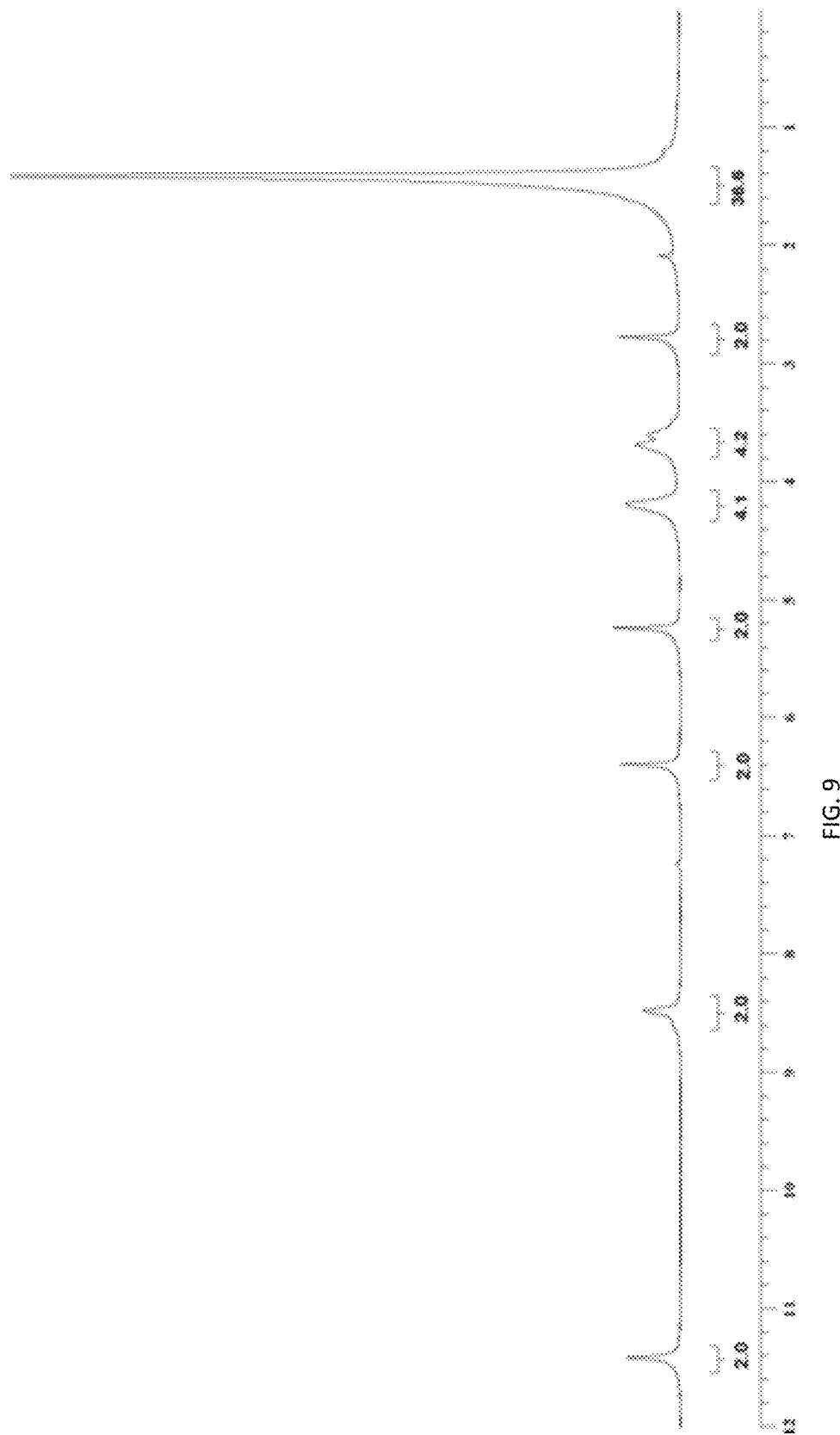
FIG. 9: $^1$H NMR of Compound 3b, $CDCl_3$.
Figure 10:
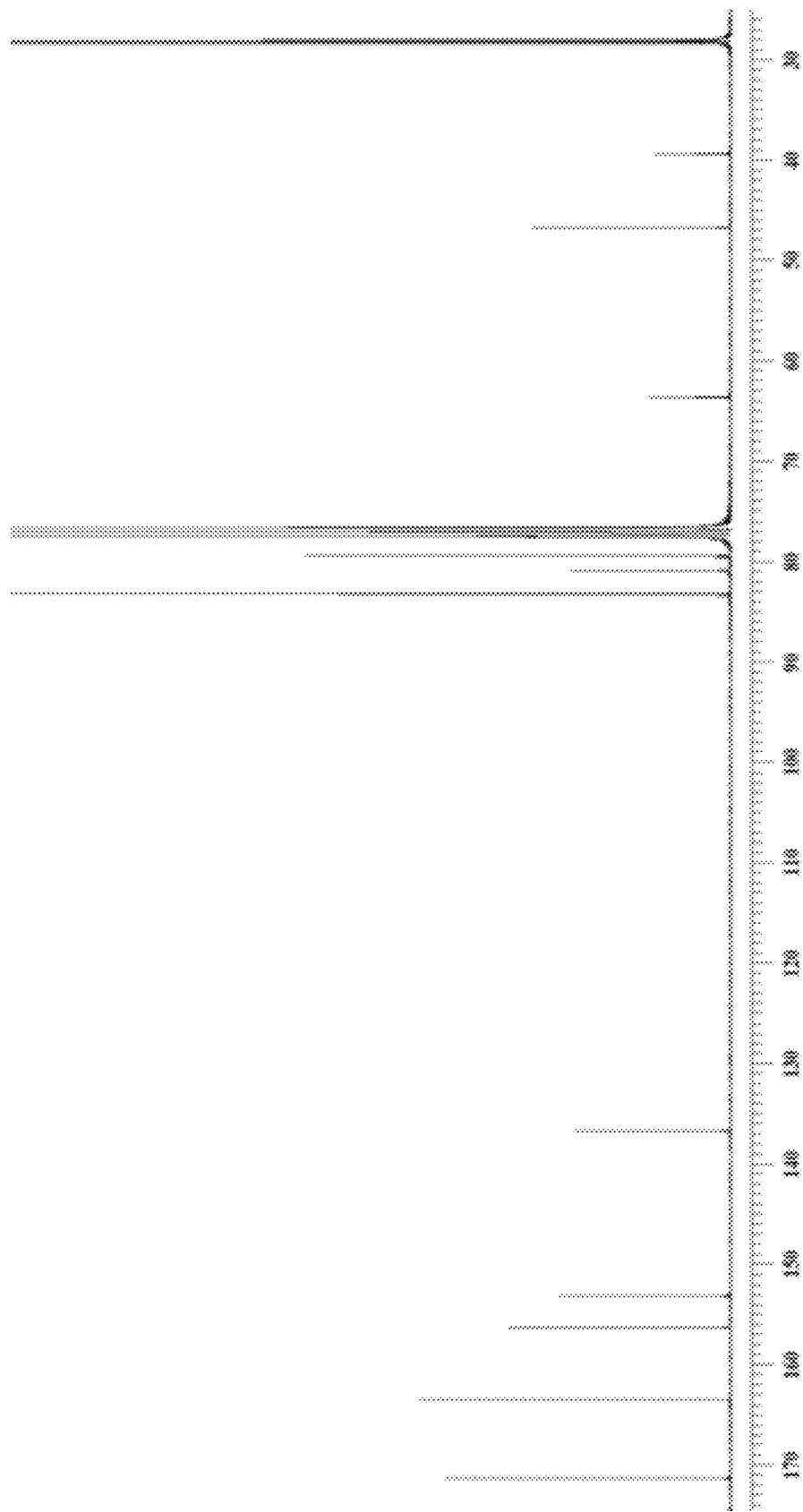
FIG. 10: $^{13}$C NMR of Compound 3b, $CDCl_3$.
Figure 11:
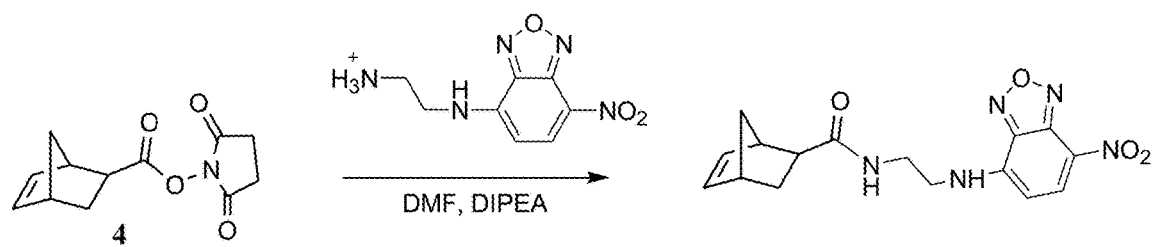
FIG. 11: Synthesis of NBD-labeled Compound 4.
Figure 12:
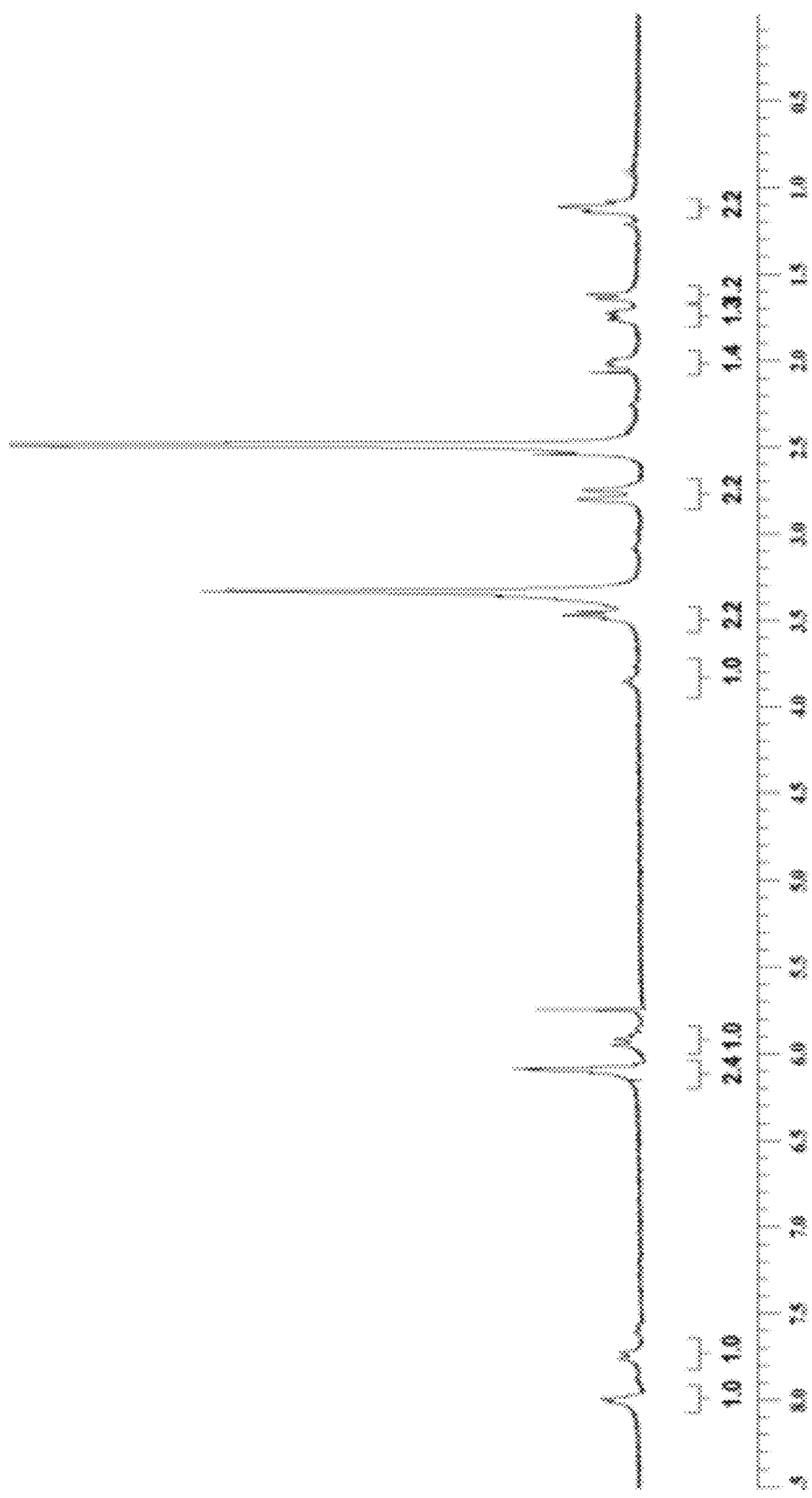
FIG. 12: $^1$H NMR of NBD-labeled compound 4, DMSO-d6.
Figure 13:
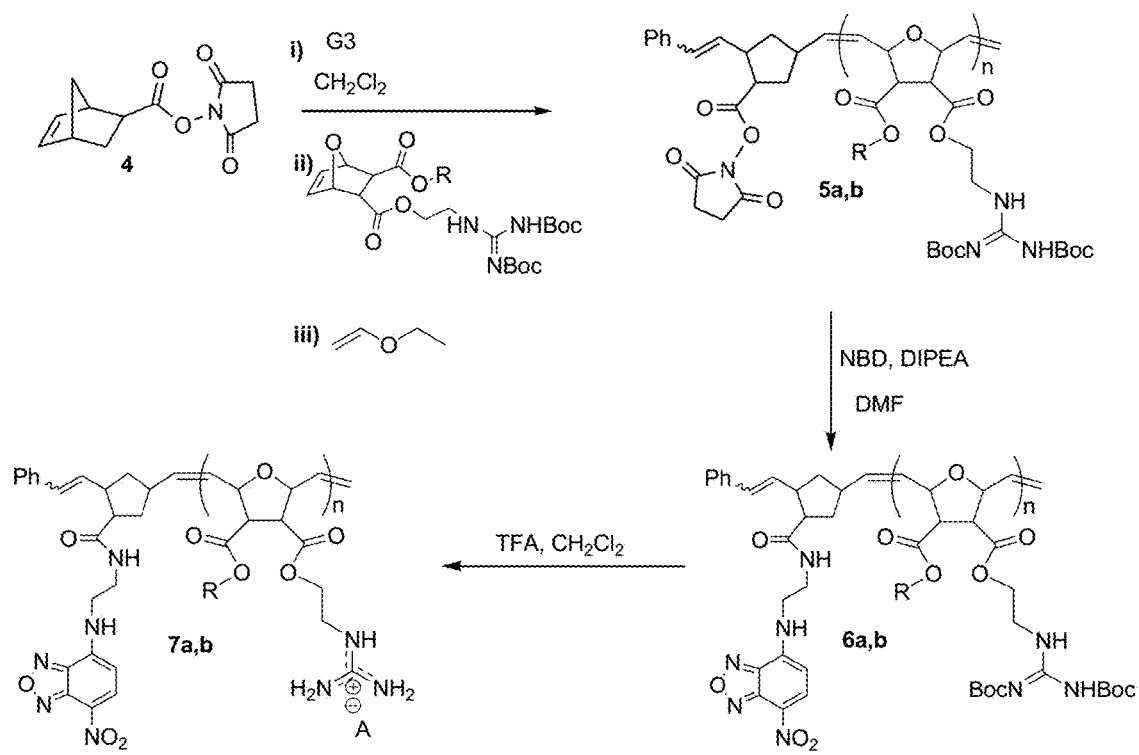
FIG. 13: Synthesis of NBD-labeled polymers.
Figure 14:
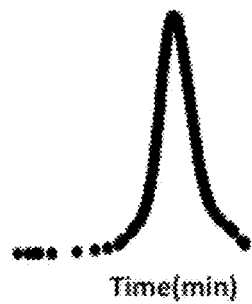
Figure 15:
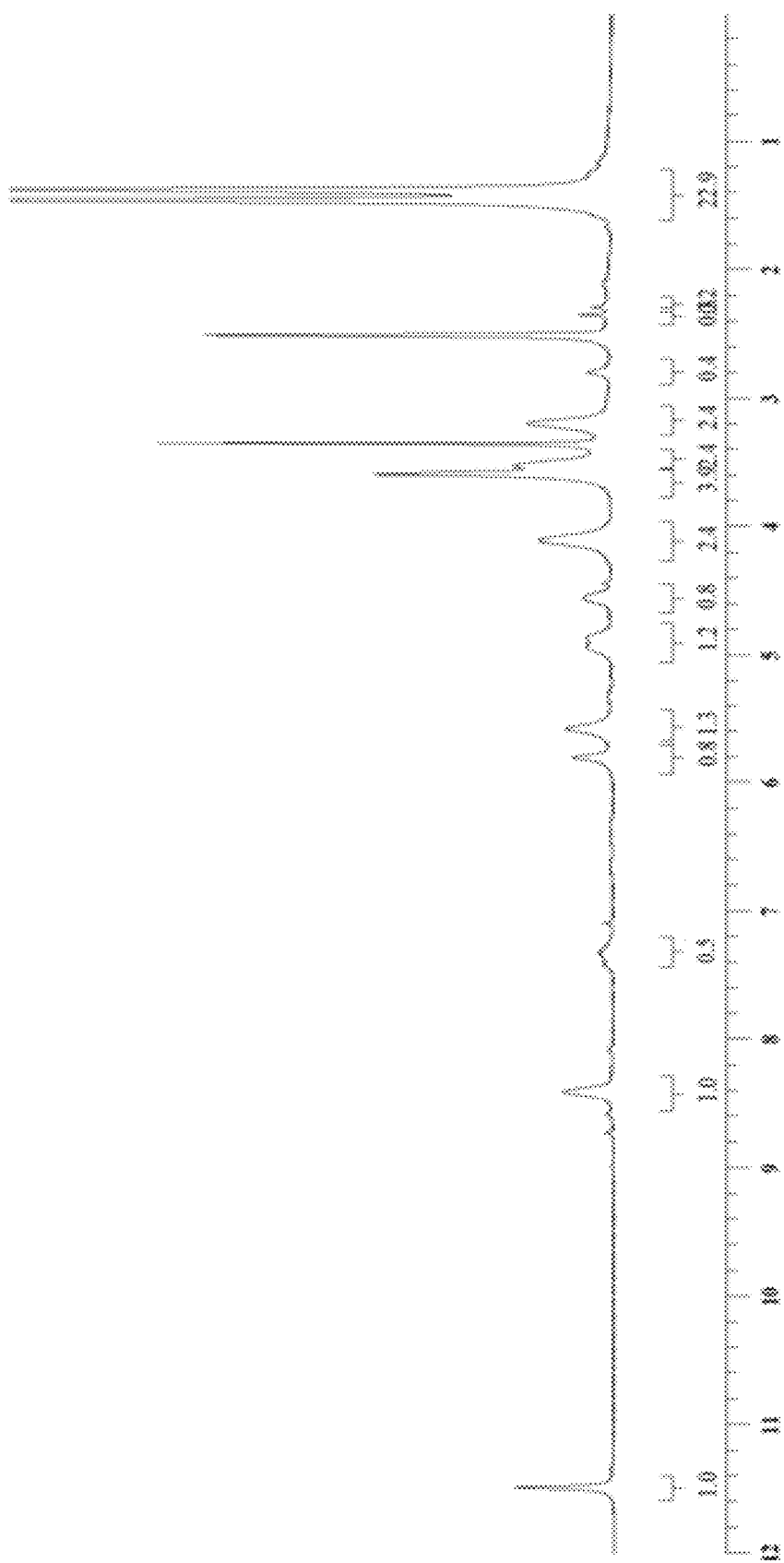
FIG. 15: $^1$H NMR of Polymer 5a, DMSO-d6.
Figure 16:
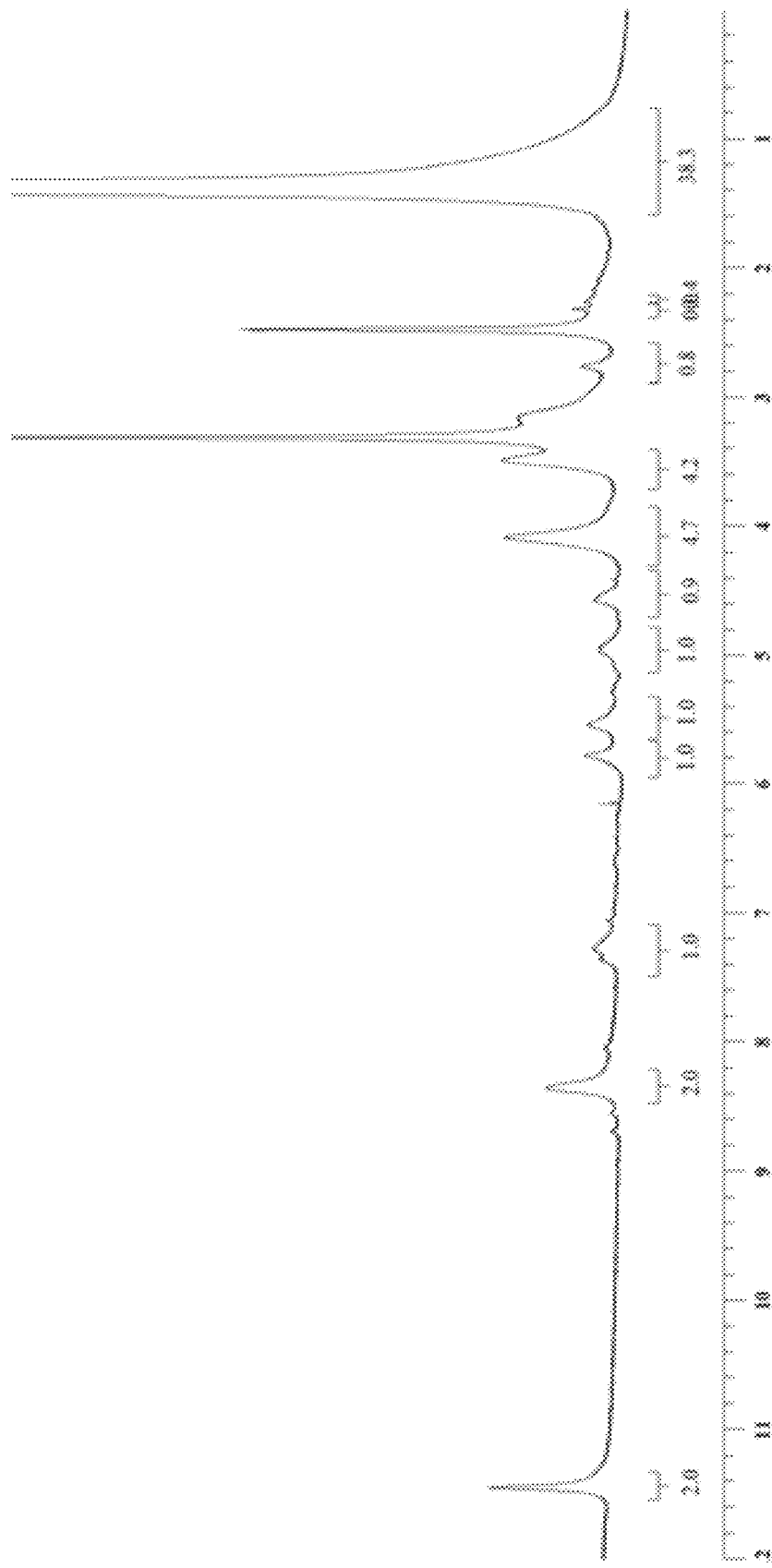
FIG. 16: $^1$H NMR of Polymer 5b, DMSO-d6.
Figure 17:
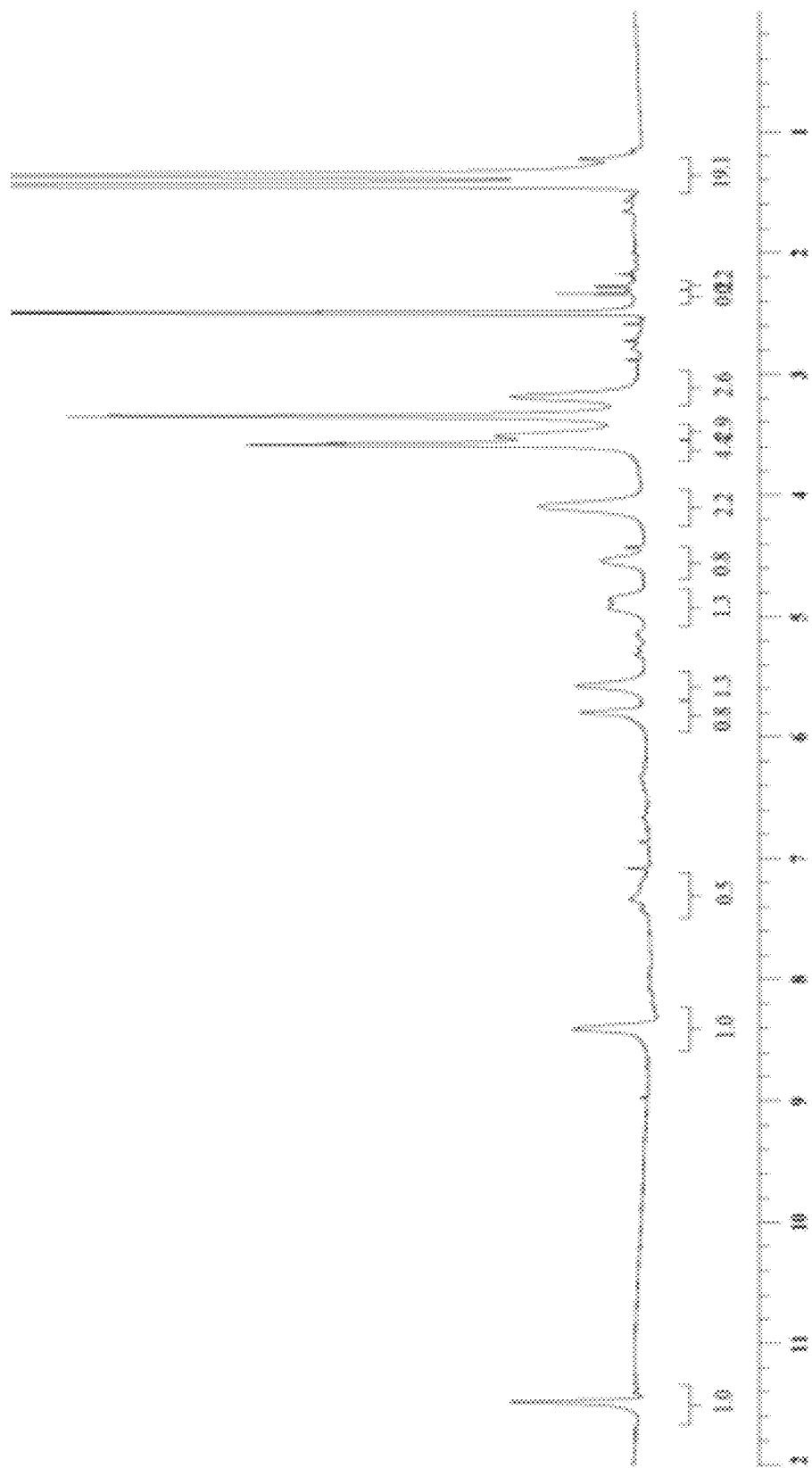
FIG. 17: $^1$H NMR of Polymer 6a, DMSO-d6.
Figure 18:
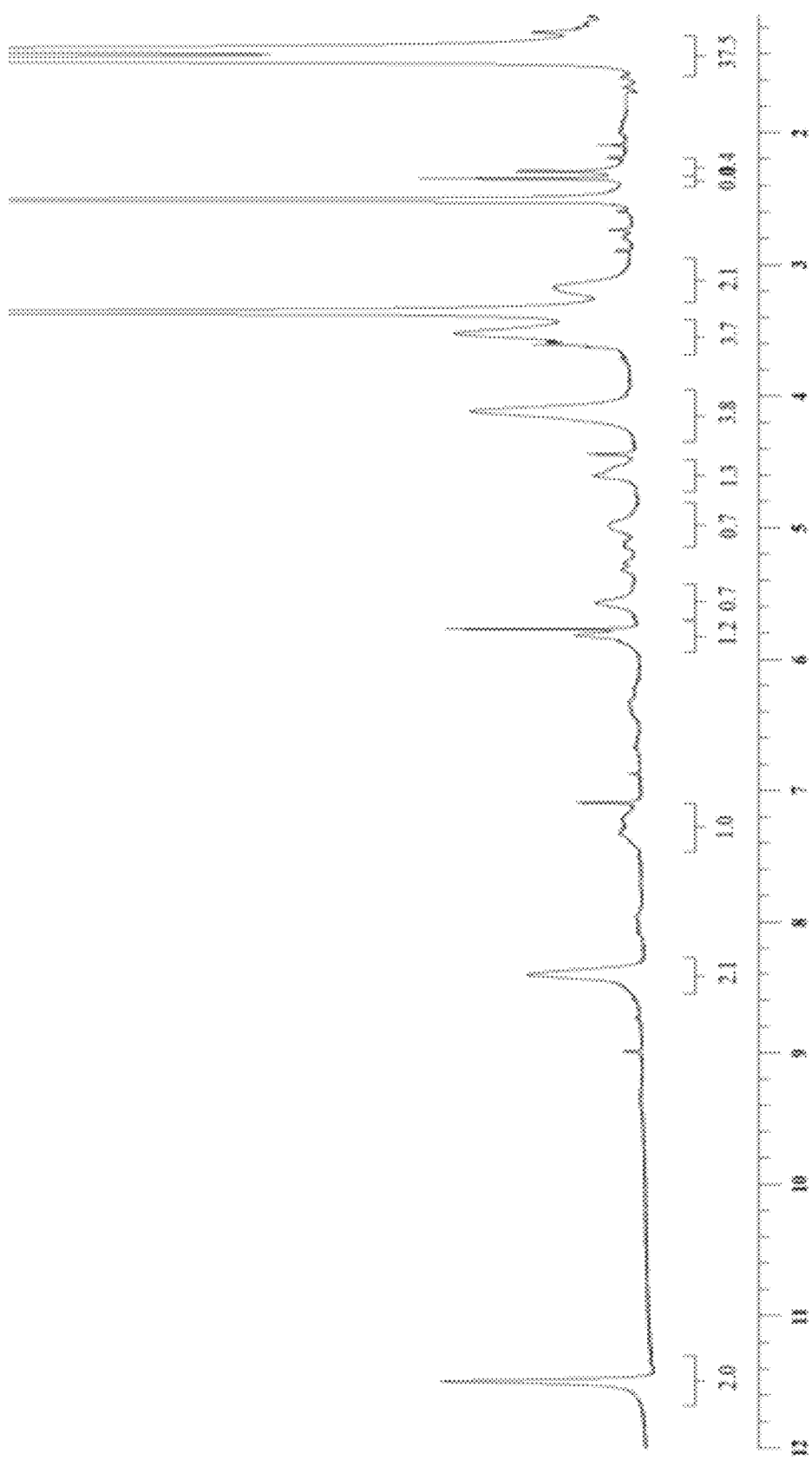
FIG. 18: $^1$H NMR of Polymer 6b, DMSO-d6.
Figure 19:
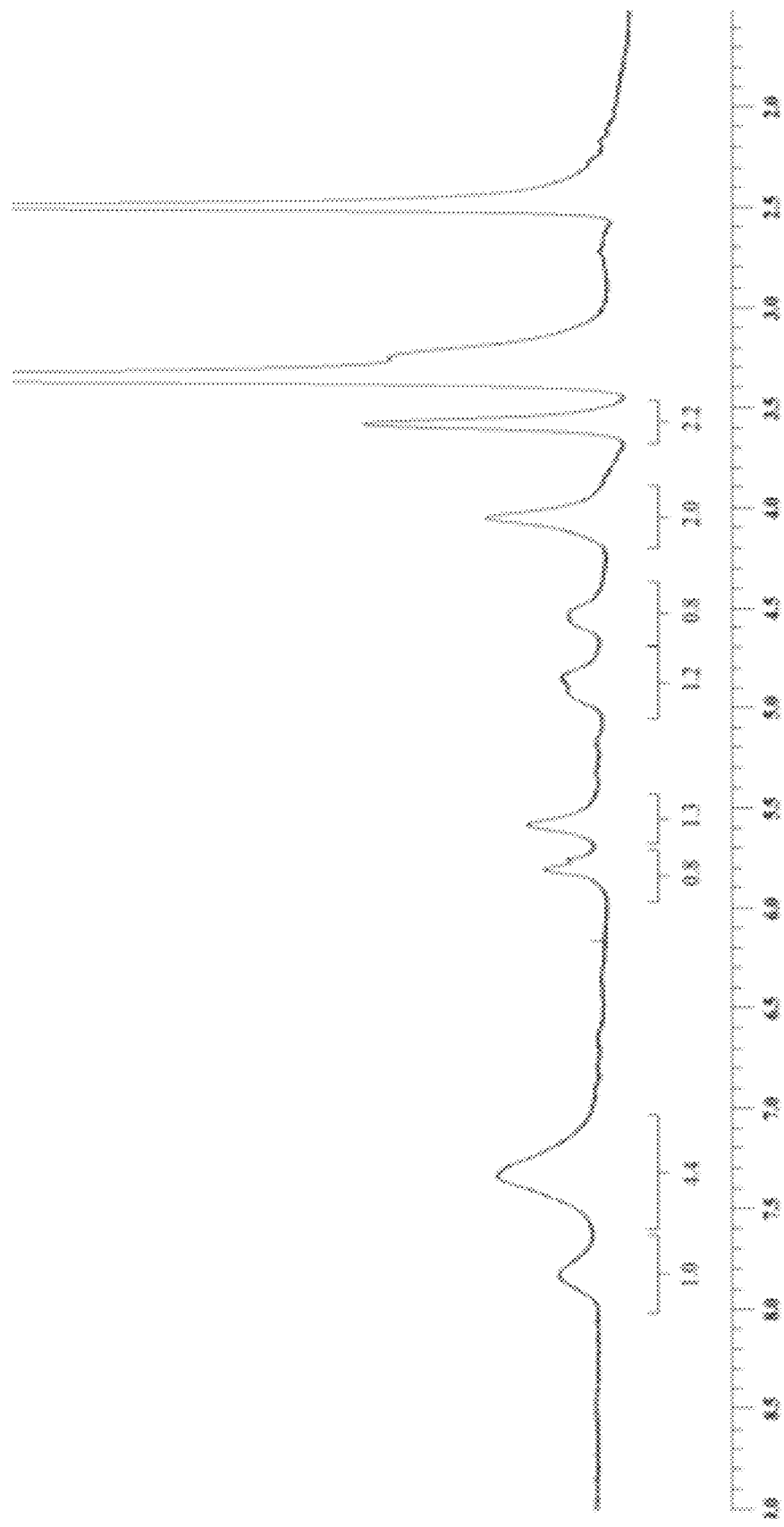
FIG. 19: $^1$H NMR of Polymer 7a, DMSO-d6.
Figure 20:
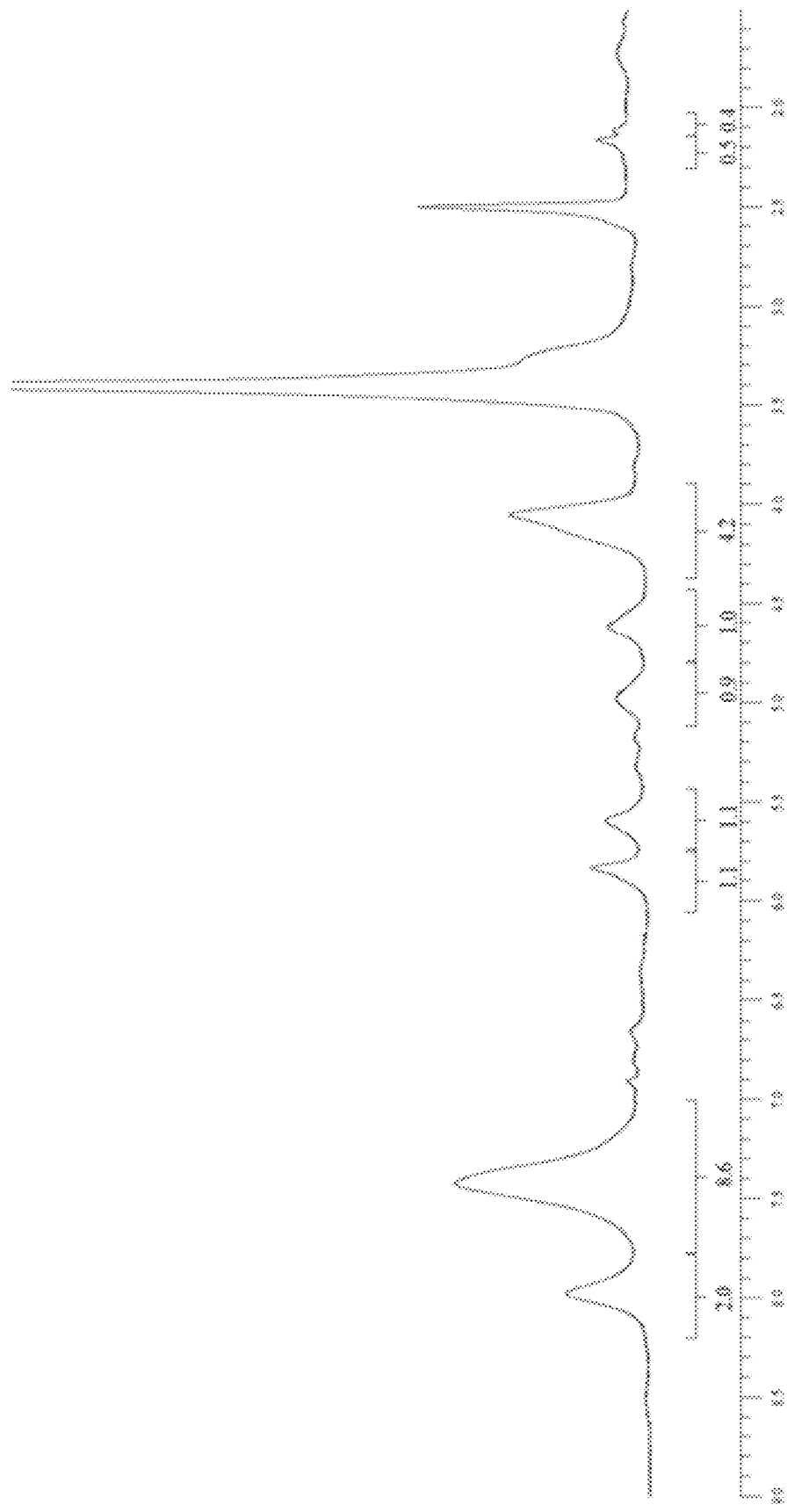
FIG. 20: $^1$H NMR of Polymer 7b, DMSO-d6.
Figure 21:
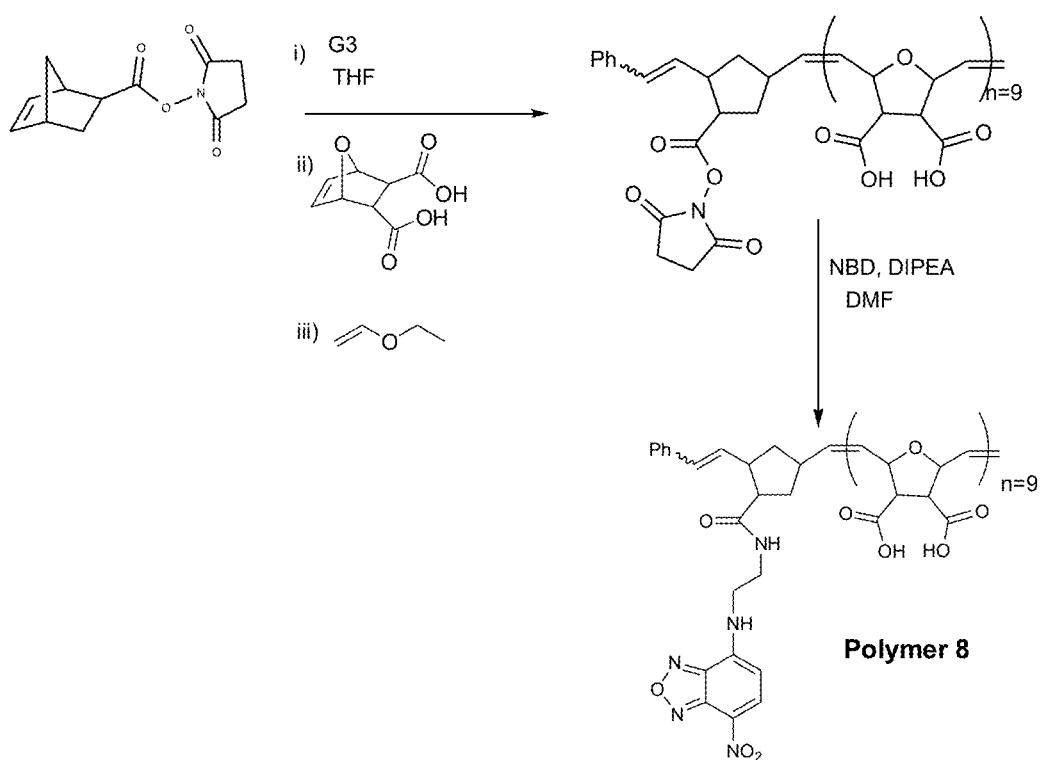
FIG. 21: Synthesis of NBD-labeled polymer 8.
Figure 22:
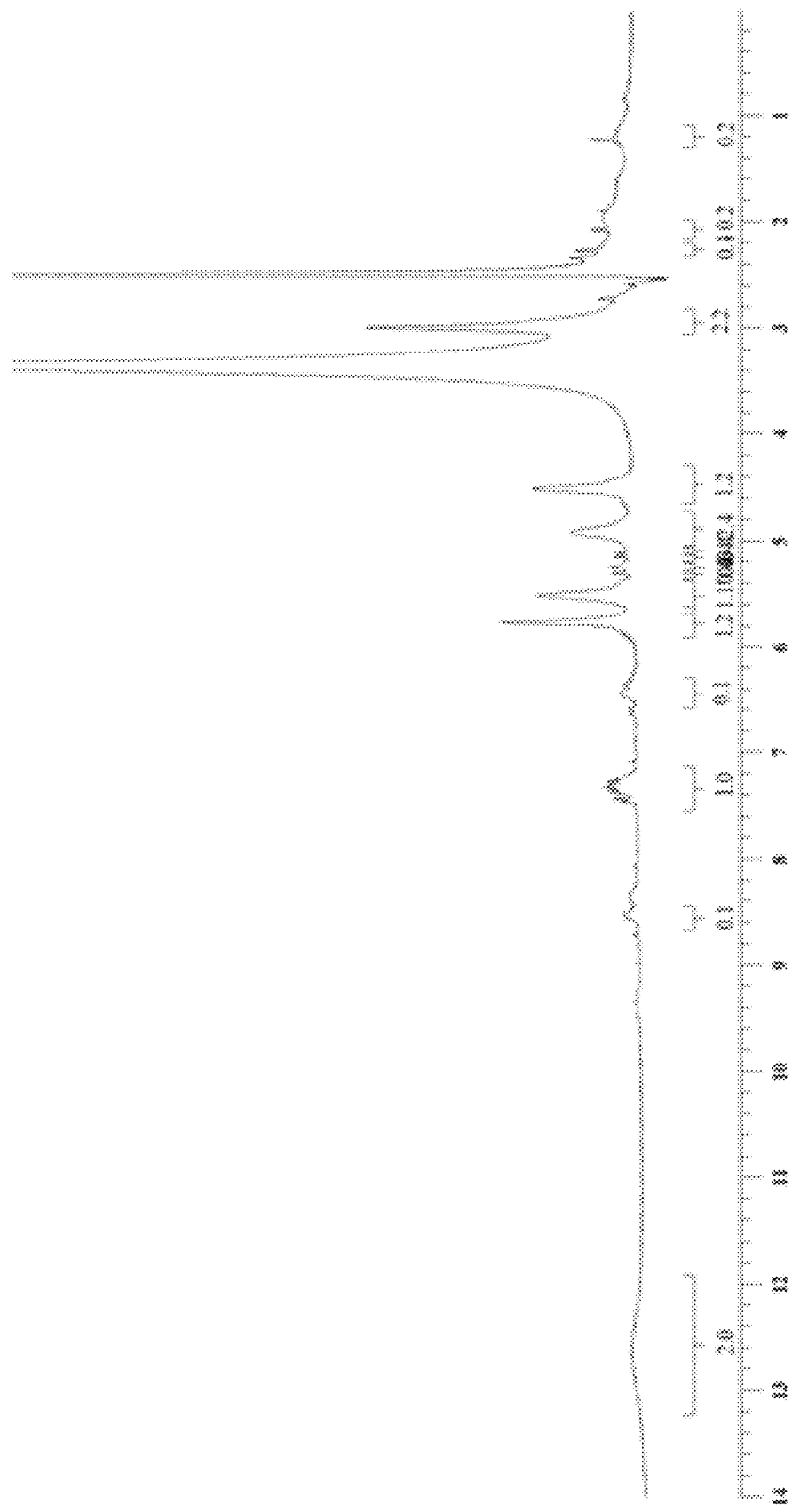
FIG. 22: $^1$H NMR of Polymer 8, DMSO-d6.
Figure 23:
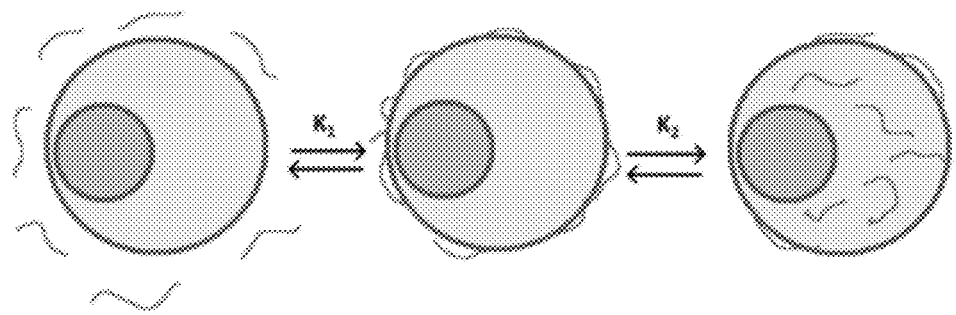
FIG. 23: Schematic representation of PTDM internalization. $K_1$ is the constant for the equilibrium between PTDM in solution and on cell surface, and $K_2$ is the equilibrium coefficient for cell surface binding and internalization processes. Especially, $K_2$ is specific for each molecule, and determines the internalization efficiency for each PTDM.
Figure 24:
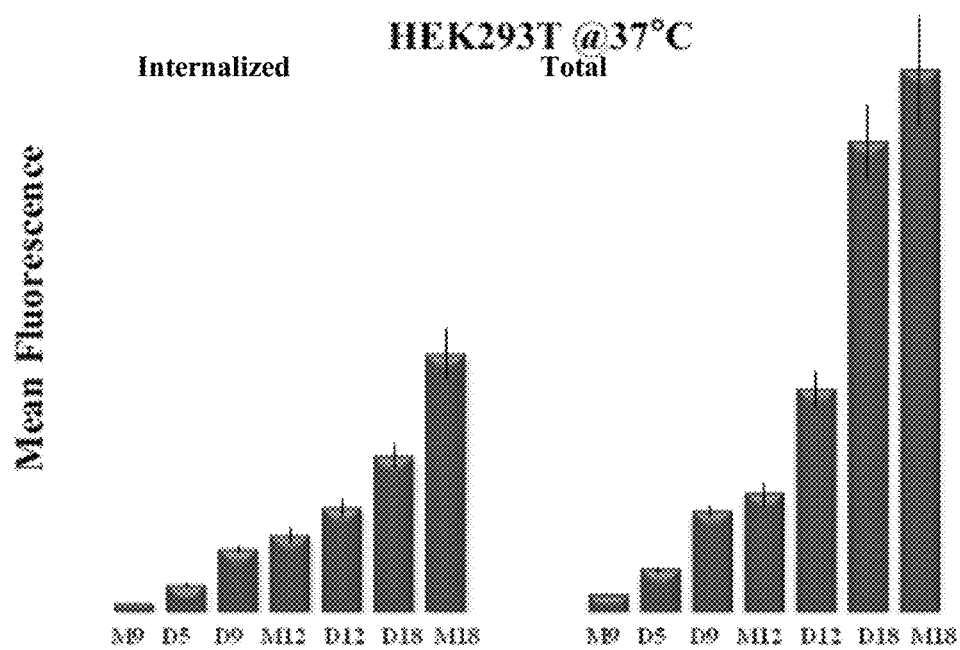
FIG. 24: Cellular uptake of NBD-labeled polymers at 37° C. in HEK293T cells. HEK293T cells were incubated with 5 μM NBD-labeled polymers in complete growth medium with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.
Figure 25:
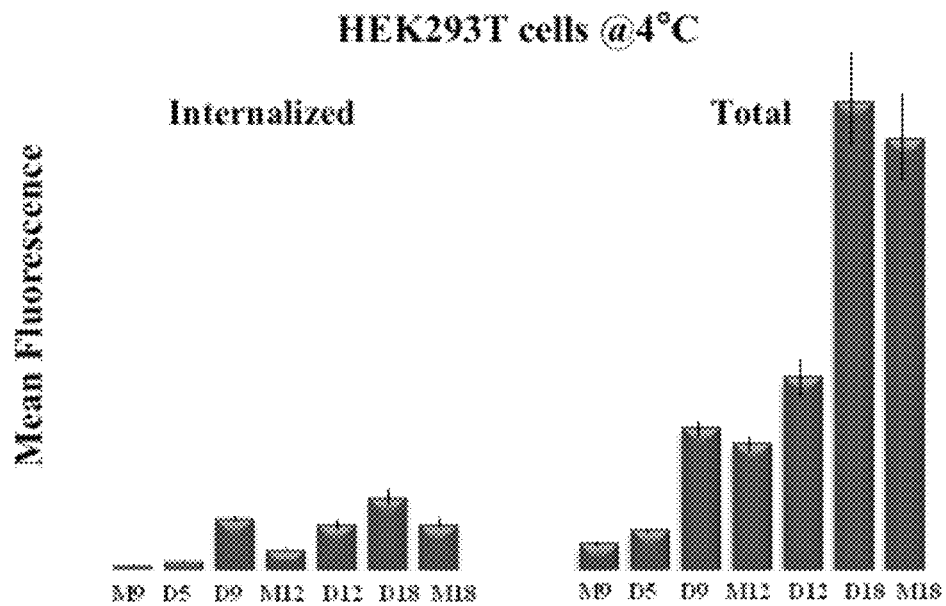
FIG. 25: Cellular uptake of NBD-labeled polymers at 4° C. in HEK293T cells. HEK293T cells were incubated with 5 μM NBD-labeled polymers in complete growth media with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.

Arginine-rich structures are known to translocate across the plasma membrane. It is demonstrated by this invention that it is possible to program synthetic polymers to behave like natural PTDs. Using ROMP, novel sequences were designed to study the structure-activity relationship (SAR) between guanidinium functionalized polymers and cellular internalization in three different cell types. ROMP was chosen because it is well-known to be functional group tolerant, and it is a living polymerization method, which allows the number average degree of polymerization to be narrowly defined and easily controlled. Here, two novel structural classes of new PTDMs were introduced, Mn and Dn. These two structural classes allow the distinction of total charge density, or the total number of guanidinium functions, from molecular length. For example, within the group M9, D5 and D9, one can compare the number of guanidines (M9 vs D5) or the total length (M9 vs D9) (FIG. 5). Specifically, the ability to prepare peptides with the same overall length but twice the functional group density is non-trivial. While cationic sequences can be cytotoxic, 7-AAD assays determined that all the internalization studies were conducted below any concentrations that influenced cell viability.

To better analyze the internalization efficiencies of these PTDMs and their affinities for the cell membrane, fluorescence from cell surface bound molecules was quenched using the established NBD-dithionite assay and data collected both for treated and untreated cells. Percent cellular uptake, the ratio of mean fluorescence intensity per cell from cell populations treated with dithionite (only internalization fluorescence) to cells not treated with dithionite (both internal and surface bound fluorescence) were measured. This highlights the important parameters related to the transport ability of these PTDMs. By examining this percent cellular uptake rather than simply mean fluorescence per cell for each molecule, a more direct measure of internalization efficiency is obtained since the raw data clearly shows that some structures bind to the cellular surface more strongly and as a result the concentration of PTDMs at the surface are proportionally higher.

Figure 3:
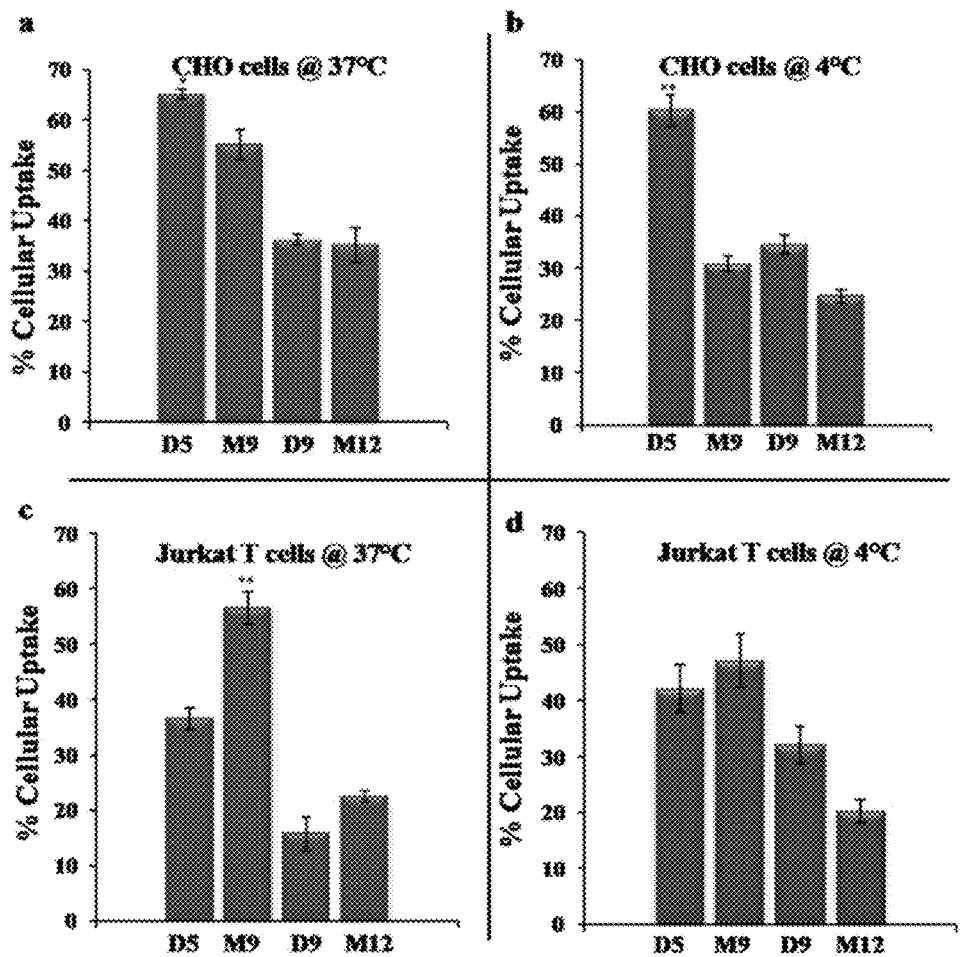
FIG. 3: Percent cellular uptake of NBD-labeled polymers in (a and b) CHO and (c and d) Jurkat T cells at 37° C. and 4° C. CHO cells were incubated with 5 μM NBD-labeled polymers a) at 37° C., *(P<0.05) of D5 versus M9 percent cellular uptake, and b) at 4° C., (P<0.01) of D5 versus M9 percent cellular uptake. Jurkat T cells were treated with 2.5 μM NBD-labeled polymers c) at 37° C., (P<0.01) of M9 versus D5 percent cellular uptake, and d) at 4° C. For the calculation of % internalization, experiments were done with dithionite quenched and without dithionite treated cells and the percent ratio of internalization represents the transduction efficiency of the molecules. Each point is the mean±S.D. of three separate determinations.
Figure 4:
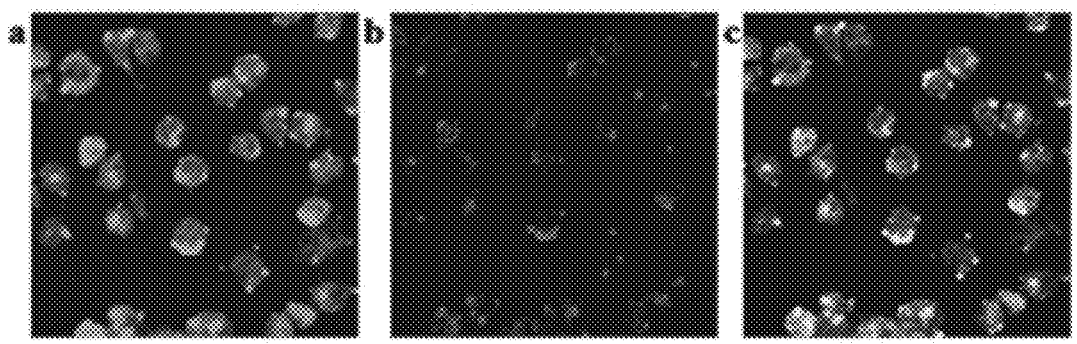
FIG. 4: Localization of D9 polymers in CHO cells. CHO cells were incubated with 5 μM NBD-labeled D9 polymer for 60 min at 37° C., after the last washing step cells were subsequently incubated with Lysotracker red-99 for 4 min, washed, and placed in ice-cold HBSS buffer. a) Localization of D9 molecules (green channel) b) localization of Lysotracker red-99 (red channel), and c) colocalization of D9 molecules and lysotracker (overlay). Note that all cells have a uniform green background demonstrating D9 is present outside of lysosome/endosomes.

The internalization mechanism of arginine rich PTDs has been reported as mainly endocytosis in which the encapsulation in endocytotic vesicles is a major restriction to the use of these peptides in cytosolic-, nuclear-, and organelle-specific delivery. (Cheung, et al. 2009 J. Control Release 137, 2-7; Abes, et al. 2006 J. Control Release 110, 595-604.) In the case of endocytotic pathways, transporter molecules are trapped inside endosomes/lysosomes in an environment with an acidic pH and digestive enzymes that inhibit the capability of transporter molecules to deliver their cargo. To explore the internalization of these novel PTDMs, uptake was examined at 37° C. and 4° C. as well as by microscopy and colocalization with lysotracker red-99. Internalization was generally higher at 37° C. than 4° C., which is consistent with the literature and a reasonable observation since endocytotic pathways would be operative. This is confirmed by the microscopy studies shown in FIG. 4. However, and importantly, significant internalization is observed at 4° C. demonstrating that these novel PTDMs also exploit energy-independent pathways. In the Dn series, percent cellular uptake for CHO and Jurkat T-cells is generally similar at 37° C. and 4° C., indicating these PTDMs efficiently access energy- and temperature-independent pathways (see FIG. 3). It should be noted that in Jurkat T-cells, D9 is twice as efficient at 4° C. compared to 37° C., which highlights the role of polymer chemistry and demonstrates the importance of establishing a SAR. In agreement, the overlaid image in FIG. 4c shows distinct regions of only green emission associated with the presence of PTDMs outside of endosomes. This improved uptake of the Dn PTDMs, especially at 4° C., implies that not only the presence but also the density of guanidine units influences uptake pathways, and that a greater density of guanidine units can optimize internalization via energy- and temperature-independent pathways. The fact that the best in class PTDM varies among cell lines further demonstrates the value of this versatile synthetic platform. (Mueller, et al. 2008 *Bioconj. Chem.* 19, 2363-2374.) For example, examining percent cellular uptake at 37° C. shows that D5 and D9 are better than M9 in HEK293T cells while D5 is better than M9 and D9 in CHO cells but M9 is superior in Jurkat T cells (FIG. 5).

The invention thus enables the design and syntheses of synthetic polymers mimic natural PTDs by introducing the appropriate functionality. These synthetic structures demonstrated superior uptake efficiencies compared to a well-known peptide analogue. Taken together, these synthetic analogs are highly efficient novel transporter molecules with important applications in the delivery of bioactive macromolecules.

EXAMPLES

Synthetic Mimics of Protein Transduction Domains
    Synthesis of PTDMs:
    Monomers for PTDMs were prepared in three steps. The first step was the Diels-Alder reaction of maleic anhydride and furan. In the second step, product from step 1 was reacted with the corresponding alcohol (methanol or 1,3-Di-Boc-2-(2-hydroxyethyl)guanidine) and the reaction was catalyzed by DMAP. Finally, 1,3-Di-Boc-2-(2-hydroxyethyl)guanidine was added to the monomer by EDC coupling (see Supplementary Information for details). Boc-protected guanidinine functionalized monomers were polymerized via Grubb's 3$^{rd}$ generation catalyst (see Supplementary info for details).

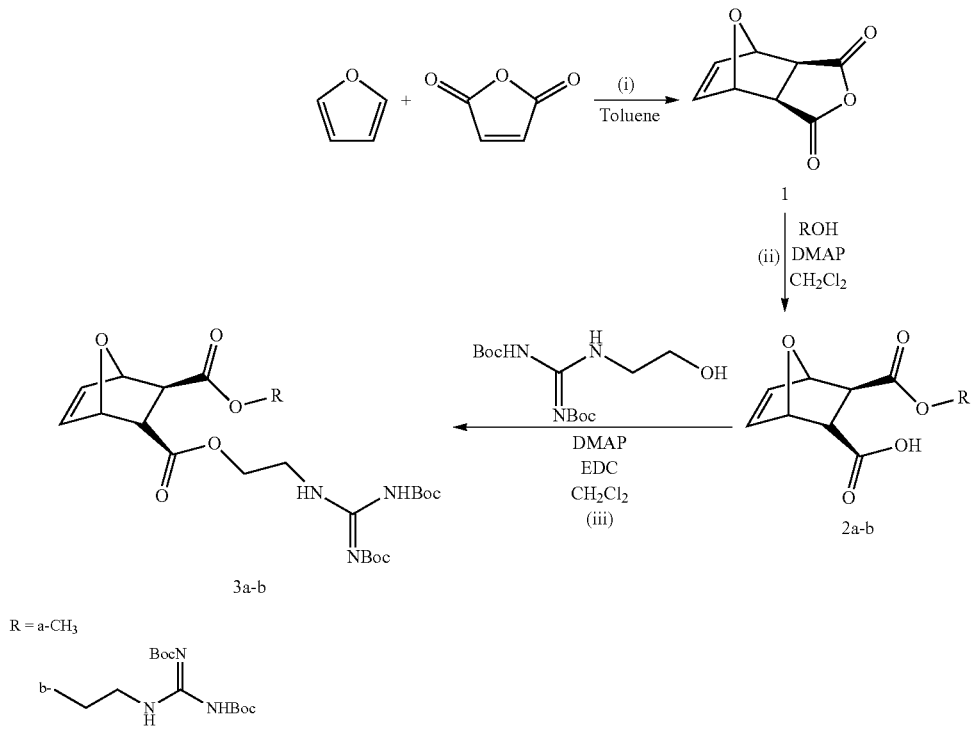

Scheme 1: Monomer Synthesis

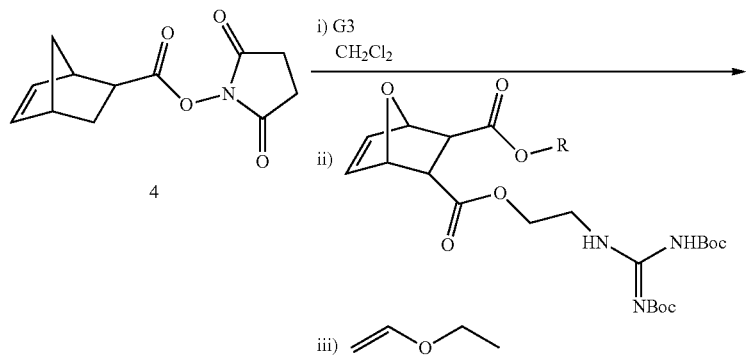

Scheme 2: Dye-labeled Polymer Synthesis

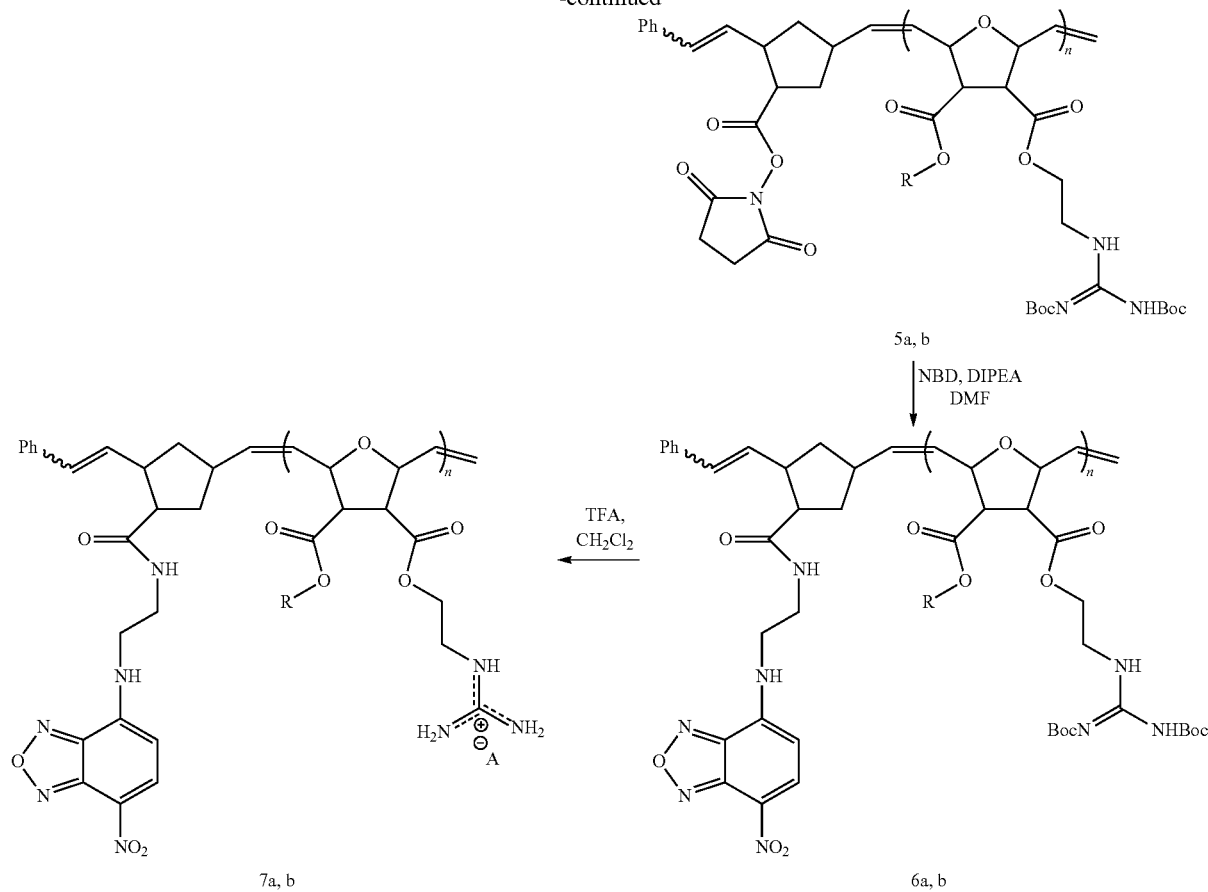
Scheme 3: Block-co-polymer synthesis
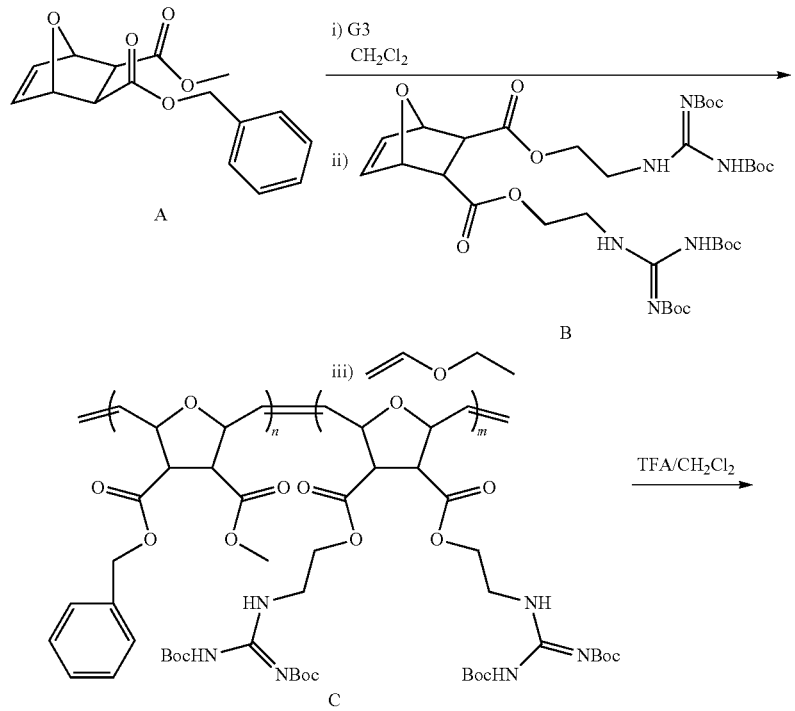

-continued

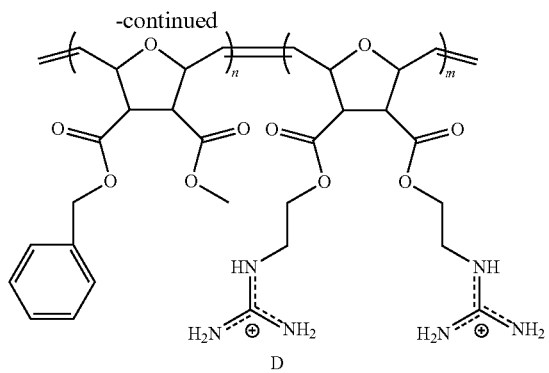

D

Uptake of PTDMs:

HEK293T and CHO cells were treated with 5 μM NBD-labeled PTDMs, and Jurkat T cells were treated with 2.5 μM NBD-labeled PTDMs for 30 min in complete growth medium supplemented with 10% fetal bovine serum. Then, the cellular uptake of the molecules was analyzed by fluorescence activated cell sorter (FACS-BD-LSRII) or confocal microscopy (LSM510-Carl Zeiss, 40× oil immersion objective) (see Supplementary Information for details).

Synthesis of NBD-Labeled Polymers

Di-Boc protected guanidinium functionalized monomers were synthesized in three steps and resulted in ~80% overall yield. This synthetic monomer design allowed us to introduce one guanidinium group, as a direct comparison to R9, or two guanidinium groups, which doubled the functional group density. In order to visualize these PTDMs within cells, they were end-labeled by first ring-opening a succinimide-functionalized activated ester monomer, then adding either the methyl or diguanidinium monomer units. (Roberts, et al. 2004 *Org. Lett.* 63, 253-3255.) Following polymerization, the succinimide ester was exchanged with an ethylenediamine functionalized NBD dye, and the polymers were purified by both dialysis and column chromatography. The labeled polymers were characterized by NMR and UV-capable size exclusion chromatography. Analysis of the Boc-protected polymers yielded the expected molecular weights and narrow polydispersities (PDI~1.06-1.10), which are typical of ROMP due to its living nature. (Choi, et al. 2003 *Angew. Chem. Int. Ed.* 42, 1743-1746.) In the last step, the Boc groups were removed using trifluoroacetic acid in dichloromethane. The final products were purified by dialysis and recovered by lyophilization. Though, ester groups present in the polymers could undergo hydrolysis, this would be unexpected, as the time scale of these in vitro experiments is short (~30 mins) compared to the room temperature stability in buffer (PBS, pH 7.2) (>2 weeks) so hydrolysis in the presence of cells has therefore not been investigated Cellular Uptake Assays To avoid artifacts from the cellular uptake experiments, several precautions were taken. Early studies on PTDs documented artifacts that result from cells being fixed prior to quantification. (Thoren, et al. 2003 *Biochem. Biophys. Res. Comm.* 307, 100-107.) Therefore, cell fixation, which is unnecessary, was not used. Further, in order to measure only the fluorescence from internalized molecules, the NBD-dithionite assay was employed to quench any cell surface bound fraction remaining after the last washing step. (Drin, et al. 2003 *J Biol. Chem.*, 278, 31192-31201.) After quenching the cell surface bound molecules, NBD-labeled molecules were detected in more than 80% of the cells at 5 μM, as shown in FIG. 2a by a representative FACS histogram. The relative internalization efficiency of NBD-labeled molecules was demonstrated using both the mean fluorescence per cell and percent cellular uptake. FIG. 2b shows the impact of Dn polymer length comparing the mean fluorescence between cell associated (prior to dithionite treatment, open bars) and internalized molecules (following surface bound NBD quenching, closed bars).

As the PTDM length increased, the number of both internalized and cell surface bound molecules increased. For example, D18 is twice as long as D9, and D18 is two-fold more efficient than D9 in terms of the internalized fluorescence intensity. On the other hand, there is a 10-fold increase in the cell surface bound fraction, indicating that D18 interacts with the cell surface much more strongly than D9, but it is not internalized as efficiently. The mean fluorescence intensity of internalized molecules provides information regarding uptake of molecules, however more information is needed to develop a detailed SAR for PTDMs that efficiently cross the plasma membrane.

In the simplest form of this process (ignoring biological processes like endocytosis), there are at least two important, yet different, equilibrium constants that need to be considered: ratio of PTDM in solution to cell surface bound PTDM and ratio of cell surface bound PTDM to internalized PTDM. Because of interest in the second process, the data has been normalized as the percent cellular uptake, which is the percent ratio of internalized molecules (following dithionite treatment) to total cell associated molecules (before dithionite treatment). This ratio is conceptually demonstrated in FIG. 2b by the solid red bars and open red bars for each PTDM. This normalized value then allows direct comparisons among all PTDMs and across all cell types to be made. This method was chosen to present the data because this ratio is a more accurate way to understand the internalization efficiency of each PTDM, and because it separates internalization from cell surface binding affinity. This would be unnecessary if every molecule had the same affinity for the cell surface, but as shown by the mean fluorescence data, this is not true. As a result, despite the identical concentrations in solution, the concentration at the cell surface varies with molecular structure and cell type. Therefore, the figures after FIG. 2b report the percent cellular uptake, focusing on the PTDMs that are the most efficient at crossing the membrane.

Initially, the PTDMs Mn and Dn, with various molecular weights, were evaluated for uptake in HEK293T cells (FIG.

2) along with the control R9. These data clearly demonstrate that the methyl- and di-guanidinium polymers were able to function as PTDMs and, in fact, showed greater internalization efficiency than the thoroughly studied control R9. (Mitchell, et al. 2000 *J. Peptide Res.*, 56, 318-325; Futaki, et al. 2001 *J Biol. Chem.* 276, 5836-5840; Wender, et al. 2000 *Proc. Natl. Acad. Sci. USA* 97, 13003-13008.) Within the Mn series, the maximum efficiency was observed with 12 repeat units (M12) when compared to 9 (M9) and 18 (M18) (FIG. 2d). On the other hand, in the Dn series, which has double the number of guanidinium groups compared to the Mn series, the most efficient PTDMs have lengths of 5 and 9 repeat units (D5 and D9, respectively) (FIG. 2f). The fact that D5, D9, and M12 show similar internalization efficiencies suggests that the number of guanidinium groups is not the only factor affecting cellular uptake, and that the density of guanidinium groups also plays an important role. Experiments were also conducted at 4° C. (FIGS. 2c and 2e) to inhibit energy-dependent pathways. Experiments at 37° C. showed that the guanidinium density affects the internalization and the experiments at 4° C. demonstrated this even more clearly. As shown in FIGS. 2c and 2e, at lower temperature, Dn molecules are much more efficient than their Mn analogues. For example, D9 showed 35% cellular uptake compared to 10% for M18, although the total number of guanidinium groups is the same. Among all the PTDMs, D9 showed superior uptake at 4° C., making it the most favorable molecule for internalization by non-endocytotic pathways (FIG. 2e).

Figure 30:
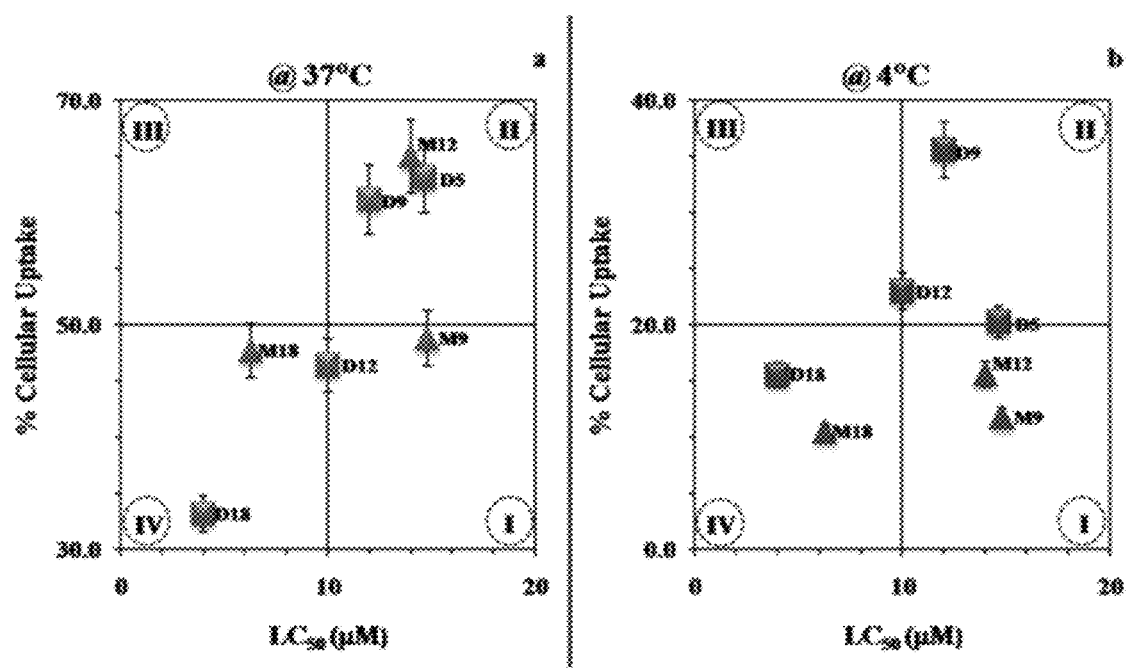
FIG. 30: Percent cellular uptake vs toxicity HEK293T cells. Mn (triangles) and Dn (squares) polymers were plotted % cellular uptake against toxicity of polymers at both a) 37° C. and b) 4° C. The concentrations for toxicity of polymers were reported as lethal concentrations ($LC_{50}$) at which half members of the tested population of cells were detected as damaged and/or dead. Each plot was divided into four quadrants to specify molecules' efficiency as a function of percent cellular uptake and toxicity, quandrants II and upper parts of I represent the most efficient molecules with high cellular uptake and low toxicity. Each point is the mean±S.D. of three separate determinations.
Figure 31:
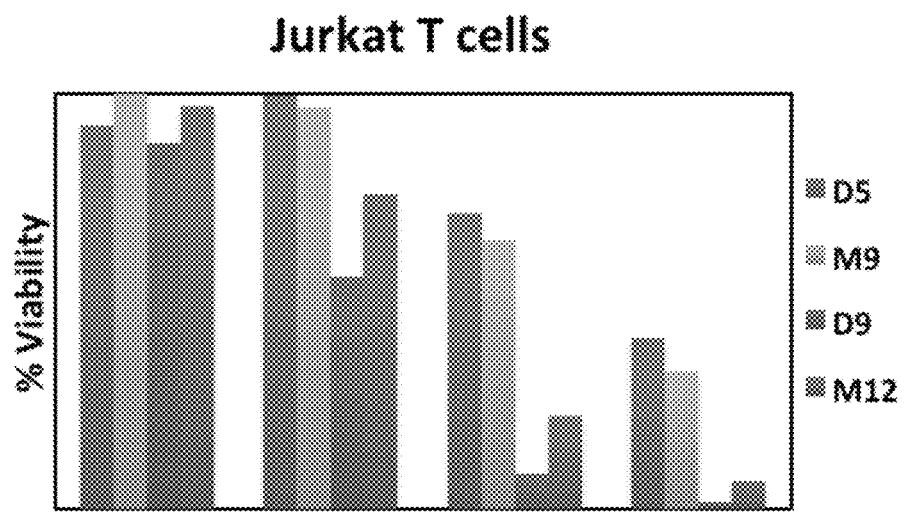
FIG. 31: Cytotoxicity in Jurkat T cells. 7-AAD viability assay was used to determine the cytotoxicity of the polymers.
Figure 32:
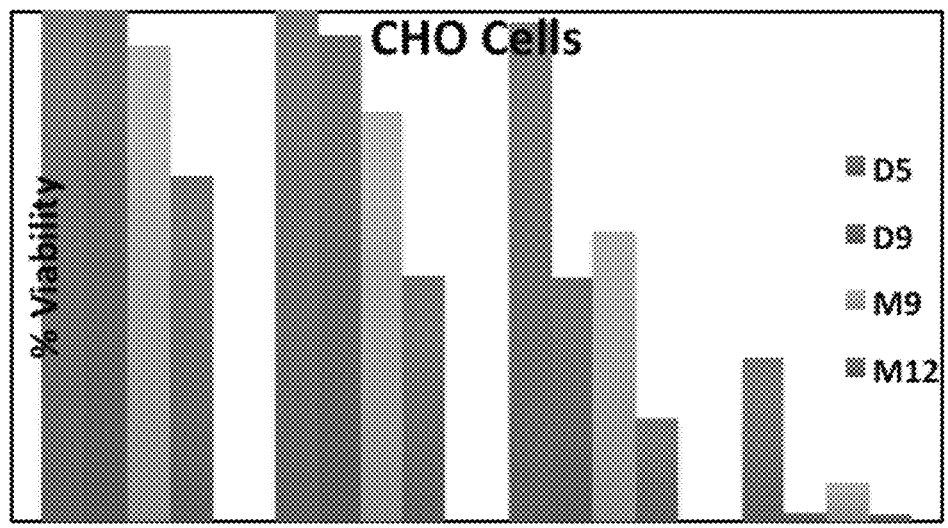
FIG. 32: Cytotoxicity in CHO cells. 7-AAD viability assay was used to determine the cytotoxicity of the polymers.

In addition to cellular uptake experiments at 37° C. and 4° C., cytotoxicity testing was also performed using 7-aminoactinomycin D (7-AAD) viability dye to determine lethal concentrations ($LC_{50}$). To build a structure-activity relationship, plots were made of percent cellular uptake vs. $LC_{50}$ and the graph was divided into four quadrants (FIG. 30). Optimal PTDMs would be those structures with high internalization efficacy and high $LC_{50}$ values, or low toxicity (quadrant II). All the molecules in quadrants I and II in FIGS. 30a and 30b were considered promising PTDMs for further study since they showed both low toxicity and good cellular uptake. In addition, all of the PTDMs reported here showed no toxicity in the working concentration range.

To expand the cell types examined, the PTDMs specified as most effective in HEK293T cells were evaluated for internalization in both CHO and Jurkat T cells. FIG. 3a shows that in CHO cells, the shorter PTDMs, D5 and M9 were more efficient than their longer analogs, D9 and M12. D9 and M12 were found to adsorb more strongly on the cell membrane, but their ability to enter the cells was limited with internalization efficiencies near 35%, compared to M9 and D5 which had efficiencies of 55% and 65%, respectively. PDTM D5 demonstrated remarkable uptake in this cell type at both high and low temperatures, in contrast to its low uptake in HEK293T cells. The addition of eight more guanidinium groups (in the case of D9) did not increase the uptake in CHO cells at 37° C. nor 4° C. but, in fact, reduced the percent of internalized molecules while enhancing the cell surface binding compared to D5. Furthermore, M9 and D5 have essentially the same number of guanidinium groups and exhibited similar uptake characteristics at 37° C. (FIG. 3a). Nevertheless, D5 remained the best in class with a slightly higher internalization percentage at 37° C. and a significantly higher internalization percentage at 4° C. (60% vs. 30%). Similar to the observations with the HEK293T cells, the Dn-series PTDMs entered CHO cells more efficiently at 4° C. than the Mn-series.

Figure 26:
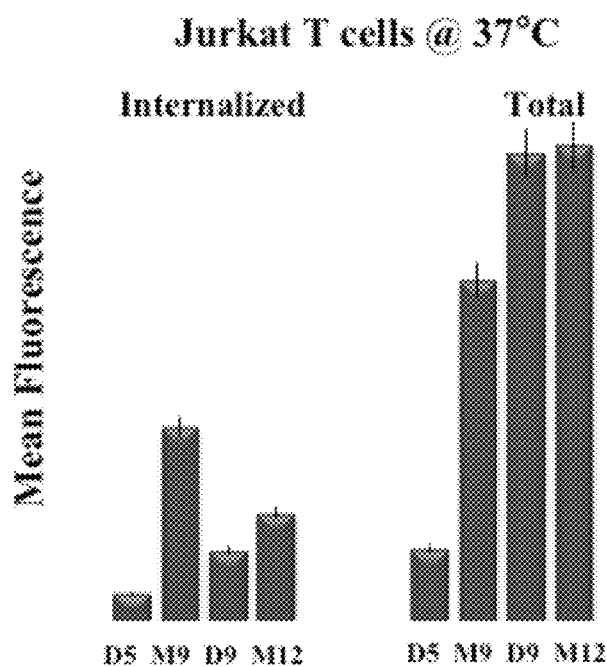
FIG. 26: Cellular Uptake of NBD-labeled polymers at 37° C. in Jurkat T cells. Jurkat T cells were incubated with 2.5 μM NBD-labeled polymers in complete growth media with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.
Figure 27:
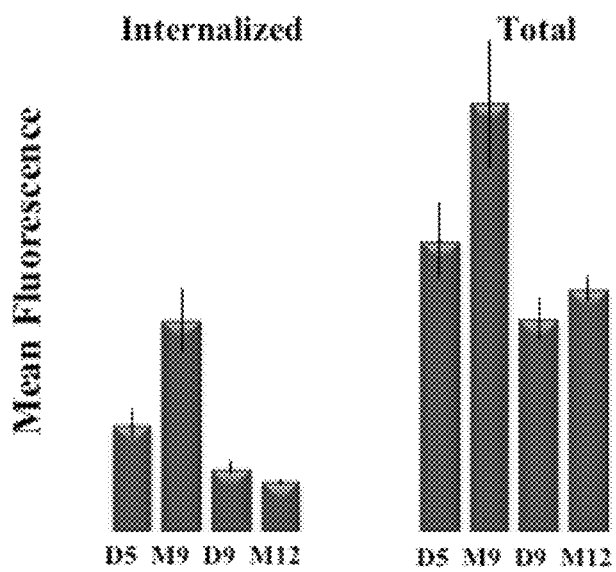
FIG. 27: Cellular Uptake of NBD labeled polymers at 4° C. in Jurkat T cells. Jurkat T cells were incubated with 2.5 μM NBD-labeled polymers in complete growth media with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.
Figure 28:
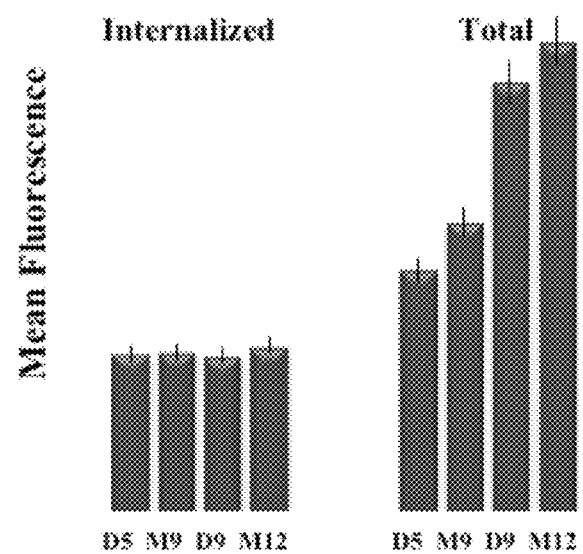
FIG. 28: Cellular Uptake of NBD-labeled polymers at 37° C. in CHO cells. CHO cells were incubated with 5 μM NBD-labeled polymers in complete media with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.
Figure 29:
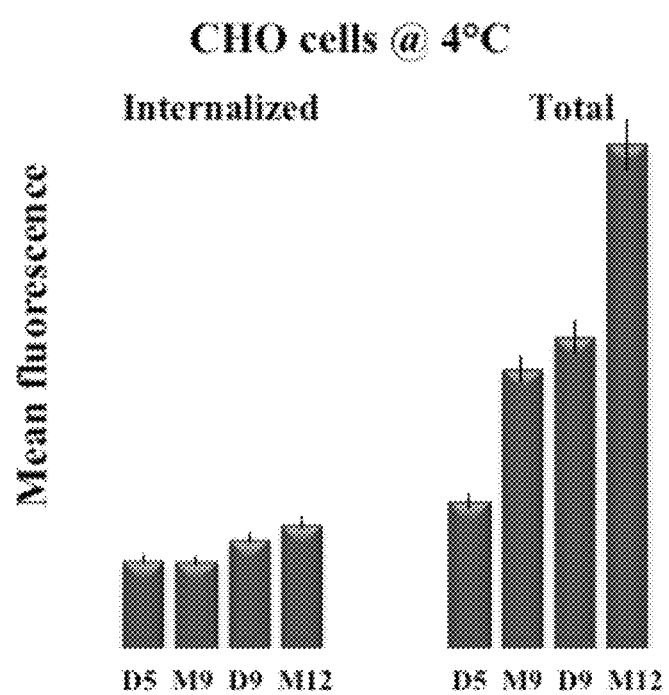
FIG. 29: Cellular Uptake of NBD-labeled polymers at 4° C. in CHO cells. CHO cells were incubated with 5 μM NBD-labeled polymers in complete growth media with 10% serum, then washed and resuspended in CBE buffer for FACS analysis and as a last step treated with NBD-dithionite quenching assay. Bars labeled as internalized represent mean fluorescence after dithionite treatment and total stands for mean fluorescence before dithionite treatment. Each point is the mean±S.D. of three separate determinations.

Jurkat T cells were found to be more sensitive to changes in the density of guanidinium group and the chain length. For example, D9 and M12 demonstrated considerable toxicity, even at low concentrations like 5 μM. As a result, and in contrast to the other cell studies, all of the uptake studies with these suspension cells were performed at a lower concentration of 2.5 μM. The shorter sequences, D5 and M9, remained more efficient, showing better uptake profiles at both high and low temperatures (FIGS. 3c and d), while D9 and M12 showed a high affinity for the cell surface (FIGS. 26 and 27). In this T cell line, M9 exhibited outstanding uptake at 37° C. (60%), which was slightly diminished at 4° C. (50%) yet still comparable to D5. The importance of increased guanidinium density (Dn vs. Mn) is emphasized at 4° C. as the percent cellular uptake of D5 remained 40% at both 37° C. and 4° C., while the uptake of M9 decreased from 60% to 50% upon reducing the temperature. D9 was more efficient at 4° C. than at 37° C. (32% vs. 16%), showing the importance of guanidinium density on the energy-independent internalization pathway.

Although the detailed mechanism of cellular internalization is beyond the scope of this paper, some insight into the cellular location of these PTDMs is warranted. The internalization efficiency at 37° C. compared to 4° C. implies that energy-independent mechanisms are operative with these novel, synthetic PTDMs. To further explore their internalization, the presence of D9 in CHO cells was visualized using confocal microscopy. As shown in FIG. 4a, all of the cells within the field contain significant green fluorescence from the NBD labeled PTDM. Simultaneously, LysoTracker® Red DND-99 was employed to stain endosomic vesicles present in these CHO cells as shown in FIG. 4b and the overlaid image (FIG. 4c) shows yellow areas where D9 and LysoTracker® Red DND-99 are colocalized in the endosomes/lysosomes. FIG. 4c also shows uniform diffuse green cytoplasmic staining within the cell, indicating the presence of D9 outside of endosomic vesicles.

Experimental

General

Maleic anhydride, furan, 4-dimethyl aminopyridine (DMAP), 1-(3-Dimethylaminopropyl)-3-ethylcarbodiimide hydrochloride (EDC), methanol, 1,3-Di-Boc-2-(2-hydroxyethyl)guanidine, anhydrous dimethylformamide (DMF), di-isopropyl ethyl amine (DIPEA), ethylvinyl ether and trifluoroacetic acid (TFA) were obtained as reagent grade from Aldrich, Fluka or Acros and used as received.

$3^{rd}$ generation Grubbs catalyst (Dichloro-di(3-bromopyridino)-N,N'-Dimesitylenoimidazolino-Ru=CHPh; G3) was synthesized as described previously by Grubbs et al. (Love, et al. 2002 *Angew. Chem. Int. Ed.* 41, 4035-4037.) The HPLC grade solvents ethyl acetate, pentane and hexane were purchased from Aldrich, Fisher Scientific or Acros and used as received. Tetrahydrofuran (THF) (HPLC grade, Fisher Scientific) was distilled from sodium/benzophenone under nitrogen. Dichloromethane (DCM) (HPLC grade, Fisher Scientific) was distilled from $CaH_2$ under nitrogen.

Gel permeation chromatography (THF, calibrated with polystyrene standards, toluene as flow marker, 50° C.) was measured on a PL50 GPC setup (Polymer Laboratories, Amherst, Mass.) with a PL Gel 5 μm pre-column and two 10 μm analytical Mixed-D columns (Polymer Laboratories, Amherst, Mass.). NMR spectra were recorded on a Bruker DPX300 spectrometer (Bruker, Madison, Wis.). High resolution mass spectra were obtained from a JEOL JMS 700 instrument (JEOL, Peabody, Mass.); Matrix Assisted Laser Desorption and Ionization Time of Flight Mass Spectra (MALDI-TOF MS) were measured on a Bruker Daltonics Reflex III (Bruker, Madison, Wis.).

Monomer Synthesis

Synthesis of 3a: (i) Maleic anhydride (100 g, 1.02 mol) was dissolved in 1 L toluene. 150 mL (140.7 g, 2.05 mol) furan was added, and then the solution was stirred for 3 days according to the literature. The crude product (1) was then filtered, washed with hexanes and dried under vacuum. A colorless powder was obtained. Spectroscopic data and yield are the same as reported earlier. (Mantovani, et. al. 2005 *J. Am. Chem. Soc.* 127, 2966-2973.) (ii) The same procedure was followed as Lienkamp et. al. with minor modifications. Compound 1 and 2 equivalents of the methanol were dissolved in DCM and the reaction mixture was stirred overnight after the addition of 10 mol % DMAP. After the completion of reaction, the solvent was removed by vacuum evaporation at room temperature. The unreacted alcohol was removed by a dynamic vacuum ($5 \cdot 10^{-2}$ mbar). Crystallization from DCM/hexanes yielded product (2a). Spectroscopic data and yields matched those reported earlier. (Lienkamp, et al. 2008 *J. Am. Chem. Soc.* 130, 9836-9843.) (iii) 1 equivalent of compound 2a, 0.9 equivalents of 1, 3-Di-Boc-2-(2-hydroxyethyl)guanidine and 10 mol % of DMAP were dissolved in DCM, then the solution was cooled to 0° C. and 1 equivalent of EDC was added, and the solution was stirred over night. The reaction mixture was diluted in DCM and washed with 10% $KHSO_4$ (3×25 mL) and sat. $NaHCO_3$ solution (3×25 mL). Next, the organic phase was dried over $Na_2SO_4$ and filtered. The volume of solution was reduced by vacuum evaporation, and the product was run through a short alumina column. Vacuum evaporation of the solvent yielded the pure product 3a. The yield ranged from ~70%.

Synthesis of 3b: Compound 1 and 1.9 equivalents of the respective alcohol were dissolved in DCM, and the reaction mixture was stirred overnight after the addition of 10 mol % DMAP. After all components were dissolved, the solution was cooled down to 0° C. in an ice bath, and 1 equivalent of EDC was added. The solution was stirred over night. The reaction mixture was diluted in DCM and washed with 10% $KHSO_4$ (3×25 mL) and sat. $NaHCO_3$ solution (3×25 mL). Next the organic phase was dried over $Na_2SO_4$ and filtered. The volume of solution was reduced by vacuum evaporation, and the product was run through a short alumina column. Vacuum evaporation of the solvent yielded the pure product 3b. The yield ranged from ~80%.

3a: R=methyl: colorless solid. $^1$H-NMR (300 MHz, $CDCl_3$): $\delta$=11.50 (1H, s), 8.55 (1H, s), 6.46 (2H, s), 5.3 (2H, d, J=6.0 Hz), 4.25 (2H, m), 3.72 (5H, m), 2.84 (2H, s), 1.49 (18H, s). $^{13}$C-NMR (75 MHz, $CDCl_3$): $\delta$=171.7, 171.5, 163.4, 156.3, 153.1, 136.6, 83.2, 80.7, 80.6, 79.4, 63.5, 52.4, 47.1, 46.6, 39.4, 28.3, 28.1. HR-MS (FAB): calc. 483.22, found 484.23.

3b: R=1,3-Di-Boc-2-ethyl guanidine: colorless solid. $^1$H-NMR (300 MHz, $CDCl_3$): $\delta$=11.50 (2H, s), 8.55 (2H, s), 6.42 (2H, s), 5.3 (2H, s), 4.26 (4H, m), 3.71 (4H, m), 2.85 (2H, s), 1.49 (36H, s). $^{13}$C-NMR (75 MHz, $CDCl_3$): $\delta$=171.3, 163.4, 156.3, 153.1, 136.7, 83.2, 80.9, 63.6, 46.7, 39.4, 28.3, 28.2, HR-MS (FAB): calc. 754.37, found 755.3.

Synthesis of NBD-Labeled Compound 4

NBD-ethyl amine molecule was synthesized as described earlier[S4]. A known amount of compound 4 and NBD-ethylenediamine were dissolved in 1 mL anhydrous DMF; then DIPEA (1 eq.) was added and stirred overnight in the dark. DMF was removed (via dynamic vacuum). Product was further purified by filtering through a silica column.

NBD-Labeled 4: orange colored solid. $^1$H-NMR (300 MHz, DMSO-d6): $\delta$=8.00 (1H, m), 7.68 (1H, d, J=10.2 Hz), 6.11 (2H, s), 5.91 (1H, d, J=10.2 Hz), 3.87 (1H, m), 3.47 (2H, d, J=6.0 Hz), 2.79 (2H, d, J=16.5 Hz), 2.03 (1H, m), 1.76 (1H, m), 1.66 (1H, d, J=7.8 Hz), 1.14 (2H, m).

Polymer Synthesis

Known amounts of monomer 4 and G3-catalyst were dissolved in DCM in different shlenk tubes, and each was subjected to three freeze-thaw cycles. Then, the monomer was added in one shot to the vigorously stirring catalyst solution at 0° C. After 20 min, second monomer 3a or 3b was added into the reaction mixture at room temperature and stirred for 90 min. Then, living polymer chain was end-capped by an excess of ethylvinyl ether. After stirring for 120 min, the solution was added drop-wise to 50 mL of stirring pentane to precipitate the polymer. The pentane solution was stirred for an additional 15 min and left standing unperturbed for an hour at 0° C. Then, the precipitate was collected by a fine sinter funnel to yield products 5a-b.

TABLE 1

Molecular Weight Characterization by GPC

| Polymer | Monomer 3 | N repeat units | Mn by GPC | PDI |
| --- | --- | --- | --- | --- |
| M9 | methyl-guanidine | 9 | 4600 | 1.06 |
| M12 | methyl-guanidine | 12 | 6100 | 1.06 |
| M18 | methyl-guanidine | 18 | 8900 | 1.09 |
| D5 | di-guanidine | 5 | 4000 | 1.06 |
| D9 | di-guanidine | 9 | 7000 | 1.08 |
| D12 | di-guanidine | 12 | 9300 | 1.1 |
| D18 | di-guanidine | 18 | 14000 | 1.09 |

5a: R=Methyl. (M9) $^1$H NMR (300 MHz, DMSO-$d_6$): $\delta$=11.49 (1H, br), 8.42 (1H, br), 7.41 (0.5H, br), 5.80 (trans) and 5.58 (cis) (2H total, br), 4.90 (trans) and 4.56 (cis) (2H total, br), 4.10 (2H, br), 3.52 (3H, br), 3.20 (2H, br), 3.04 (2H, br), 2.80 (0.4H, br), 2.35 (0.2H, br), 2.29 (0.2H, br), 1.45 (9H, s), 1.37 (9H, s)

5b: R=1,3-Di-Boc-2-ethyl guanidine (D5) $^1$H NMR (300 MHz, DMSO-$d_6$): $\delta$=11.46 (2H, br), 8.38 (2H, br), 7.31 (1H, br), 5.80 (trans) and 5.56 (cis) (2H total, br), 4.96 (trans) and 4.58 (cis) (2H total, br), 4.09 (4H, br), 3.49 (4H, br), 3.17 (2H, br), 2.77 (0.8H, br), 2.29 (0.4H, br), 2.24 (0.4H, br), 1.41 (18H, s), 1.34 (18H, s)

Polymers 5a-b and TFA salt of 2-(7-nitrobenz-2-oxa-1, 3diazole)-ethylenediamine (NBD-ethylenediamine) (1:1.5 ratio) were dissolved in 1 mL anhydrous DMF; then DIPEA (1 eq.) was added and stirred overnight in the dark. (Taliani, et. al. 2007 *J Med. Chem.* 50, 404-407.) 3 mL RO water was added to the reaction flask, filled into a porous membrane and was dialyzed against RO water. Then the polymers were freeze-dried. For further purification, the resulting polymer was dissolved in 1 mL of THF and filtered through a short silica column. Polymers 6a-b were obtained after complete evaporation of the solvent.

6a: R=Methyl. (M9)$^1$H NMR (300 MHz, DMSO-$d_6$): $\delta$=11.49 (1H, br), 8.42 (1H, br), 7.40 (0.5H, br), 5.80 (trans) and 5.58 (cis) (2H total, br), 4.90 (cis) and 4.56 (trans) (2H total, br), 4.10 (2H, br), 3.52 (3H, br), 3.20 (2H, br), 3.04 (2H, br), 2.35 (0.2H, br), 2.29 (0.2H, br), 1.45 (9H, s), 1.37 (9H, s).

6b: R=1,3-Di-Boc-2-ethyl guanidine. (D5) $^1$H NMR (300 MHz, DMSO-d$_6$): δ=11.50 (2H, br), 8.41 (2H, br), 7.31 (1H, br), 5.83 (trans) and 5.54 (cis) (2H total, br), 4.99 (cis) and 4.61 (trans) (2H total, br), 4.16 (4H, br), 3.52 (4H, br), 3.15 (2H, br), 2.34 (0.4H, br), 2.27 (0.4H, br), 1.44 (18H, s), 1.37 (18H, s)

Polymers 6a-b were dissolved in 4 mL DCM and 4 mL TFA for deprotection. After stirring overnight, the excess acid was removed by azeotropic distillation with methanol. After complete evaporation of the acid, samples were dissolved in methanol:water (1:20) and dialyzed against RO water until the conductivity of water was ~0.1 μS. Then deprotected polymers were recovered by lyophilization. The final deprotected polymers 7a-b were protected from moisture and stored at 4° C.

7a: R=Methyl (M9) $^1$H NMR (300 MHz, DMSO-d$_6$): δ=7.84 (1H, br), 7.34 (4H, br), 5.81 (trans) and 5.63 (cis) (2H total, br), 4.92 (cis) and 4.55 (trans) (2H total, br), 4.05 (2H, br), 3.58 (3H, br), 3.25 (2H, br).

7b: R=ethyl guanidinium. (D5) $^1$H NMR (300 MHz, DMSO-d$_6$): δ=7.99 (2H, br), 7.43 (8H, br), 5.83 (trans) and 5.60 (cis) (2H total, br), 4.96 (cis) and 4.62 (trans) (2H total, br), 4.05 (4H, br), 3.27 (2H, br), 2.20 (0.4H, br), 2.11 (0.4H, br).

Synthesis of Polymer 8 exo,exo-7-oxa-5-norbornene-2,3-dicarboxylic anhydride was synthesized according to the procedure published previously. (Lienkamp, et al. 2009 *J. Polym. Sci. Part A: Polym. Chem.* 47, 1266-1273.) Polymer 8 was synthesized with the same procedure as described above.

8: $^1$H NMR (300 MHz, DMSO-d$_6$): δ=12.67 (2H, br), 8.53 (0.1H, br), 7.33 (1H, br), 6.43 (0.1H, br), 5.77 (trans) and 5.52 (cis) (2H total, br), 5.30 (trans) and 5.25 (cis) (0.2H total, br), 5.15 (cis) and 5.10 (trans) (0.2H total, br), 4.92 (cis) and 4.51 (trans) (2H total, br), 2.99 (2H, br), 2.72 (0.1H, br), 2.33 (0.1H, br), 2.26 (0.2H, br), 1.22 (0.2H, br).

Cell Cultures

Human Embryonic Kidney (HEK293T) cells were cultured in Iscove's Modified Dulbecco's Medium (IMDM), supplemented with 10% (v/v) fetal bovine serum (FBS), 0.05 mg/ml gentamicin, 10 mM NlE aminoacids, and sodium pyruvate. Chinese Hamster Ovary (CHO) cells were cultivated in nutrient mixture F-12 (Ham's F-12) with 10% (v/v) FBS. Jurkat cells (human T cell line, E6.1) were grown in RPMI 1640 (+ glutamaxI), supplemented with 10% (v/v) FCS.

Cellular Uptake Experiments with Fluorescence Activated Cell Sorter (FACS)

A known amount of NBD-labeled polymers were dissolved in PBS (pH=7.2) and filtered with a sterile 0.22 μM syringe filter. On the day of the experiment, cells were counted, centrifuged and resuspended in a complete growth medium to obtain $1 \times 10^6$ cells/ml for HEK293T and Jurkat T cells, $1 \times 10^5$ cells/ml for CHO cells. NBD-labeled molecules were incubated with cells in the same medium either at 37° C. or 4° C. (final volume was 1 mL) for 30 min. Then cells were placed in eppendorf tubes, centrifuged and washed 2 times with ice-cold CBE (PBS containing 0.2% BSA and 1 mM EDTA). The cells were then resuspended in 500 μL CBE and analyzed by fluorescence activated cell sorter-FACS (BD LSR II). Cell associated fluorophores were excited at 488 nm, and fluorescence was measured at 530 nm. The fluorescence signal was collected for 10,000 cells, and the cells exhibiting a normal morphology were used to obtain a histogram of fluorescence intensity per cell. The calculated mean of the distribution represented the amount of cell associated molecules.

For the quenching experiments, after the last washing step, cells were treated with freshly prepared 5 μM sodium dithionite solution (in 1M TRIS pH=10) for 5 min then washed and resuspended in 0.5 mL ice-cold CBE for FACS analysis.

The fluorescence obtained with dithionite treatment was named as internalized and the fluorescence obtained without dithionite treatment was named as total cell associated. The percent cellular uptake which is reported in the main text is the ratio of internalized fluorescence to total fluorescence.

Percent Cellular Uptake=[(Internalized fluorescence)/ (Total fluorescence)]*100

7-AAD Viability Test

Cells were treated with the polymers at 37° C. in complete growth media for 1 hour as described above. After the last washing step, 20 μL of 7-AAD (7-amino-actinomycin D) viability dye was added to the cells in 500 μL CBE buffer, incubated on ice and in dark at least for 20 min and immediately analyzed by FACS.

Confocal Microscopy

Cells were seeded in NUNC 2 chambers to reach 50% confluence 1 day after seeding. On the day of the experiment, before incubating cells with the compounds, old media was removed and pre-heated fresh medium was added. After 1 hour of incubation with NBD-labeled polymers, cells were washed with HBSS buffer and then incubated with lysotracker red-99 for 4 min in HBSS. After 4 min incubation, cells were washed 2 times and placed into HBSS buffer for imaging. Cells were observed with an inverted LSM510 laser scanning confocal microscope (Carl Zeiss) and 40× oil immersion objective.

Aromatic Functionality in Synthetic Mimics

A new series of PDTMs were designed to determine if aromatic functionality provides better transduction efficiency than aliphatic ones, at the same relative hydrophobicity. Given the importance of aromatic amino acids in membrane proteins and their interactions with the bilayer, it was proposed that aromatic side chains would make better activators, given equal relative hydrophobicity. Using reverse-phase HPLC to determine side chain hydrophobicity and $EC_{50}$ values in a classic transduction experiment, it was possible to differentiate between side chain hydrophobicity and aromaticity.

Figure 38:
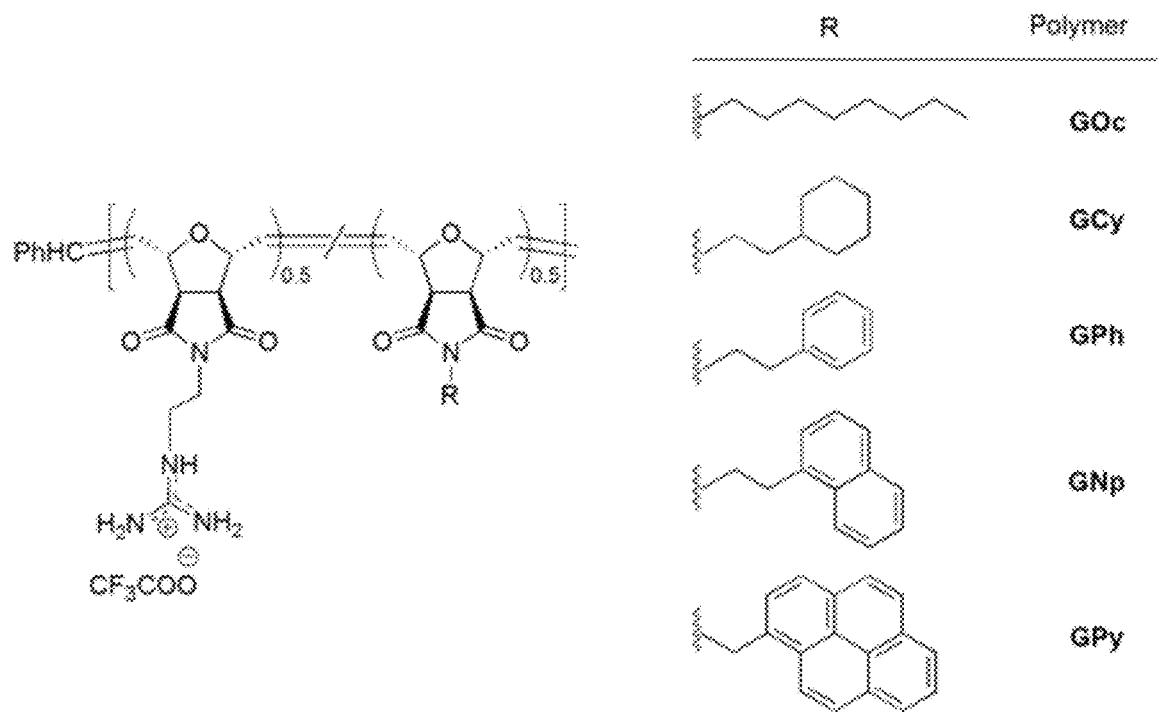
FIG. 38. Structure of oxanorbornenes derived guanidino copolymers used in this study.
Figure 39:
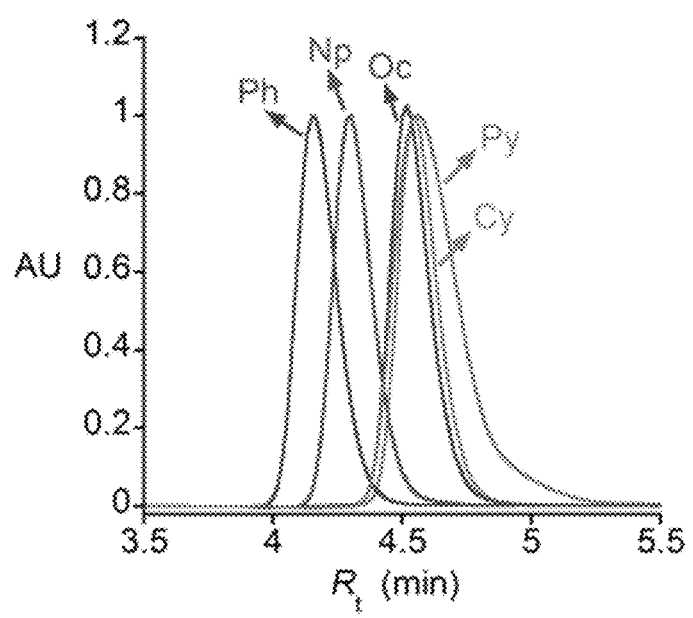
FIG. 39. Retention time ($R_t$) on a reverse-phase C8-HPLC column (under isocratic condition, 100% acetonitrile) of the corresponding hydrophobic monomers that were copolymerized with the guanidine monomers. Individual $R_t$ (min) of the monomers: Ph, 4.15; Np, 4.27; Oc, 4.50; Cy, 4.55; Py, 4.57.

As shown in FIG. 38, a series of new PTDM polymers were prepared via ring opening metathesis polymerization. Monomers were prepared via Mitsunobu coupling reactions. Five different alcohols were used to prepare these monomers including 1-octanol (Oc), 2-cyclohexylethanol (Cy), 2-phenylethanol (Ph), 2-(1-napthyl)ethanol (Np), and 1-pyrenylmthanol (Py). Random copolymers (50:50 mol %) were prepared with degrees of polymerization between 30-35 and $M_n$=10.6-16.6 kDa for the Boc-protected polymers. Gel-permeation chromatography gave monomodal signals and narrow polydispersity indices (1.05-1.08). The Boc protected polymers were deprotected and their transduction activities were studied.

Figure 2:
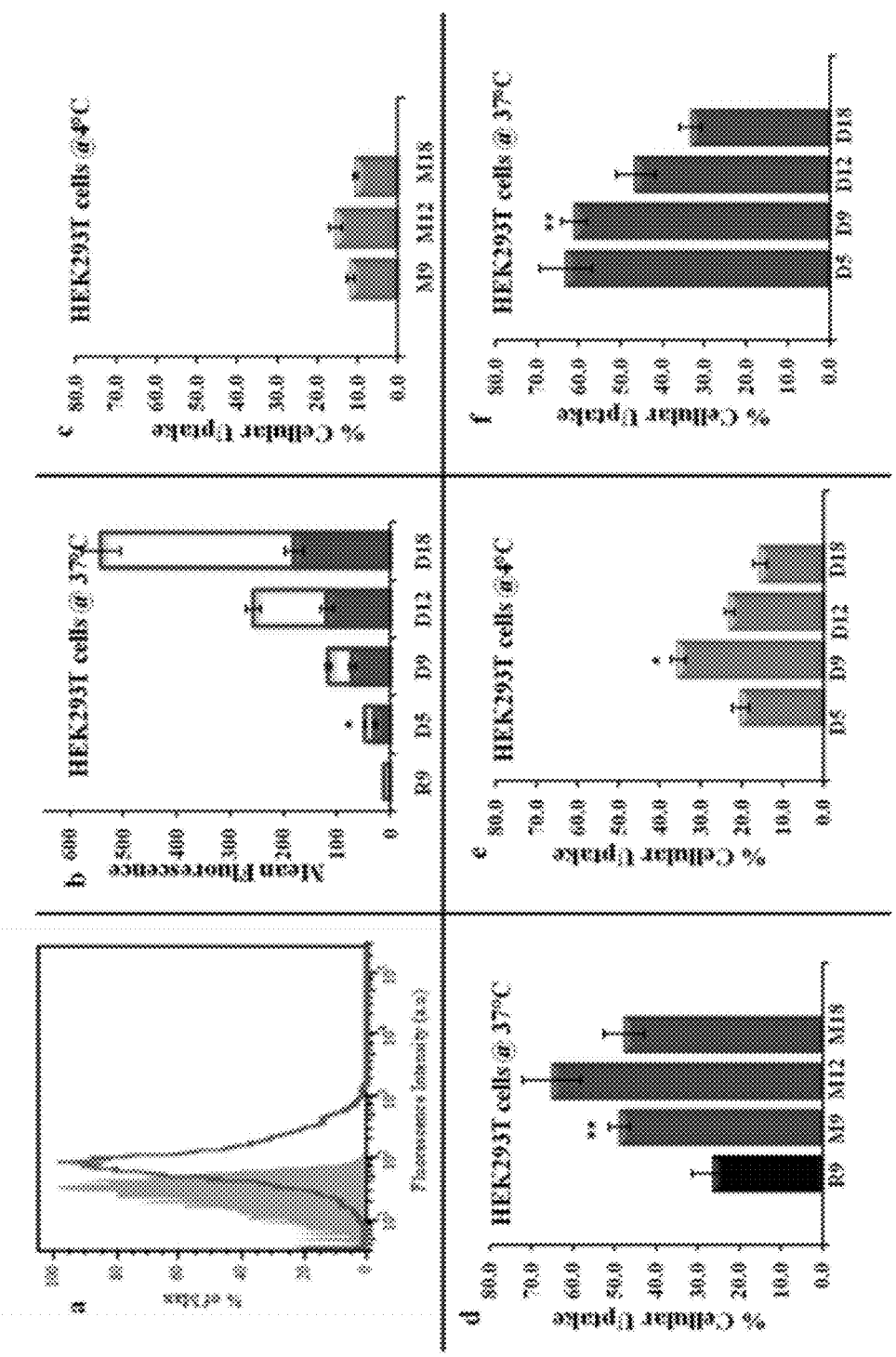
FIG. 2: Internalization of molecules in HEK293T cells. a) Representative FACS histogram showing the cellular uptake of 5 μM NBD-labeled D9 molecule at 37° C. after treatment with the NBD/dithionite assay. The solid gray curve is untreated HEK293T cells; the red line represents cells treated with D9. b) HEK293T cells were treated with di-guanidinium polymers (D5, D9, D12, D18) at 37° C. The amount of surface bound and internalized molecules was determined by the NBD/dithionite assay. The amount of molecules bound to the surface (open bars) was obtained by subtracting the amount of internalized PTDMs (closed bars) from the total mean fluorescence intensity. The mean fluorescence of internalized polymers (after quenching the cell surface bound fraction of polymers by dithionite) was divided by the total mean fluorescence (before dithionite quenching) and multiplied by 100 to obtain the percent cellular uptake. *(P<0.05) of D5 versus R9 mean fluorescence at 37° C. Translocation of polymers were represented as the percentage of internalization in HEK293T cells treated with 5 μM NBD-labeled nonaarginine (R9) control and methyl-guanidinium polymers (Mn) c) at 4° C. and d) at 37° C. **(P<0.01) of M9 versus R9 percent cellular uptake. e) Percent cellular uptake in HEK293T cells treated with 5 μM NBD-labeled di-guanidinium polymers (Dn) at 4° C., *(P<0.05) of D9 versus D18 percent cellular uptake and f) at 37° C., **(P<0.01) of D9 versus D18 percent cellular uptake. Each point is the mean±S.D. of three separate determinations.

Reverse-phase HPLC was performed on each non-polar monomer. Using a C8-column in 100% acetonitrile (isocratic), the chromatograms of all five nonpolar monomers were obtained as shown in FIG. 2. Since pyrene has been commonly used as an activator of polyarginine its retention time ($R_t$) was of particular interest. (Takeuchi, et al. 2006 *ACS Chem. Biol.* 1, 299; Sakai, et al. 2003 *J. Am. Chem. Soc.*

125, 14348; Sakai, et al. 2006 *Soft Matter* 2, 636; Sakai, et al. 2005 *Chembiochem* 6, 114; Nishihara, et al. 2005 *Org. Biomol. Chem.* 3, 1659; Perret, et al. 2005 *J. Am. Chem. Soc.* 127, 1114.) Here, its $R_t$ was 4.57 minutes while the eight carbon-containing aliphatic monomers yielded similar $R_t$s of 4.55 (Cy), and 4.50 (Oc). As a result, these three monomers have similar relative hydrophobicities. In contrast, the other two aromatic monomers, Np and Ph are less hydrophobic with $R_t$s of 4.27 and 4.15 minutes, respectively. This series of monomers spans a range of relative hydrophobicities and therefore enables the deconvolution of hydrophobicity and aromaticity in transduction activity.

Figure 42:
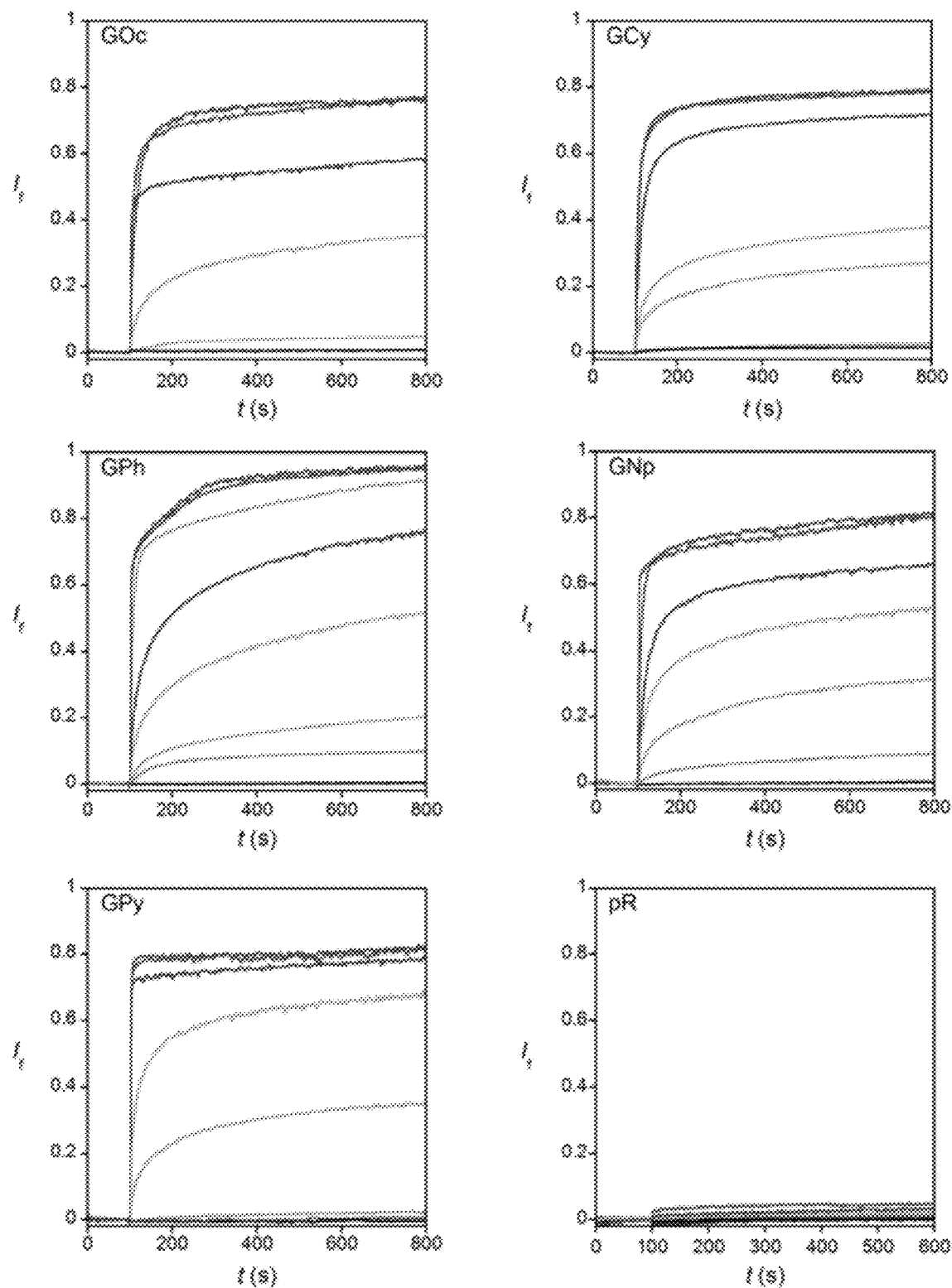
FIG. 42. Representative normalized original kinetics for GOc, GCy, GPh, GNp, GPy, and polyarginine (pR) following CF fractional emission intensity $I_f$ ($\lambda_{ex}$=492 nm, $\lambda_{em}$=517 nm) as a function of time during the addition of EYPC-LUVs⊃CF (t=0 s), polymer (t=100 s) and Triton X-100 (t=900 s).
Figure 43:
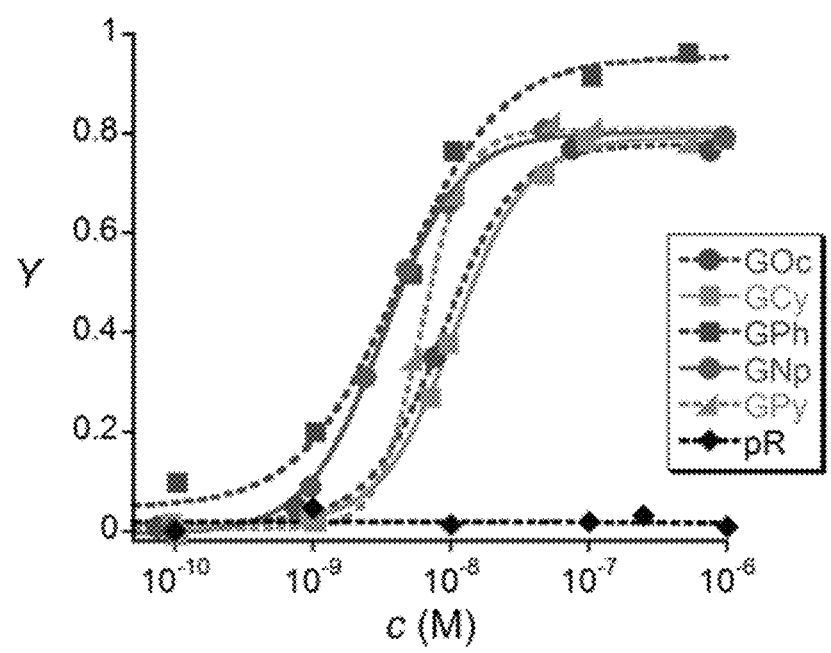
FIG. 43. Fractional emission intensity $I_f$ at 800 s from FIG. 41 (transmembrane activity Y) was plotted against polymer concentration (c) and fitted to hill equation S2.

Transport activities for these novel PTDMs were determined using the standard biophysical assay well documented in the CPP literature. (Hennig, et al. 2008 *J. Am. Chem. Soc.* 130, 10338.) Specifically, 5(6)-carboxyfluorescein (CF) was used as a fluorescent probe in egg yolk phosphatidylcholine large unilamellar vesicles (EYPC-LUVs). The activity of these transporters increased with increasing polymer concentration at a constant vesicle concentration as detected by CF emission intensity, yielding plots of fluorescence intensity versus polymer concentration (FIG. 42, FIG. 43). Fitting the Hill equation [$Y \propto (c/EC_{50})^n$] to this data for each individual polymer revealed a nonlinear dependence of the fractional fluorescence intensity, Y, on the polymer concentration, c, which is classical behavior demonstrated by CPPs. (Sakai, et al. 2003 *J. Am. Chem. Soc.* 125, 14348; Sakai, et al. 2006 *Soft Matter* 2, 636; Sakai, et al. 2005 *Chembiochem* 6, 114; Hennig, et al. 2008 *J. Am. Chem. Soc.* 130, 10338; Nishihara, et al. 2005 *Org. Biomol. Chem.*, 3, 1659; Perret, et al. 2005 *J. Am. Chem. Soc.* 127, 1114.) This analysis gave $Y_{max}$ (maximal CF release relative to complete release by Triton X-100), $EC_{50}$ (effective polymer concentration needed to reach $Y_{max}/2$), and the Hill coefficient n (see Table 2). For direct comparison it is worth mentioning that the CPP polyarginine was inactive under these conditions; a known fact since polyarginine needs counterions for activation.

Figure 40:
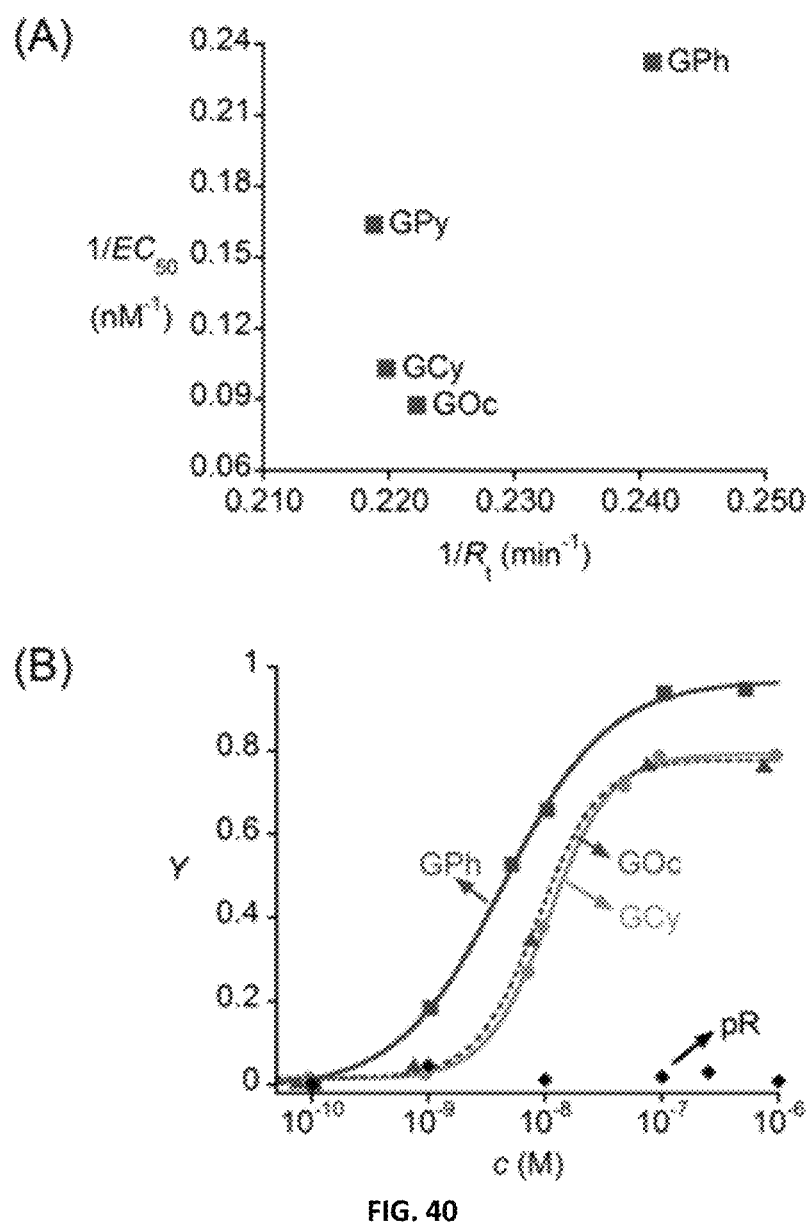
FIG. 40. (A) A plot of $1/EC_{50}$ (for the PTDMs copolymer) vs. $1/R_t$ (for the corresponding monomers) for GOc, GCy, GPy, and GPh. (B) Concentration (c) dependent activity of copolymers GOc, GCy, GPh and polyarginine (pR) in EYPC⊃CF vesicles with fit to Hill equation.

FIG. 40*a* is a plot of $1/EC_{50}$ vs. $1/R_t$ for GOc, GCy, GPy and GPh. The data was plotted in this way to give the most efficient transporter the highest value as it relates to effective concentration. Since lower $EC_{50}$ values are said to be more active, $1/EC_{50}$ directly provides the largest value for the best transporter. Similarly, it would be ideal to limit the hydrophobicity of the transporters while maintaining efficient transport activity, thus $1/R_t$ was plotted since the retention time is larger for more hydrophobic monomers. FIG. 40*a* shows that while GOc, GCy, and GPy have similar $1/R_t$ values, GPy is a more effective transporter (higher $1/EC_{50}$). In fact, it is approximately 1.5 to 2.0 times more active than GOc or GCy, despite the similar relative hydrophobicities of their corresponding nonpolar monomers. This activity difference is similar to that previously reported for pyrene ($EC_{50}$, 6.7 µM and 9.3 µM) vs. alkyl activators ($EC_{50}$, 16 µM and 19 µM), suggesting aromatic functionality may indeed have a special role in PTD(M) transduction.

Further support for this hypothesis comes from comparing the values ($EC_{50}$ and hydrophobicity) of GPh to the others in FIG. 3*a*. GPh is the least hydrophobic (larger $1/R_t$) yet it is the most active (higher $1/EC_{50}$). This is consistent with phenylalanine's unique ability to partition at the membrane interface and in the membrane core. (Sengupta, et al. 2008 *Biochim. Biophys. Acta.* 1778, 2234.) FIG. 40*b* shows the Hill plots for GOc, GCy, and GPh which yields their respective $EC_{50}$ values of 11.4±2.8, 9.7±0.9, and 4.3±0.1 nM. This comparison is particularly interesting since all three non-polar monomers contain eight total carbons. In addition, both GPh and GCy contain cyclic rings and, in fact, represent the closest possible structural analogues. While the aromatic group was expected to be less hydrophobic, it clearly demonstrates that transduction activity is not solely dominated by hydrophocity; but rather that aromaticity plays a crucial role. (Talhout, et al. 2004 *Org. Biomol. Chem.* 2, 3071.) It also shows that the large pyrene-ring is not essential and that smaller, more protein-like aromatic groups, can effectively promote transduction in these PDTMs.

Figure 41:
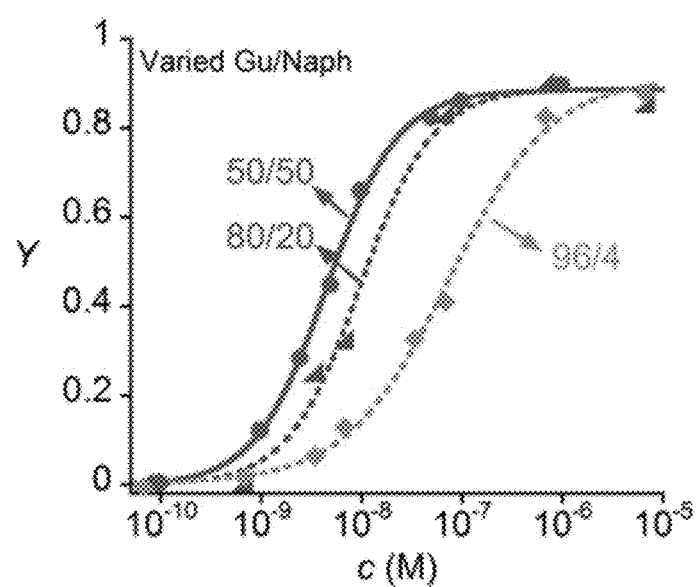
FIG. 41. Hill plot of GNp copolymers with different guanidine to naphthyl repeat unit ratios in EYPC⊃CF vesicles with fit to Hill equation.

To further examine the role of aromatic size on transduction activity for this system, copolymers containing naphthyl were prepared. The 50:50 copolymer provided a similar $EC_{50}$ value (3.8±0.6 nM, see FIG. 41 and Table 2) to the other aromatic-containing polymers. Given the similarity in values among all three aromatic-containing polymers, the molar content of napthyl was lower to understand whether or not a 'threshold' of aromatic content was needed for activity. As FIG. 41 shows, the activity of GNp decreased with decreasing molar content of napthyl, suggesting that no threshold was present. This data indicates that when more napthyl is present in the polymer it is more effective at transduction, although there is likely an upper limit, at least due to solubility of the polymer.

Table 2 summarizes the Hill parameters for these polymers and shows that they all have similar $Y_{max}$ values and Hill coefficients, n, around 2, suggesting poor cooperativity. This supports transduction and no requirement for multi-chain structures being involved in the transport activity. At the same time, this assumes the mechanism of action in these experiments is transduction and not some type of general pore formation. Previously the activity of the PTDMs was compared against EYPC/EYPG vesicles containing either CF or calcein. Calcein loaded vesicles are routinely used to demonstrate pore-formation induced by antimicrobial peptides and their synthetic mimics.[16] Nonlinear increases in the fractional fluorescence from EYPC/EYPG⊃CF vesicles as a function of concentration were observed while no fluorescence increase was observed for EYPC/EYPG⊃Calcein vesicles. These experiments strongly supported the hypothesis that these class of PTDMs exhibit transduction activity. As a result, transduction is the most likely and expected mechanism here.

TABLE 2

$EC_{50}$, $Y_{max}$, and Hill coefficient of the copolymers transduction activity

| Polymer | $EC_{50}$ (nM) | $Y_{max}$ | n |
|---|---|---|---|
| GOc (50:50) | 11.4 ± 2.8 | 0.80 ± 0.02 | 1.7 ± 0.05 |
| GCy (50:50) | 9.7 ± 0.9 | 0.80 ± 0.03 | 2.6 ± 1.0 |
| GPh (50:50) | 4.3 ± 0.1 | 0.96 ± 0.01 | 1.1 ± 0.1 |
| GNp (50:50) | 3.8 ± 0.6 | 0.84 ± 0.04 | 1.4 ± 0.2 |
| GNp (80:20) | 7.8 ± 1.8 | 0.88 ± 0.02 | 1.2 ± 0.2 |
| GNp (96:04) | 73 ± 0.9 | 0.91 ± 0.03 | 0.9 ± 0.1 |
| GPy (50:50) | 6.1 ± 0.2 | 0.81 ± 0.01 | 2.8 ± 0.3 |

The molar ratios between guanidino repeat units and the hydrophobic repeat units are reported in the parenthesis. $Y_{max}$ (maximal CF release relative to complete release by Triton X-100); $EC_{50}$ (effective polymer concentration needed to reach $Y_{max}/2$); n, Hill coefficient. Each data point was collected in three independent experiments.

In order to compare 'activators' of varying $EC_{50}$s and total fractional transport activity, activator efficiency, E, was calculated based on the exponential relationship between $Y_{max}$ and $EC_{50}$. (Nishihara, et al. 2005 *Org. Biomol. Chem.* 3, 1659.) The same arbitrary scaling factor previously was used to calibrate E between 0 and $10^{5a}$ was also used here to determine E values for these covalently activated PTDMs (Table 3). For GPh, E was found to be 25, or 2.5 times larger than the highly active fullerene analog and 5 times better than pyrene butyrate. These covalent PDTMs have both low $EC_{50}$ and high $Y_{max}$ values, features previously suggested for the perfect activator. (Nishihara, et al. 2005 *Org. Biomol. Chem.* 3, 1659.) This is markedly different from the supramolecular activators in which more potent activators (lowest $EC_{50}$s) also had low $Y_{max}$ values. The fact that these covalently activated PTDMs are more effective than the supramolecular analogs (pR-activator) is not necessarily surprising since covalent attachment eliminates the binding equilibrium between pR and the activator. The best activators most likely also have solubility limitations since they are significantly hydrophobic. At the same time, the ability to design PTDMs that are significantly more active than classical CPPs is extremely encouraging.

TABLE S1

| Polymer (low $M_n$) | $EC_{50}$ (μM) | $Y_{max}$ | n |
|---|---|---|---|
| G1 | 20.0 ± 0.9 | 0.85 ± 0.03 | 1.2 ± 0.1 |
| G2 | 2.4 ± 0.2 | 1.0 | 1.0 ± 0.3 |
| G3 | 0.3 ± 0.04 | 0.96 ± 0.01 | 2.5 ± 0.6 |
| G4 | 0.2 ± 0.06 | 0.95 ± 0.02 | 2.5 ± 0.2 |
| G5 | 0.6 ± 0.03 | 0.98 ± 0.01 | 1.8 ± 0.4 |
| G9 | 5.4 ± 0.4 | 0.60 ± 0.03 | 1.7 ± 0.3 |
| G12 | 6.8 ± 0.5 | 0.51 ± 0.03 | 3.5 ± 0.3 |

Using HPLC to determine the relative hydrophobicity of various side chains, it was possible to demonstrate the improved transport activity of aromatic functionality. This provides guidance for building molecules that more favorably interact with the membrane while reducing the overall hydrophobicity. Understanding the broader goals of how macromolecules (synthetic or natural) interact with the biological membrane is critically important. At the same time, learning to program synthetic polymers with natural protein-like activity remains an incredibly important task of modern macromolecular chemistry. Many fundamental questions remain but these new synthetic PDTMs appear to be useful tools for studying macromolecular-membrane interactions.

Monomers of Copolymers

These monomers were synthesized following reported procedure with minor modifications. (Gabriel, et al. 2009 *Chem. Eur. J* 15, 433-439)

Scheme 4. The synthetic scheme of oxanorbornene imide

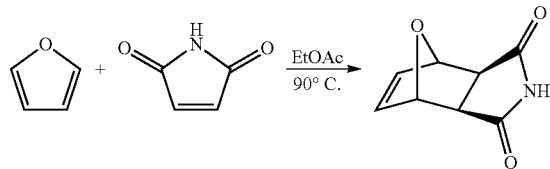

Oxanorbornene Imide.

10.0 g (103 mmol) of maleimide was dissolved in 100 mL of ethyl acetate. 7.7 g (8.2 mL, 113.0 mmol) of furan were added and the resulting solution was vigorously stirred at 90° C. for 3 h to obtain product oxanorbornene imide as a white precipitate. Product was then filtered, washed with excess diethyl ether, and dried under vacuum overnight. 100% exo isomer was obtained as a colorless powder. Spectroscopic data matched the previously reported ones (Yield=75%). (Kim, et al. 1997 *Journal of Applied Polymer Science* 64, 2605-2612.)

Scheme 5. The synthetic scheme of guanidine monomer.

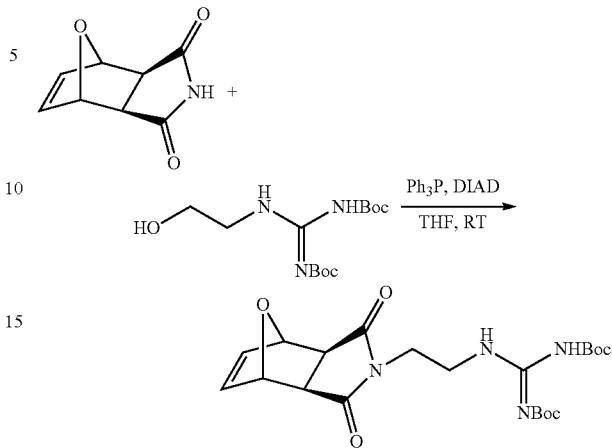

DiBoc-Protected Guanidine Monomer (G)

To a round-bottom flask charged with oxanorbornene imide (1.0 g, 6.0 mmol), 1,3-Di-Boc-2-(2-hydroxyethyl)guanidine (2.12 g, 7.0 mmol) and triphenylphosphine (1.6 g, 6.0 mmol), THF (30 mL) were added. The solution mixture was then immersed in an ice bath, and diisopropyl azodicarboxylate (DIAD) (1.2 mL, 6.0 mmol) was added dropwise. After the addition of DIAD, the ice bath was removed and the reaction was allowed to stir at room temperature for 24 h. The solvent was removed under reduced pressure, and the product was crystallized from diethyl ether and was purified by column chromatography (silica gel, 96:4 dichloromethane/acetone) in 70% yield. NMR characterization of this monomer is reported below.

DiBoc-Protected Guanidine Monomer (G): $^1$H NMR (300 MHz, $CDCl_3$): δ=11.45 (1H, s), 8.41 (1H, s), 6.51 (2H, s), 5.26 (2H, s), 3.68 (2H, m), 3.60 (2H, m), 2.86 (2H, s), 1.50 (9H, s), 1.47 (9H, s). $^{13}$C-NMR (75 MHz, DMSO-$d_6$): δ=176.3, 156.6, 153.0, 136.5, 83.3, 80.9, 47.6, 39.0, 38.4, 28.3, 28.1. HR-MS (FAB): calc. 451.49, found 451.22.

Scheme 6. The synthetic scheme of hydrophobic monomers

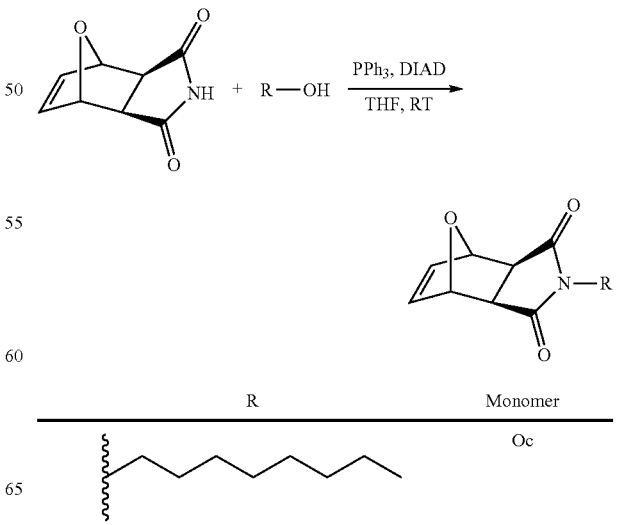

Scheme 6. The synthetic scheme of hydrophobic monomers

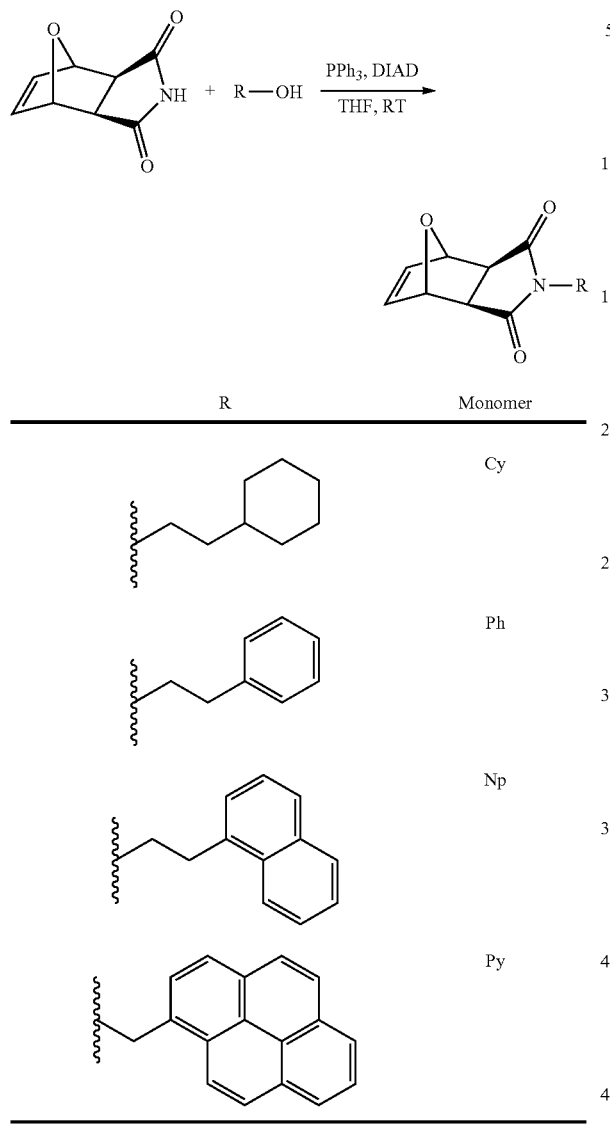

Hydrophobic Monomers

Oxanorbornene imide (1.0 g, 6.0 mmol, 1 eq.), the appropriate alcohol (1.16 eq.) and triphenylphosphine (1.6 g, 6.0 mmol), dry THF (35 mL) were added to a round-bottom flask, purged with nitrogen. The reaction mixture was stirred and the cooled to 0° C. in an ice bath and diisopropyl azodicarboxylate (DIAD) (1.2 mL, 6.0 mmol) was added dropwise. After the addition of DIAD the ice bath was removed and the solution was allowed to stir for 16 h. The solvent was removed under reduced pressure. To remove by-products, the solid was dissolved in minimum amount of toluene. The precipitating solid was filtered and the solvent in the mother liquor removed under reduced pressure. The oil was dissolved in minimum amount of diethylether. The precipitating solid was dissolved in minimum amount of dichloromethane and purified by column chromatography using a dichloromethane/ethyl acetate gradient in 70-80% yield. NMR characterization of monomers follows below.

Octyl Monomer (Oc). $^1$H NMR (300 MHz, CDCl$_3$): δ=6.48 (2H, s), 5.22 (2H, S), 3.42 (2H, t, J=7.3 Hz), 2.80 (2H, s), 1.51 (dq, J=6.8 Hz, 8.3 Hz, 2H), 1.22 (10H, br), 0.85 (3H, t, J=6.0 Hz). $^{13}$C-NMR (75 MHz, CDCl$_3$): δ=176.2, 136.4, 80.8, 62.8, 47.2, 38.9, 31.6, 29.0, 27.5, 26.5, 22.5, 14.0. HR-MS (FAB): calc. 277.17, found 278.17.

Cyclohexyl Monomer (Cy). $^1$H NMR (300 MHz, CDCl$_3$): δ=6.49 (2H, s), 5.24 (2H, s), 3.46 (2H, t, J=7.6 Hz), 2.81 (2H, s), 1.64 (5H, m), 1.41 (2H, q, J=7.5 Hz), 1.20 (4H, m), 0.90 (2H, m). $^{13}$C-NMR (75 MHz, CDCl$_3$): δ=176.3, 136.6, 80.9, 47.4, 37.1, 35.4, 34.9, 32.9, 26.5, 26.2. HR-MS (FAB): calc. 276.35, found 276.16.

Phenyl Monomer (Ph). $^1$H NMR (300 MHz, Acetone-d$_6$): δ=7.26 (5H, m), 6.59 (2H, s), 5.14 (2H, s), 3.62 (2H, t, J=7.7 Hz), 2.91 (2H, s), 2.79 (2H, t, J=6.9 Hz). $^{13}$C-NMR (75 MHz, CDCl$_3$): δ=176.0, 137.8, 136.6, 128.9, 128.5, 126.6, 80.9, 47.4, 40.2, 33.7. HR-MS (FAB): calc. 270.30, found 270.11.

Naphthyl Monomer (Np). $^1$H NMR (300 MHz, Acetone-d$_6$): δ=8.30 (1H, d, J=8.1 Hz), 7.94 (1H, d, J=7.8 Hz), 7.82 (1H, dd, J=7.2 Hz, 2.1 Hz), 7.65-7.52 (2H, m), 7.47-7.40 (2H, m), 6.60 (2H, s), 5.19 (2H, s), 3.74 (2H, td, J=4.1 Hz, 7.5 Hz), 3.27 (2H, td, J=3.6 Hz, 6.8 Hz), 2.95 (2H, s). $^{13}$C-NMR (75 MHz, CDCl$_3$): δ=176.1, 136.6, 134.0, 133.8, 132.0, 128.8, 127.6, 127.1, 126.4, 125.7, 125.5, 123.7, 80.9, 47.5, 39.7, 31.2. HR-MS (FAB): calc. 319.35, found 319.12.

Pyrene Monomer (Py). $^1$H NMR (300 MHz, DMSO-d6, poor solubility): δ=8.48–7.87 (9H, m), 6.58 (2H, s), 5.31 (2H, s), 5.22 (2H, s), 3.08 (2H, br). HR-MS (EI): calc. 379.40, found 379.10.

Reverse-Phase HPLC Analysis. Solutions of Oc, Cy, Ph, Np, and Py monomers (in acetonitrile) were eluted off of the column (Agilent Zorbax C8 column, 4.6 mm×150 mm) under isocratic condition with 100% acetonitrile; flow rate was 0.5 mL/min and absorbance at 212 nm was monitored in Waters 2695 Separation Module HPLC system equipped with a Waters 2996 photodiode array.

Scheme 7. The synthetic scheme of copolymers.

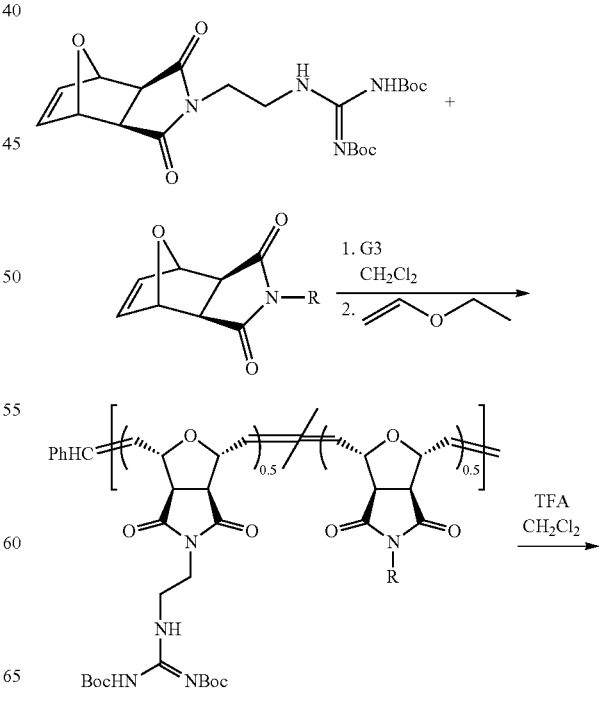

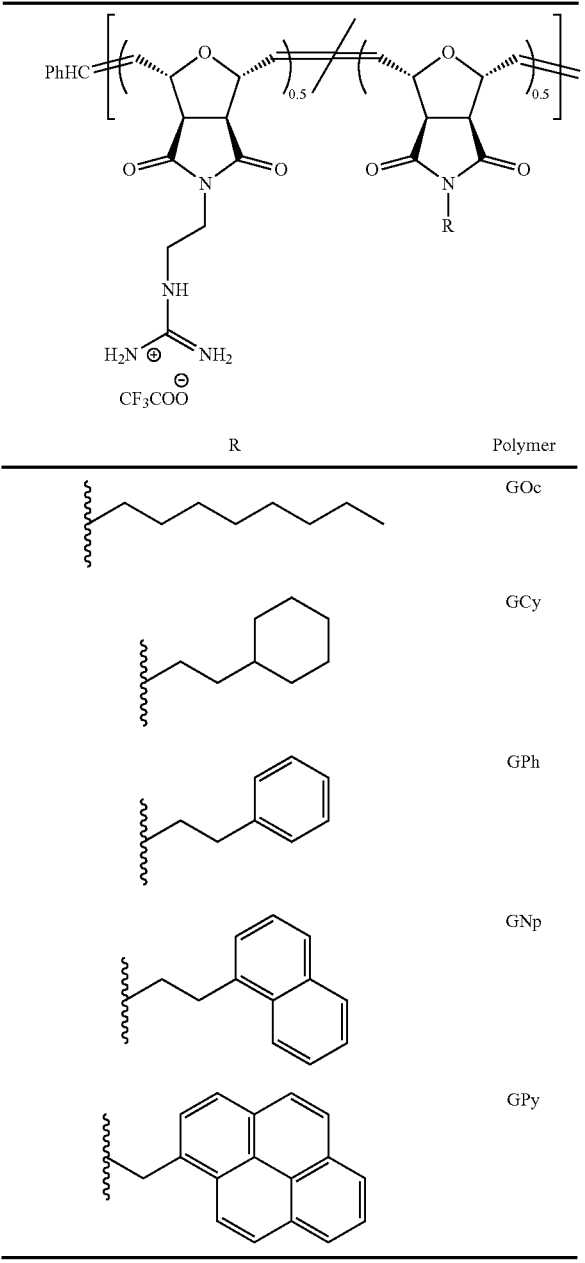

The 50:50 random copolymers were prepared following the procedure by Gabriel et. al. Monomers were copolymerized by ring-opening metathesis polymerization (ROMP) using Grubbs' 3$^{rd}$ generation catalyst, G3, Dichloro-di(3-bromopyridino)-N,N'-Dimesitylenoimidazolino-Ru=CHPh. The polymerization entailed adding to a schlenk tube the appropriate monomers (ca. 100 mg total) and in another schlenk tube the G3 catalyst. The schlenk tubes were purged with $N_2$ for 5 min, then 1 mL dry $CH_2Cl_2$ was injected into both tubes followed by three freeze thaw cycles. Afterwards the monomer solution was added into the catalyst solution via syringe all at a time. The $N_2$ line was removed and the clear, brown solution was stirred at 30° C. for 30 min after which 0.4 mL ethyl vinyl ether was injected to terminate the polymerization. After stirring for 15 min the solution was added dropwise to 300 mL of stirring pentane to precipitate the polymer. The pentane solution was stirred an additional 30 min and left standing undisturbed for an hour. The precipitate was then collected by a fine sintered funnel and then dried by vacuum for 8 h. GNp 80:20 copolymers, and GNp 96:4 copolymers were prepared following the same general procedure reported above only by changing the appropriate monomer ratios. NMR and GPC characterization of all the Boc-protected copolymers follows below.

The Boc-protected polymers were deprotected by stirring 100 mg in 4 mL of 1:1 TFA:$CH_2Cl_2$ for 6 h. The solution was dried under $N_2$ to an oil and the residual TFA was removed by washing the oil in $CH_2Cl_2$/MeOH and evaporating the solvent by rotary evaporator. After three more MeOH wash and the solvent evaporation, the resulting solid was placed under vacuum for 2 h. Finally, the solid was fully dissolved in 4 mL 1:1 MeOH:$H_2O$ and freeze-dried for 48 h to give an eggshell colored soft solid. Final deprotected polymers were stored at −20° C. NMR characterization of the deprotected copolymers follows below. After Boc-deprotectionand and MeOH wash, GNp and GPy copolymers were precipitated in cold ether. The precipitate was then collected by a fine sintered funnel and the white solid was dried by vacuum.

Boc-Protected GOc. $^1$H NMR (300 MHz, $CDCl_3$): δ=11.42 (1H, br), 8.48 (1H, br), 6.06 (2H, br), 5.76 (2H, br), 5.02 (2H, br), 4.47 (2H, br), 3.67 (4H, br), 3.43-3.32 (6H, br, m), 1.46 (18H, s), 1.25 (12H, br), 0.85 (3H, br). cis:trans ratio=43:56; $M_n$=14.9 kDa, $M_w/M_n$=1.08.

GOc. (300 MHz, DMSO-$d_6$): δ=7.72 (2H, br, exchanged with $D_2O$), 7.29 (4H, br, exchanged with $D_2O$), 5.94 (2H, br), 5.72 (2H, br), 4.86 (2H, br), 4.41 (2H, br), 1.44 (2H, br), 1.21 (9H, br), 0.82 (3H, br).

Boc-Protected GCy. $^1$H NMR (300 MHz, $CDCl_3$): δ=11.44 (1H, br), 8.50 (1H, br), 6.06 (2H, br), 5.76 (2H, br), 4.99 (2H, br), 4.47 (2H, br), 3.68 (4H, br), 3.47-3.31 (6H, br), 1.71-1.66 (5H, m, br) 1.47 (18H, s), 1.18 (5H, br), 0.90 (3H, br). cis:trans ratio=46:54; $M_n$=13.0 kDa, $M_w$/ML=1.05.

GCy. $^1$H NMR (300 MHz, $CD_3OD$): δ=6.08 (2H, br), 5.84 (2H, br), 5.02 (2H, br), 4.52 (2H, br), 3.69 (2H, br), 3.46 (8H, br), 1.76 (5H, br), 1.45 (2H, br), 1.25 (4H, br), 0.96 (2H, br).

Boc-Protected GPh. $^1$H NMR (300 MHz, $CDCl_3$): δ=11.44 (1H, br, m), 8.50 (1H, br), 7.29-7.18 (5H, br, m, some overlaping with $CHCl_3$ peak; clearly visible, 7.29-7.23, when spectra recorded in Acetone-d6), 5.99 (2H, br, t, J=20.8 Hz), 5.73 (2H, br), 5.06-4.83 (2H, br, m), 4.47 (1H, br), 4.09 (1H, br), 3.68 (6H, br), 3.34-3.18 (4H, br, m), 2.90 (2H, br), 1.49 (9H, br), 1.47 (9H, br), cis:trans ratio=47:53; $M_n$=10.6 kDa, $M_w/M_n$=1.05.

GPh. $^1$H NMR (300 MHz, $CD_3OD$): δ=7.20 (5H, br), 6.15-5.79 (4H, br, m), 4.51 (2H, br), 3.98 (2H, br), 3.68 (4H, br), 3.44 (4H, br), 2.90 (2H, br).

Boc-Protected GNp. $^1$H NMR (300 MHz, $CDCl_3$): δ=11.45 (1H, br, m), 8.52 (1H, br), 8.14 (1H, br), 7.85-7.29 (6H, br, m), 6.00 (2H, br, t, J=21.7 Hz), 5.77 (2H, br), 4.99 (2H, br), 4.49 (1H, br), 4.19 (1H, br), 3.83-3.33 (10H, br, m), 1.49 (18H, br). cis:trans ratio=49:51; $M_n$=11.6 kDa, $M_w/M_n$=1.05.

GNp. (300 MHz, DMSO-$d_6$): δ=8.13 (1H, br), 7.68 (3H, br, m, 1H exchanged with $D_2O$), 7.31 (8H, 4Hs exchanged with $D_2O$), 6.04-5.76 (4H, br, m), 4.91 (2H, br), 4.49 (1H, br), 4.10 (1H, br), 3.65 (2H, br).

Boc-Protected GNp (80:20). $^1$H NMR (300 MHz, $CDCl_3$): δ=11.45 (1H, br, m), 8.48 (1H, br), 8.12-7.34 (2H, br, m), 6.05 (1H, br, m), 5.75 (1H, br), 4.98 (1H, br), 4.50 (1H, br), 4.15-3.31 (7H, br, m), 1.46 (18H, br). cis:trans ratio=49:51; $M_n$=15.8 kDa, $M_w/M_n$=1.05.

GNp (80:20). (300 MHz, DMSO-d$_6$): δ=8.12-7.27 (10H, br, m, 6Hs exchanged with D$_2$O), 5.94-5.74 (4H, br, m), 4.90 (2H, br), 4.41-4.10 (2H, br), 3.65 (1H, br).

Boc-Protected GNp (96:4).

$^1$H NMR (300 MHz, CDCl$_3$): δ=11.45 (1H, br, m), 8.47 (1H, br), 8.12-7.31 (1H, br, m), 6.04 (1H, br, m), 5.75 (1H, br), 5.00 (1H, br), 4.45 (1H, br), 3.66-3.30 (7H, br, m), 1.46 (18H, br). cis:trans ratio=46:54; M$_n$=16.6 kDa, M$_w$/M$_n$=1.05.

GNp (96:4). (300 MHz, DMSO-d$_6$): δ=7.86–7.33 (10H, br, m, 2Hs exchanged with D$_2$O), 5.93 (2H, br), 5.73 (2H, br), 4.90 (2H, br), 4.40 (2H, br).

Boc-Protected GPy. $^1$H NMR (300 MHz, CDCl$_3$): δ=11.43 (1H, br, m), 8.41 (1H, br), 8.20-7.60 (9H, br, m), 5.99 (2H, br), 5.67 (2H, br), 4.92 (2H, br), 4.38 (2H, br), 3.55-3.01 (6H, br, m), 1.44 (18H, br). cis:trans ratio=50:50; M$_n$=11.1 kDa, M$_w$/M$_n$=1.07.

GNp. (300 MHz, DMSO-d$_6$): δ=8.42-7.07 (12H, br, m), 5.93 (2H, br), 5.70 (2H, br), 5.21-4.81 (4H, br), 4.41 (2H, br).

Preparation of Vesicles

Preparation of EYPC-LUVs⊃CF. A thin lipid film was prepared by evaporating a solution of 25 mg EYPC in 2 mL CHCl$_3$ on a rotary evaporator (40° C.) and then in vacuum overnight. After hydration (~1 h) with 1.0 ml buffer (10 mM Tris, 10 mM NaCl, 50 mM CF, pH 7.5) accompanied by occasional vortex, the resulting suspension was subjected to 5 freeze-thaw cycles (liquid N$_2$ to freeze and 40° C. water bath to thaw), and 11 times extruded through a polycarbonate membrane (pore size 100 nm). Extra-vesicular components were removed by size exclusion chromatography (Sephadex G-50, Sigma-Aldrich) with 10 mM Tris, 107 mM NaCl, pH 7.5. The resulting vesicle solution was diluted with buffer B to give CF loaded LUVs stock solution having final lipid concentration of ~2.5 mM. (Hennig, et al. 2008 *J. Am. Chem. Soc.* 130, 10338-10344.)

Fluorescence Assay and Transporter Activity

Polymer Activity in EYPC-LUVs⊃CF. 20 µL EYPC-LUVs⊃CF were added to 1980 µL gently stirred, thermostated buffer (buffer B, 10 mM Tris, 107 mM NaCl, pH 7.5) in a disposable plastic cuvette. The time-dependent change in fluorescence intensity I$_t$ ($\lambda_{ex}$=492 nm, $\lambda_{em}$=517 nm) was monitored during the addition of polymer (20 µL stock solution in DMSO) at t=100 s, and addition of 40 µl 1.2% (aq.) triton X-100 at the end of every experiment (t=900 s) (FIG. 42). (Hennig, et al. 2008 *J. Am. Chem. Soc.* 130, 10338-10344.) Time courses of I$_t$ were normalized to fractional intensities I$_f$ using equation S1.

$$I_f=(I_t-I_0)/(I_\infty-I_0) \quad (S1),$$

where I$_0$=I$_t$ before polymer addition and I$_\infty$=I$_t$ after lysis. I$_f$ at t=800 s just before lysis was defined as transmembrane activity Y. For Hill analysis, Y was plotted against polymer concentration c and fitted to the Hill equation S2 to give effective concentration EC$_{50}$, Y$_{max}$ and the Hill coefficient n.

$$Y=Y_O+(Y_{max}-Y_O)/\{1+c/EC_{50})^n\} \quad (S2),$$

Where, Y$_0$ is Y in absence of polymer, Y$_{max}$ is Y with excess polymer.

NOTCH 1-siRNA Delivery to Primary Cells by PTDs

Use of siRNA to study gene functions in T cell lines and primary blood cells has been limited due to lack of safe and effective delivery vehicles. There are different tools to introduce siRNA into the intracellular medium of the cells such as electroporation, chitosan based-polymers, carbon-nanotubes, and protein transduction domains (PTDs). (Jantsch, et al. 2008 *J. Immunol. Methods* 337, 71-77 (2008); Brahmamdam, et al. 2009 *Shock* 32, 131-139; Liu, et al. 2007 *Angew. Chem. Int. Ed. Engl.* 46, 2023-2027; Marshall, et al. 2007 *J Immunol. Methods.* 325, 114-126; Eguchi, et al. 2009 *Nat. Biotech.* 27, 567-571.) Each of these systems offers some benefits but they all have their own concerns regarding cytotoxicity, ease of preparation, and stability. Therefore, there is a great interest in easily prepared agents for efficient siRNA delivery to hard-to-transfect cells without significant toxicity. Here, two ROMP based PTDMs were prepared and studied. (Trabulo, et al. 2010 *Pharmaceuticals* 3, 961-993; Fonseca, et al. 2009 *Adv. Drug Del. Rev.* 61, 953-964.) There are two different approaches in PTD-based cargo delivery, the first one is attaching cargo to PTD with a covalent linkage, and the second approach is the formation of stable non-covalent complexes between PTD and cargo. (Endoh, et al. 2009 *Adv. Drug Del. Rev.* 61, 704-709.) Especially, in the case of siRNA delivery, second approach is more favored over the first one; in terms of simplicity, delivery efficiency and cargo stability. (Eguchi, et al. 2009 *Trends in Pharm. Sci.* 30, 341-345.)

PTDs used in siRNA delivery via non-covalent complexation, generally have primary or secondary amphiphilic structures, such as, MPG, CADY, and Pep peptides, to enhance both the stability of complexes and internalization properties. (Crombez, et al. 2007 *Biochem. Soc. Trans.* 135, 44-46; Crombez, et al. 2009 *Mol. Ther.* 17, 95-103; Morris, et al. 2007 *Nucleic Acids Res.* 35, e49.) For instance, in the case of Pep-2 peptide which is designed for delivery of DNA mimics, an alanine mapping is performed to determine the essential residues required to form stable complexes with nucleic acids and to improve their delivery into cells. The results show that aromatic residues are required for both binding of the carrier to cargo and the cellular uptake. In addition, it is highlighted that the cationic residues have more impact on internalization rather than cargo stabilization. (Morris, et al. 2007 *Nucleic Acids Res.* 35, e49.) Moreover, in the siRNA delivery via PTDs, arginine sequences have been shown to be more effective than their lysine analogues. (van Rossenberg, et al. 2004 *Gene Ther.* 11, 457-464.) Two different PTDMs were designed and studied. PTDM-1 is a hydrophilic molecule which is a mimic of oligoarginine peptide, having guanidinium functionalities along a polyoxanorbonene backbone (FIG. 44a). Besides, PTDM-2 is a block-copolymer having both hydrophilic, guanidinium and hydrophobic, phenyl moieties on the same backbone (FIG. 44b) and is inspired by the amphiphilic PTDs.

Figure 44:
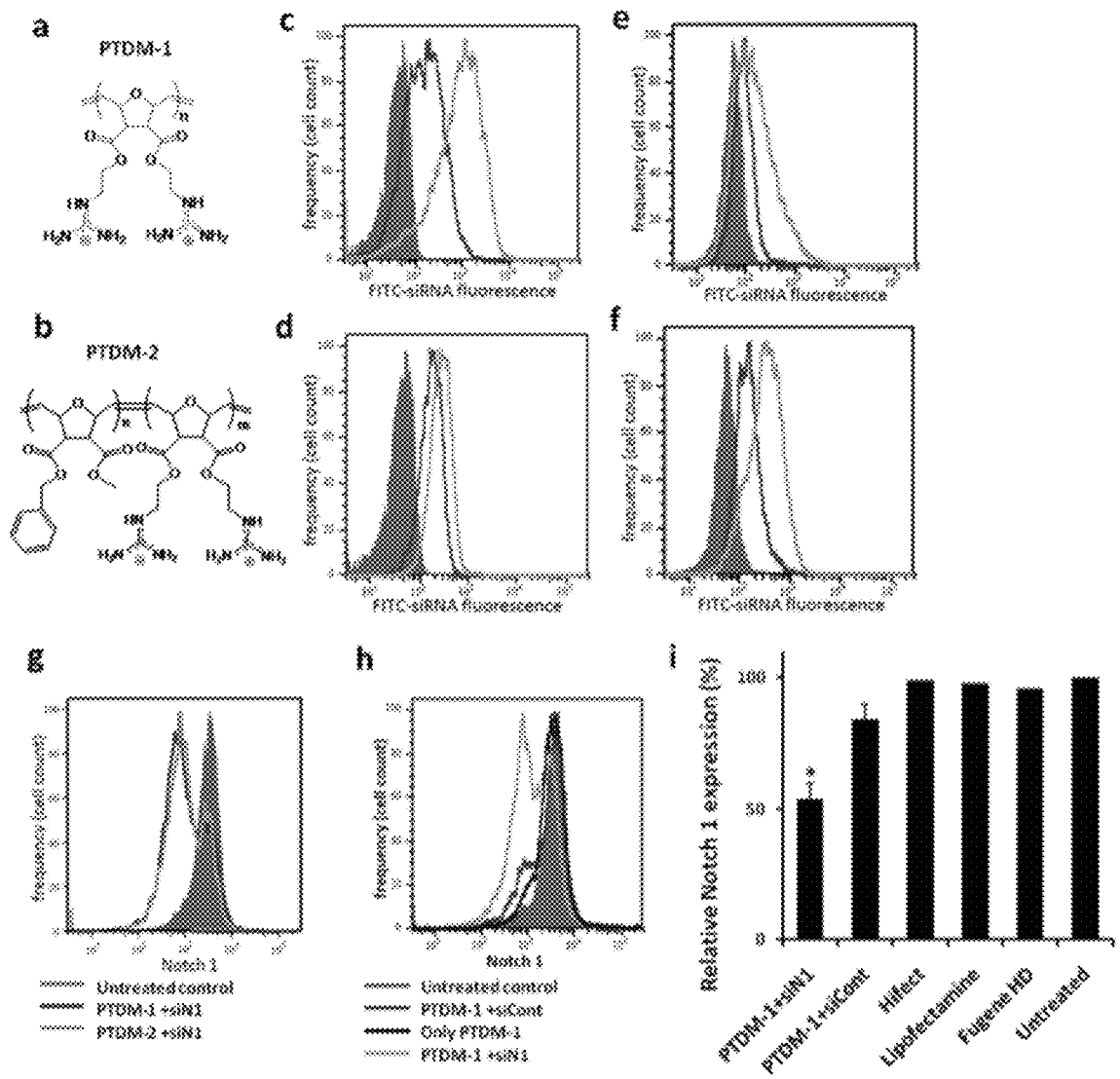
FIG. 44: siRNA delivery into Jurkat T cells. a) Chemical structure of PTDM-1, n=9. b) Chemical structure of PTDM-2, n=m=5. c) Flow cytometry analysis showing Jurkat T cells treated with PTDM-1 (1 µM)/FITC-siRNA (50 nM) complexes in complete media (blue curve) or serum free media (green curve) for 4 h and compared with untreated cells (red solid curve) d) Flow cytometry analysis showing Jurkat T cells treated with PTDM-2 (1.7 µM)/FITC-siRNA (50 nM) complexes in complete media (blue curve) or serum free media (green curve) for 4 h and compared with untreated cells (red solid curve) e) Flow cytometry analysis showing Jurkat T cells treated with PTDM-1 (1 µM)/FITC-siRNA (50 nM) complexes in serum-free media for 1 h at 4° C. (blue curve) or 37° C. (green curve) and compared with untreated cells (red solid curve). f) Flow cytometry analysis showing Jurkat T cells treated with PTDM-2 (1.7 µM)/FITC-siRNA (50 nM) complexes in serum-free media for 1 h at 4° C. (blue curve) or 37° C. (green curve) and compared with untreated cells (red solid curve). g) Flow cytometry analysis showing Jurkat T cells stained with fluorescent PE-anti Notch 1, 72 h after treatment with siRNA complexes; blue curve: cells treated with PTDM-1 (2 µM)/siN1 (100 nM) complexes, green curve: cells treated with PTDM-2 (3.5 µM)/siN1 (100 nM) complexes, red solid curve: untreated cells. h) Flow cytometry analysis showing Jurkat T cells stained with fluorescent PE-anti Notch 1, 72 h after the siRNA treatment; red curve: untreated cells, blue curve: cells treated with PTDM-1 (1.6 µM)/siCont (80 nM) complexes, black curve: cells treated with only PTDM-1 (1.6 µM), green curve: cells treated with PTDM-1 (1.6 µM)/siN1 (80 nM) complexes. i) Relative Notch 1 expression level in Jurkat T cells 72 h after treatment with PTDM-1/siN1 complexes, PTDM-1/siCont complexes, Hifect/siN1, Lipofectamine 2000/siN1 and Fugene HD/siN1 as analyzed by flow cytometry. Cells were treated with siRNA-carrier complexes in serum free medium for 4 h, then medium was exchanged with fresh complete growth medium (final siRNA concentration is 80 nM). Values and error bars represent the mean±SD of three independent experiments. *(P<0.01) of siN1 versus siCont delivered by PTDM-1.

Initially, to examine the ability of PTDMs to deliver siRNA into Jurkat T cells, a FITC-conjugated siRNA molecule was mixed with either PTDM-1 or PTDM-2 and resulting complexes were incubated on the cells in either serum-free or complete growth medium with 10% serum at 37° C. After washing the cells carefully with heparin solution, they were analyzed by a fluorescence activated cell sorter (FACS) (FIG. 44c, d). As shown in FIG. 44, both PTDMs are able to deliver siRNA in serum-free medium, single populations and narrow peaks indicate that PTDMs target the entire cell population and all the cells contain almost the same amount of siRNA. PTDM-1 worked much better than PTDM-2 in serum-free media; however, its efficiency was highly inhibited in the presence of serum (FIG. 44c). In the case of PTDM-2, there was no significant difference between serum-free and complete media conditions (FIG. 44d). This demonstrated the importance of aromatic groups on cargo stabilization properties of PTDM-2.

In addition to delivery experiments at 37° C., in order to examine the route of cell entry, PTDM/siRNA complexes were incubated on the cells at 4° C. at which most of the energy-dependent pathways are inhibited. Internalization at 4° C. also highlights the chance of cytosolic delivery of compounds and their availability to function. When Jurkat T cells were treated with PTDM-1/FITC-siRNA complexes at 4° C., resulted in no significant delivery of siRNA molecules (FIG. 44e), however PTDM-2 was able to deliver siRNA into the cells even at low temperature (FIG. 44f). Delivery efficiency of PTDM-2 was lower at 4° C. in comparison to at 37° C., but it can still deliver siRNA molecules to the entire cell population.

Experiments with FITC-tagged siRNA molecules demonstrated that both PTDMs delivered siRNA into the cells; however, they do not show the availability of siRNA molecules for gene silencing. To demonstrate the ability of PTDMs to deliver functional siRNA molecules, Notch 1 is chosen as a target in Jurkat T cells and human PBMCs. Notch 1 is a member of the Notch transmembrane receptors which are important regulators of cell-fate decisions and cell survival in many systems during embryogenesis and post-natal development, including the immune system. (Arta-vanis-Tsakonas, et al. 1999 Science, 284, 770-776; Osborne, et al. 2007 Nat. Rev. Immunol. 7, 64-75.)

In order to evaluate the function of siRNA molecules, Jurkat T cells were treated with complexes of siRNA to Notch 1 (siN1) and either PTDM-1 or PTDM-2 in serum free media for 4 h, then protein expression level was analyzed at 72 h by FACS after staining intracellular domain of Notch 1 with fluorescent anti-Notch 1 (FIG. 44g). Efficient down regulation was observed at Notch-1 protein levels in Jurkat T cells treated with both PTDM-1/siN1 and PTDM-2/siN1 complexes. Both PTDMs performed with the same efficiency, no significant difference was observed. Furthermore, down regulation efficiencies of PTDM-1 and commercially available cationic lipids, Lipofectamine 2000, Hifect, and Fugene HD, were compared in Jurkat T cells (FIG. 44i). There was no silencing activity in the cells treated with cationic lipid based formulations. On the other hand, a 50% down regulation observed in the cells treated with complexes of 80 nM siN1 and 1.6 µM PTDM-1. In addition, the cells were also treated with a scrambled control siRNA (siCont) and only PTDM-1, to show that the decrease on Notch 1 protein levels is mediated by Notch 1 specific siRNA (FIG. 44h).

Figure 48:
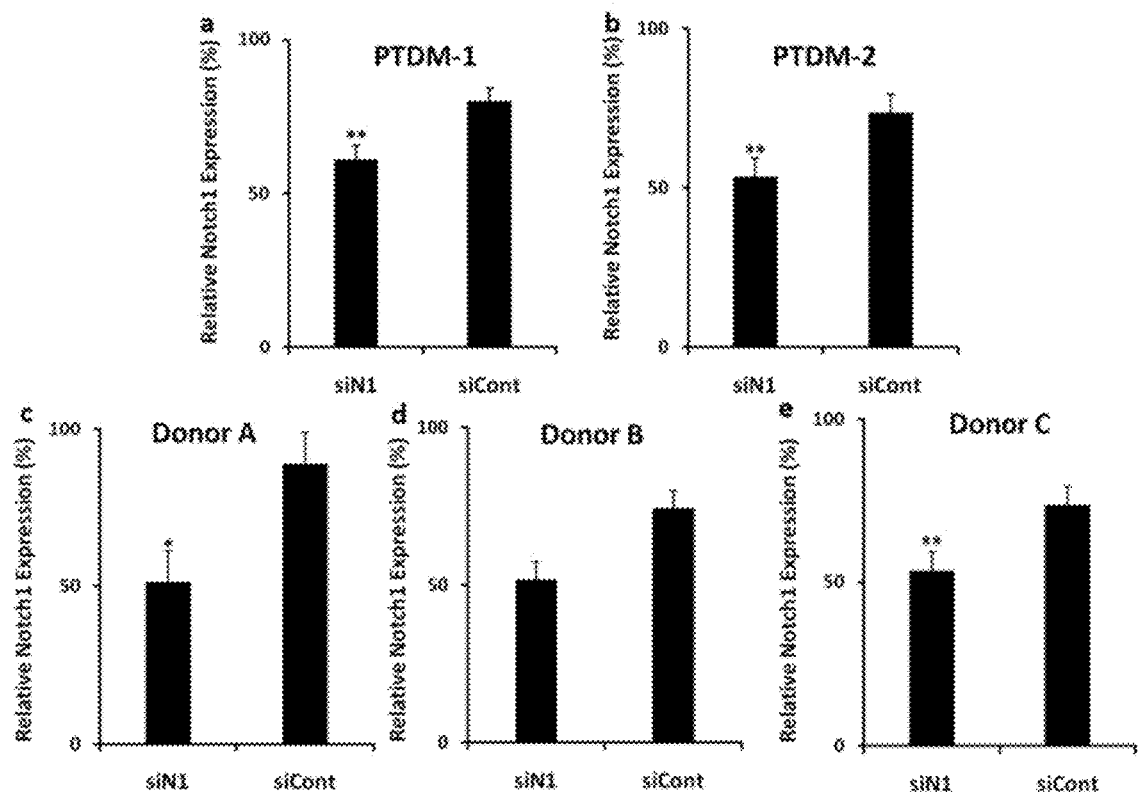
FIG. 48: Relative Notch 1 expression level in PBMCs. a) Relative Notch 1 expression level in PBMCs 72 h after treatment with PTDM-1/siN1 and PTDM-1/siCont (final siRNA concentration is 60 nM). b) Relative Notch 1 expression level in PBMCs 72 h after treatment with PTDM-2/siN1 and PTDM-2/siCont (Final siRNA concentration is 60 nM). c, d, e) Relative Notch 1 expression level in PBMCs from three different donors (donor A, B, and C) 72 h after treatment with with PTDM-2/siN1 and PTDM-2/siCont (Final siRNA concentration is 60 nM). Cells were treated with PTDM/siRNA complexes in serum free medium for 4 h, then medium was exchanged with fresh complete growth medium, and cells were transferred to anti-CD3/CD28 coated wells for activation. Protein level was analyzed by flow cytometry 72 h after the treatment by flow cytometry. Values and error bars represent the mean±SD of three independent experiments. *(P<0.05) of siN1 versus siCont delivered by PTDM-2. **(P<0.01) of siN1 versus siCont delivered by PTDM-1 or PTDM-2.

Primary cells are also known as a problematic cell type in terms of intracellular delivery of macromolecules. Next, the Notch 1 down regulation in human PBMCs by PTDM/siRNA complexes was evaluated. PBMCs were cultured the day before the treatment in order to separate and work with the T cell-enriched lymphocytes. Initially, suspension part of PBMCs were treated with PTDM/siRNA complexes in serum free media for 4 h, then media was replaced with complete growth media and the cells were stimulated for 72 h to up-regulate Notch 1. At the indicated time point, cells were harvested and intracellular Notch 1 was stained using fluorescent anti-Notch 1, then analyzed by FACS. Both PTDM-1 and PTDM-2 were used to deliver 60 nM siRNA to PBMCs from the same donor and both PTDMs successfully demonstrated approximately 50% down regulation on Notch 1 protein levels (FIG. 48a, b). Also, experiments were performed with scrambled siRNA as a negative control and there is a significant difference (p<0.01) between siN1 and siCont treated cells which proved that Notch 1 knockdown is only mediated by siN1. Furthermore, in order to establish the universality of PTDMs in human PBMCs, delivery efficiency of PTDM-2 was demonstrated in PBMCs from three different donors (FIG. 48c-e). PTDM-2 showed similar knockdown efficiencies among different donors with a small variance.

Figure 45:
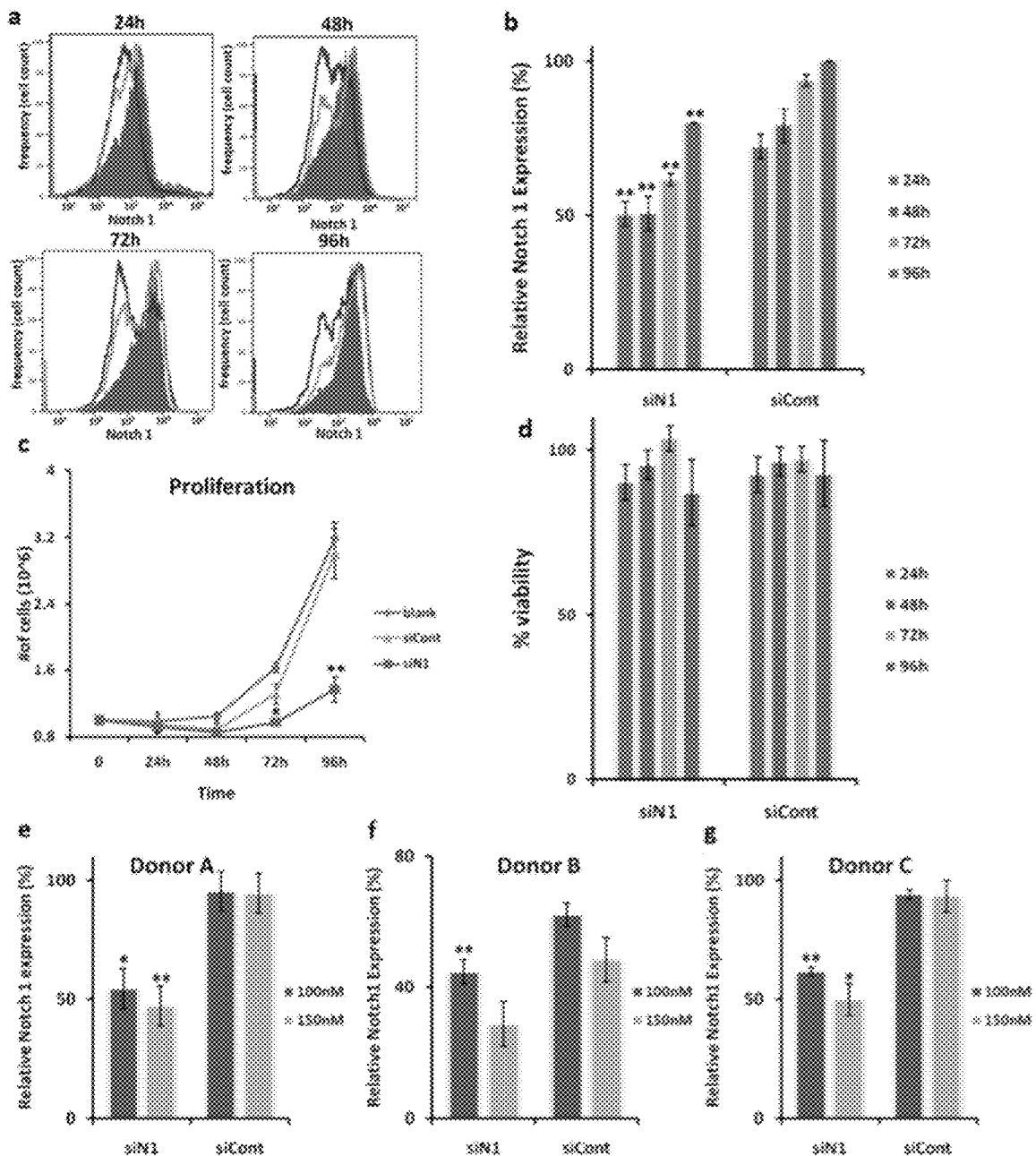
FIG. 45: Time dependent down regulation of Notch 1 by PTDM-2/siN1. a) Flow cytometry analysis showing PBMCs stained with fluorescent PE-anti Notch 1, 24 h, 48 h, 72 h or 96 h after treatment with siRNA complexes; blue curve: cells treated with PTDM-2 (3.5 µM)/siN1 (100 nM) complexes, green curve: cells treated with PTDM-2 (3.5 µM)/siCont (100 nM) complexes, red solid curve: untreated cells. b) Relative Notch 1 expression levels in PBMCs 24 h, 48 h, 72 h or 96 h after treatment with PTDM-2 (3.5 µM)/siN1 (100 nM) or PTDM-2 (3.5 µM)/siCont (100 nM) complexes. c) Cell proliferation assay. Equal numbers of PBMCs were seeded and treated with either PTDM-2 (3.5 µM)/siN1 (100 nM) or PTDM-2 (3.5 µM)/siCont (100 nM) complexes. Cell proliferation was measured by cell counting with a hemacytometer at indicated time points. d) 7-AAD viability test. PTDM-2 (3.5 µM)/siN1 (100 nM) or PTDM-2 (3.5 µM)/siCont (100 nM) treated cells were stained with 7-Amino-Actinomycin D (7-AAD) at indicated time points after the treatment. e-f-g) Relative Notch 1 expression level in PBMCs from three different donors (Donor A, B and C) 72 h after treatment with PTDM-2/siN1 and PTDM-2/siCont as a final siRNA concentration of 100 nM or 150 nM. Cells were treated with PTDM/siRNA complexes in complete media for 4 h, and then cells were transferred to anti-CD3/CD28 coated wells. Protein level was analyzed at 72 h after the treatment by flow cytometry. Values and error bars represent the mean±SD of three independent experiments. *(P<0.05) of siN1 versus siCont delivered by PTDM-2.**(P<0.01) of siN1 versus siCont delivered by PTDM-2.

In addition, to examine the stability of PTDM/siRNA complexes and their ability to deliver functional siRNA molecules in the presence of serum, PBMCs were treated with PTDM/siRNA complexes in complete growth medium without further media change. Both PTDM-1 and PTDM-2 performed efficiently in serum-free condition, however in the presence of serum, only PTDM-2 was able to deliver functional siRNA into the cells (FIG. 45).

For further analysis, PBMCs were treated with PTDM-2/siRNA complexes in complete media to knockdown Notch 1. Notch 1 protein levels were monitored for four days in the cells treated with either PTDM-2/siN1 or PTDM-2/siCont complexes (FIG. 45). At least 50% decrease on Notch 1 protein level was observed in the cells treated with the mixture of 100 nM siRNA and 3.5 µM PTDM-2 at 24 h, RNAi response showed a slow decay after 72 h (FIG. 45a, b). As reported earlier, it is known that Notch 1 has an important role on cell-fate decisions. Therefore, to determine whether down regulation of Notch 1 expression by siRNA has an effect on cell growth of PBMCs, proliferation of cells was also analyzed (FIG. 45c). Down regulation of Notch 1 expression caused significant cell growth inhibition in PBMCs; while untreated and scrambled siRNA treated cells were in their logarithmic growth phase on the day four. Furthermore, one of the major limitations in intracellular delivery to primary cells is the toxicity of delivery tools. In order to investigate the cytotoxic effect of PTDM-2/siRNA treatment, cells were stained with 7-Amino-Actinomycin D (7-AAD) and analyzed by FACS. Neither PTDM-2/siN1 nor PTDM-2/siCont treatments affected the cell viability at the concentrations used (FIG. 45d).

Knockdown efficiency of PTDM-2/siRNA complexes was also examined at different concentrations of siRNA and among different three donors in the presence of serum (FIG. 45e-g). Increasing the siRNA concentration from 100 nM to 150 nM did not affect the efficiency of knockdown significantly, and this was consistent among all three donors.

Moreover, Notch 1 has been shown to play an important role in the development and differentiation of peripheral T cells. Activated CD4+ T cells can further differentiate into T helper type 1 ($T_H1$) or $T_H2$ cells. $T_H1$ and $T_H2$ cells produce specific cytokines during their terminal maturation. For instance, IFN-γ, tumor necrosis factor is one of the cytokines which is dominantly expressed by $T_H1$ cells. It has been reported earlier, the expression of $T_H1$ transcription factor T-bet is both necessary and sufficient to drive $CD4^+$ $T_H1$ differentiation and expression of the cytokine IFN-γ. (Minter, et al. 2005 Nat. Immunol. 6, 680-688.) siRNA molecules are great tools to analyze the function of Notch 1 in primary T cells in a gene-specific manner which was limited earlier due to lack of efficient and safe delivery tools.

Figure 46:
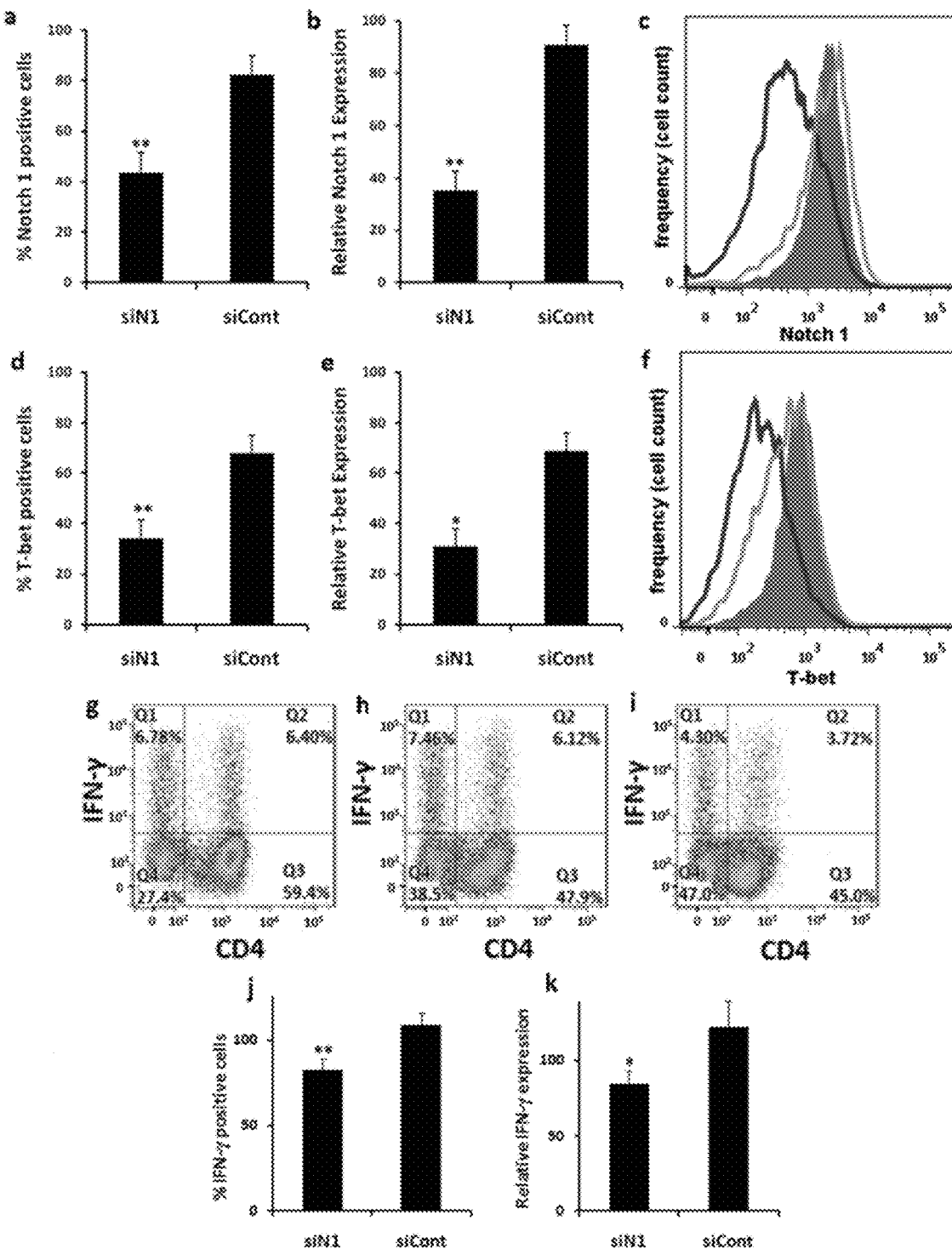
FIG. 46: Effect of Notch 1 down regulation by siRNA on CD4$^+$T cell differentiation at 72 h. a) Percentage of Notch 1 expressing $T_H1$ polarized CD4$^+$T cells 72 h after treatment with PTDM-2/siN1 or PTDM-2/siCont. b) Relative Notch 1 expression in $T_H1$ polarized CD4$^+$T cells 72 h after treatment with PTDM-2/siN1 or PTDM-2/siCont. c) Flow cytometry analysis showing $T_H1$ polarized CD4$^+$T cells stained with fluorescent PE-anti Notch 1 72 h after treatment with siRNA complexes; blue curve: PTDM-2/siN1 treated cells, green curve: PTDM-2/siCont, red solid curve: untreated cells. d) Percentage of T-bet expressing $T_H1$ polarized CD4$^+$T cells 72 h after treatment with PTDM-2/siN1 or PTDM-2/siCont. e) Relative T-bet expression in $T_H1$ polarized CD4$^+$T cells 72 h after treatment with PTDM-2/siN1 or PTDM-2/siCont. f) Flow cytometry analysis showing $T_H1$ polarized CD4$^+$T cells stained with fluorescent Alexa Fluor 647 anti-T-bet 72 h after treatment with siRNA complexes; blue curve: PTDM-2/siN1 treated cells, green curve: PTDM-2/siCont, red solid curve: untreated cells. g-i) Flow cytometry analysis showing $T_H1$ polarized CD4$^+$T cells stained with fluorescent APC-anti IFN-γ 72 h after treatment with siRNA complexes; g) untreated cells, h) PTDM-2/siCont treated cells, i) PTDM-2/siN1 treated cells. j) Percentage of IFN-γ expressing $T_H1$ polarized CD4$^+$T cells 72 h after treatment with PTDM-2/siN1 or PTDM-2/siCont. k) Relative IFN-γ expression in $T_H1$ polarized CD4$^+$T cells 72 h after treatment with PTDM-2/siN1 or PTDM-2/siCont. Values and error bars represent the mean±SD of three independent experiments. *(P<0.05) of siN1 versus siCont delivered by PTDM-2. **(P<0.01) of siN1 versus siCont delivered by PTDM-2.
Figure 47:
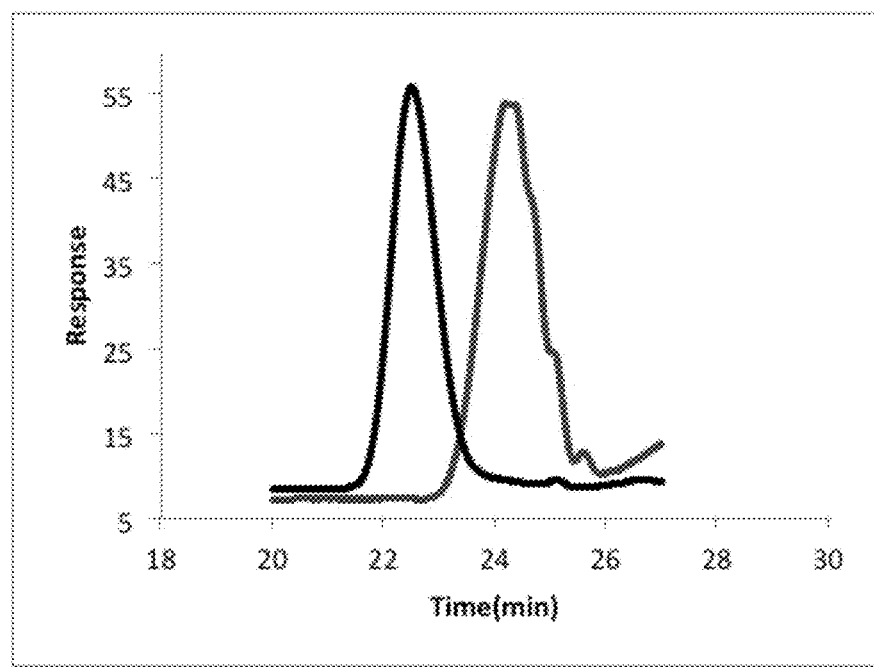
Figure 49:
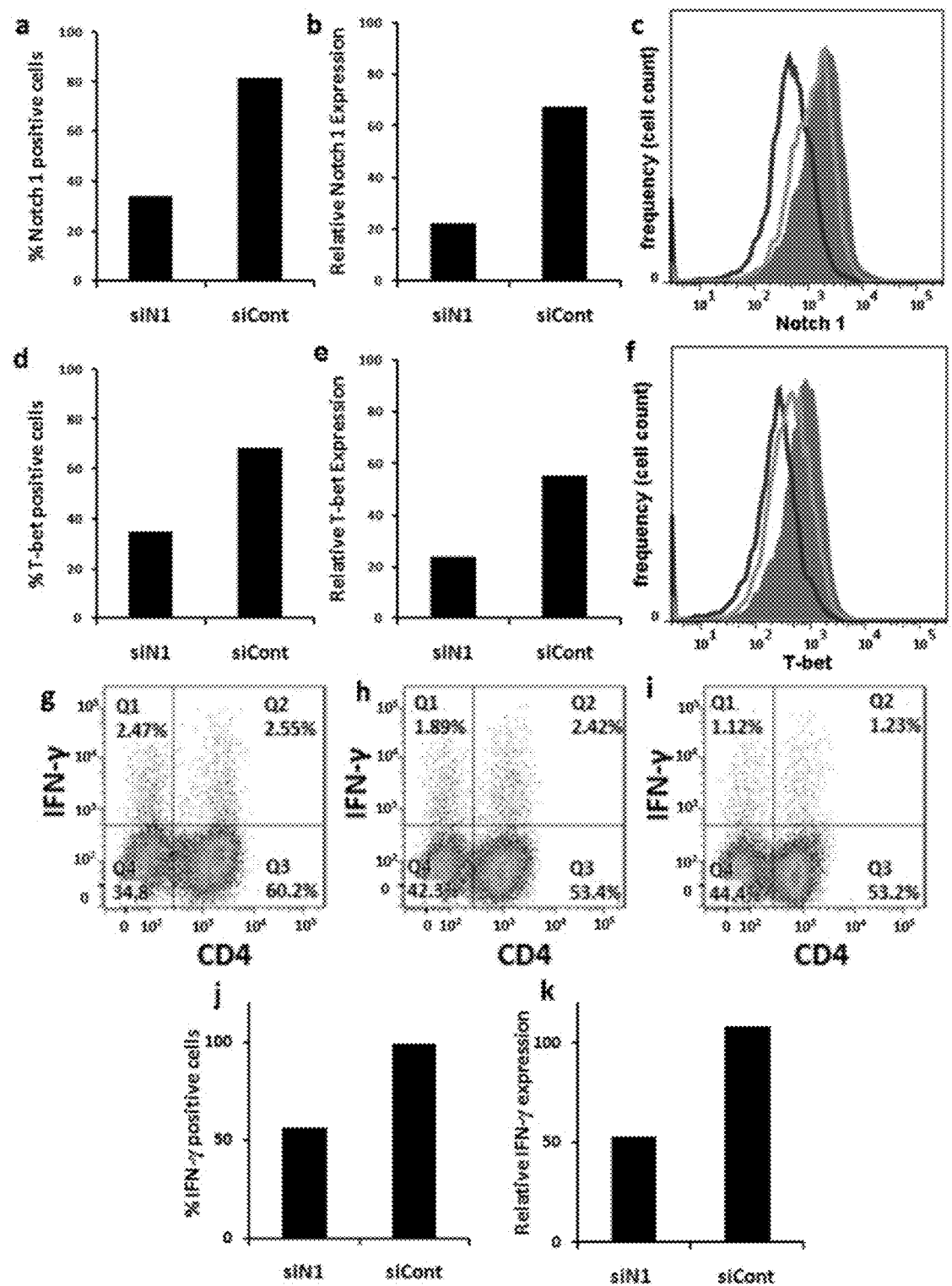
FIG. 49: Effect of Notch 1 down regulation by siRNA on CD4$^+$T differentiation at 48 h. a) Percentage of Notch 1 expressing $T_H1$ polarized CD4$^+$T cells 48 h after treatment with PTDM-2/siN1 or PTDM-2/siCont. b) Relative Notch 1 expression in $T_H1$ polarized CD4$^+$T cells 48 h after treatment with PTDM-2/siN1 or PTDM-2/siCont. c) Flow cytometry analysis showing $T_H1$ polarized CD4$^+$T cells stained with fluorescent PE-anti Notch 1 48 h after treatment with siRNA complexes; blue curve: PTDM-2/siN1 treated cells, green curve: PTDM-2/siCont, red solid curve: untreated cells. d) Percentage of T-bet expressing $T_H1$ polarized CD4$^+$T cells 48 h after treatment with PTDM-2/siN1 or PTDM-2/siCont. e) Relative T-bet expression in $T_H1$ polarized CD4$^+$T cells 48 h after treatment with PTDM-2/siN1 or PTDM-2/siCont. f) Flow cytometry analysis showing $T_H1$ polarized CD4$^+$T cells stained with fluorescent Alexa Fluor 647 anti-T-bet 48 h after treatment with siRNA complexes; blue curve: PTDM-2/siN1 treated cells, green curve: PTDM-2/siCont, red solid curve: untreated cells. g-i) Flow cytometry analysis showing $T_H1$ polarized CD4$^+$T cells stained with fluorescent APC-anti IFN-γ 48 h after treatment with siRNA complexes; (g) untreated cells, (h) PTDM-2/siCont treated cells, (i) PTDM-2/siN1 treated cells. j) Percentage of IFN-γ expressing $T_H1$ polarized CD4$^+$T cells 48 h after treatment with PTDM-2/siN1 or PTDM-2/siCont. k) Relative IFN-γ expression in $T_H1$ polarized CD4$^+$T cells 48 h after treatment with PTDM-2/siN1 or PTDM-2/siCont. Results are representative of two independent replicates.
Figure 50:
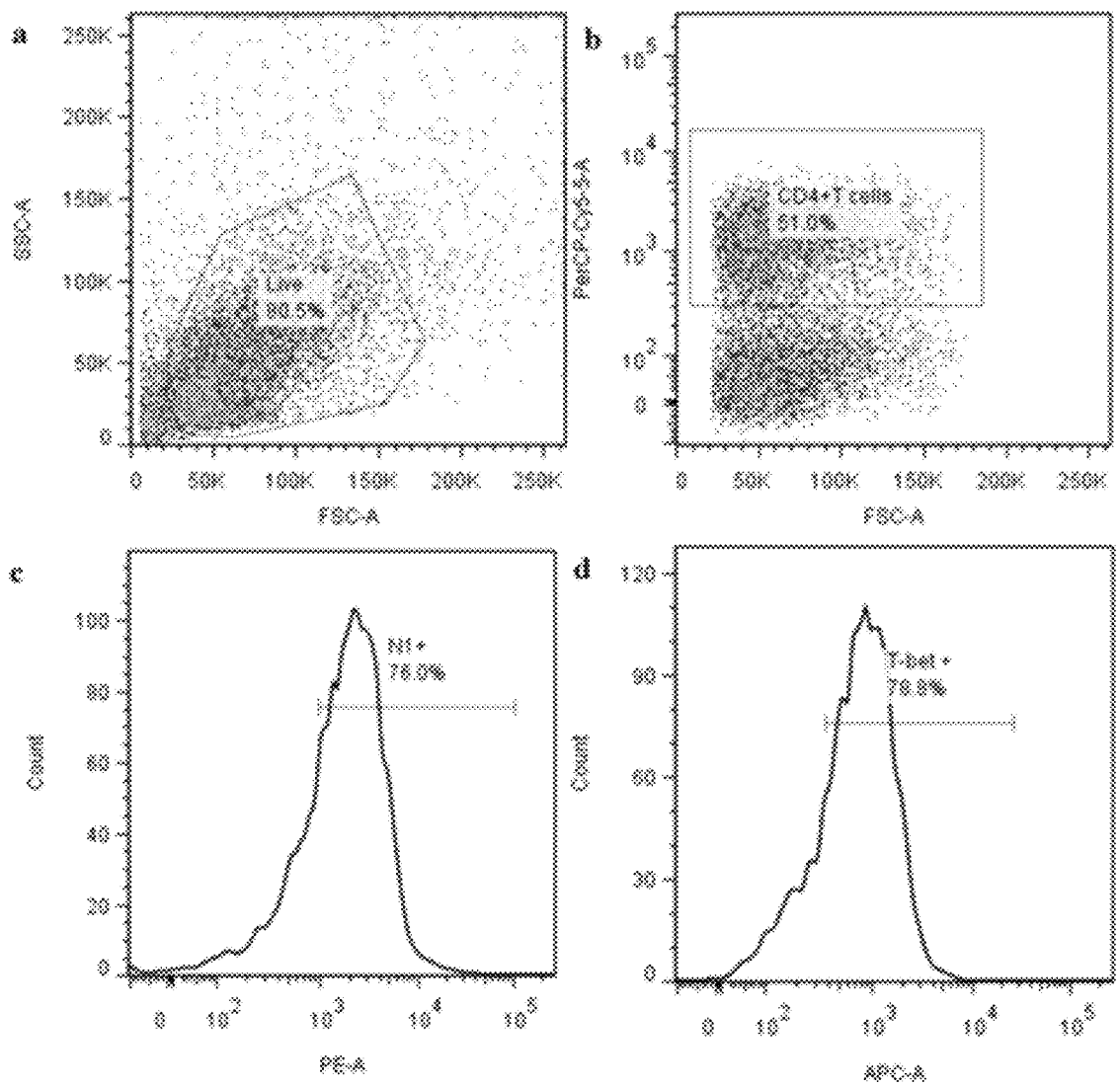
FIG. 50: Untreated human PBMCs were polarized under $T_H1$ conditions for 48 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.
Figure 51:
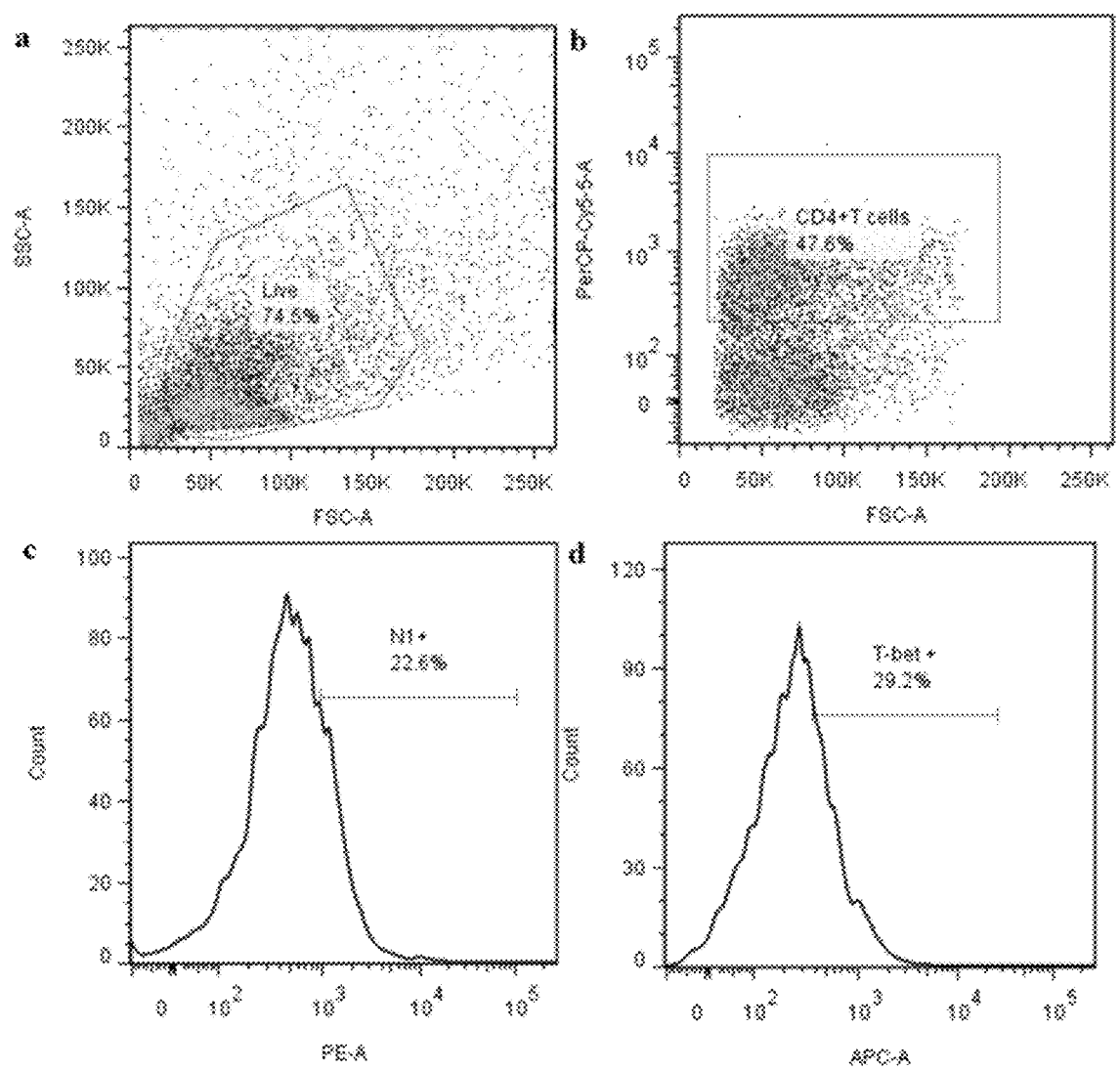
FIG. 51: PTDM-2/siN1 treated human PBMCs were polarized under $T_H1$ conditions for 48 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.
Figure 52:
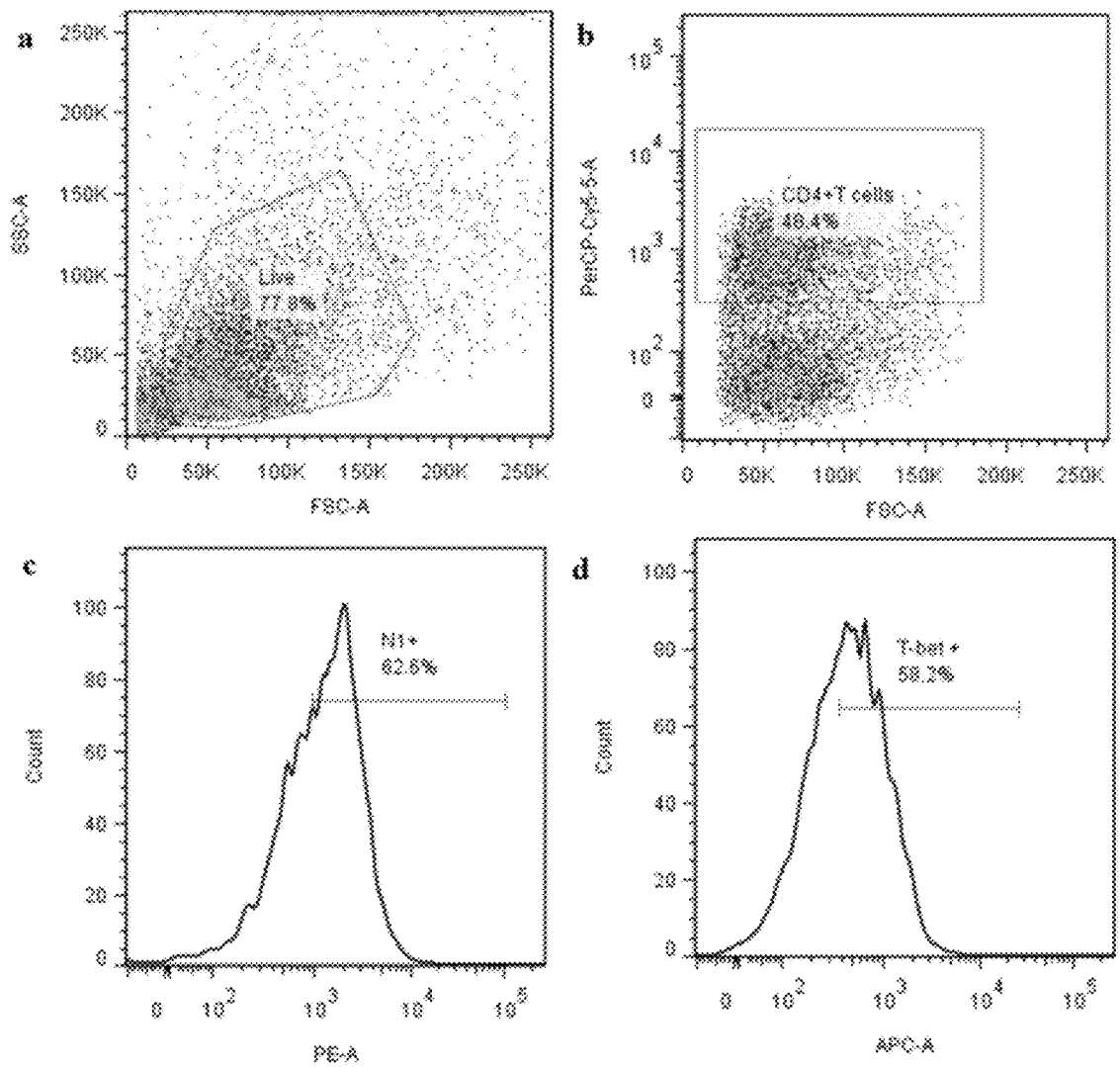
FIG. 52: PTDM-2/siCont treated human PBMCs were polarized under $T_H1$ conditions for 48 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.
Figure 53:
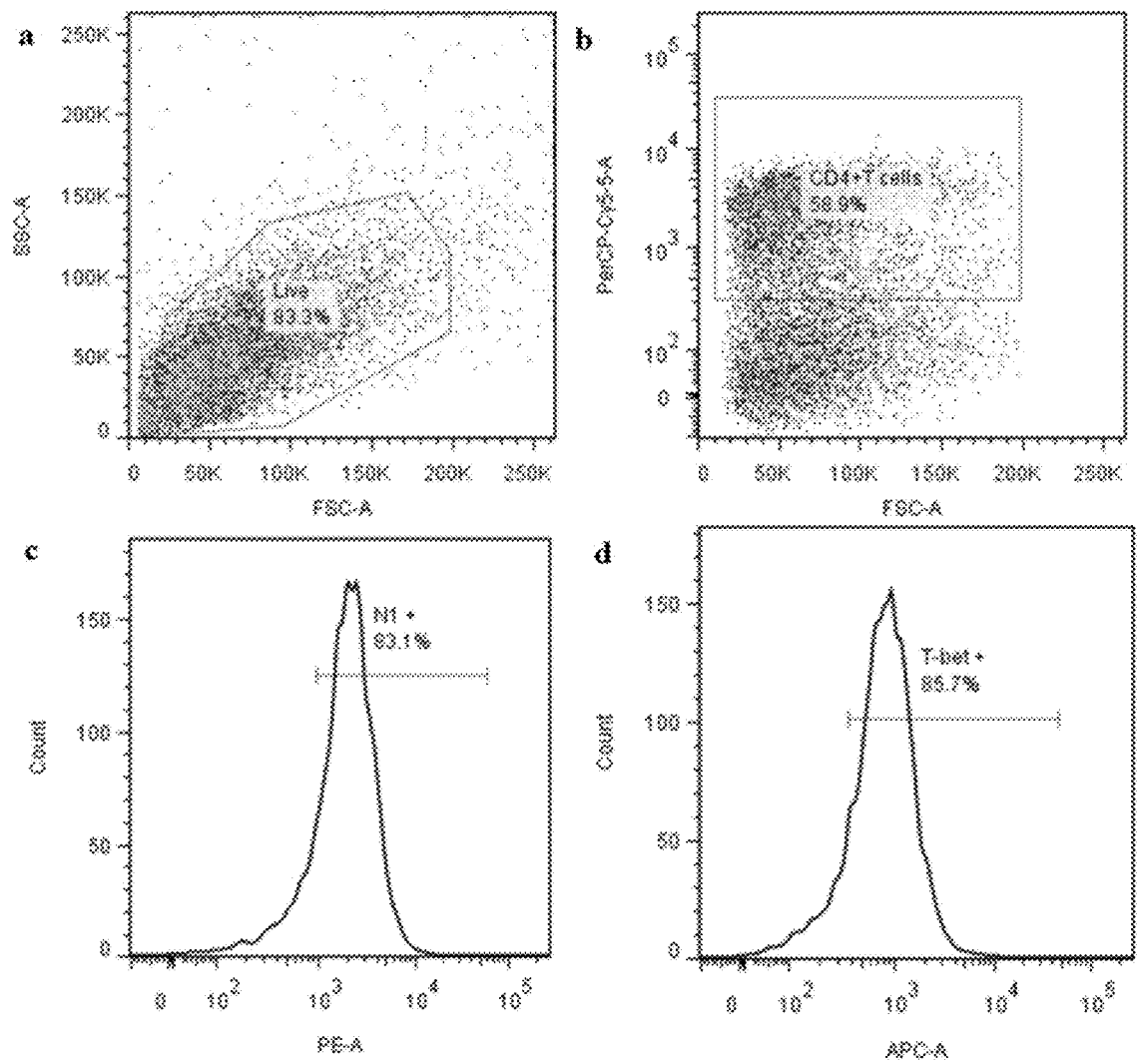
FIG. 53: Untreated human PBMCs were polarized under $T_H1$ conditions for 72 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.
Figure 54:
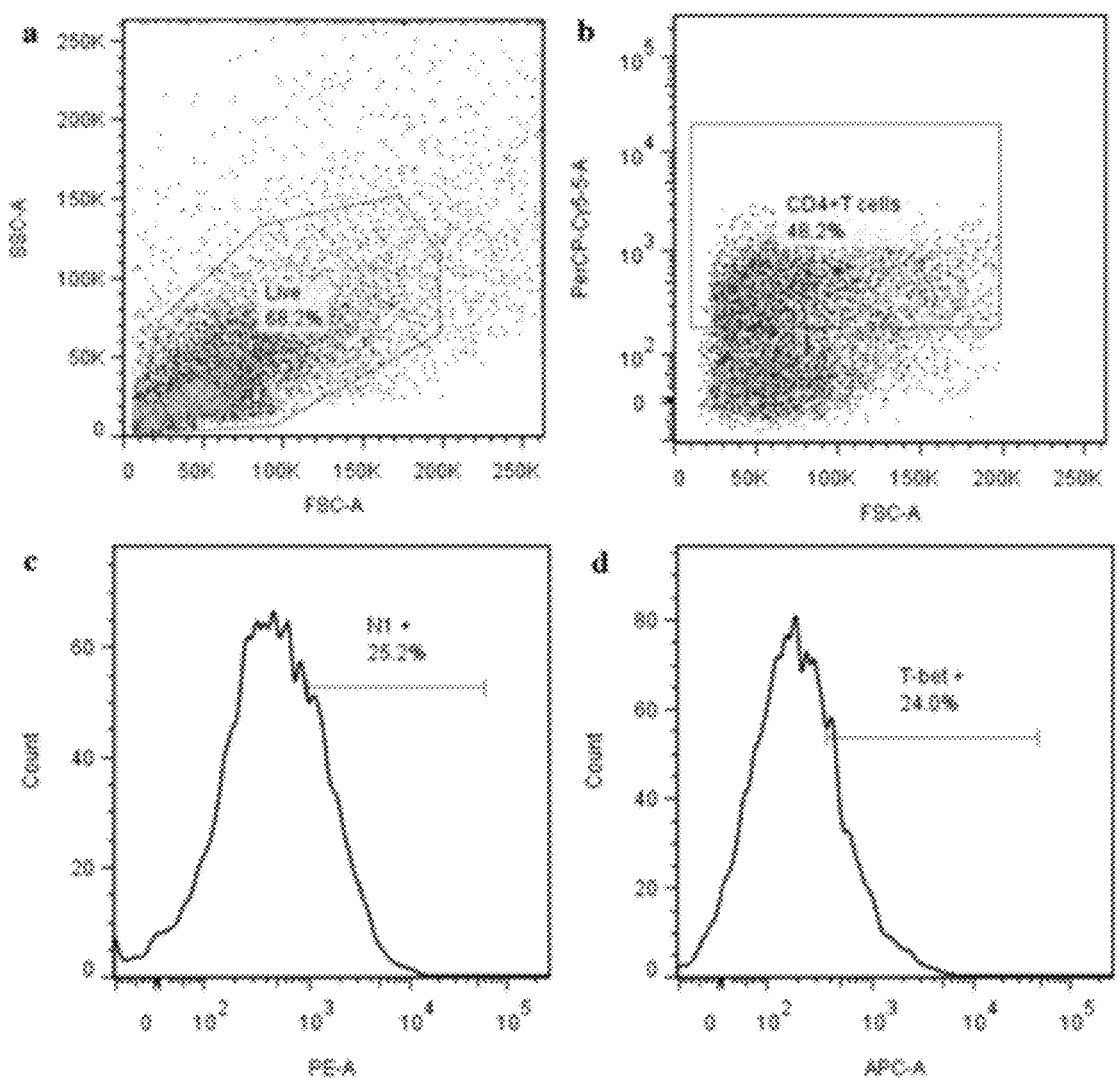
FIG. 54: PTDM-2/siN1 treated human PBMCs were polarized under $T_H1$ conditions for 72 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.
Figure 55:
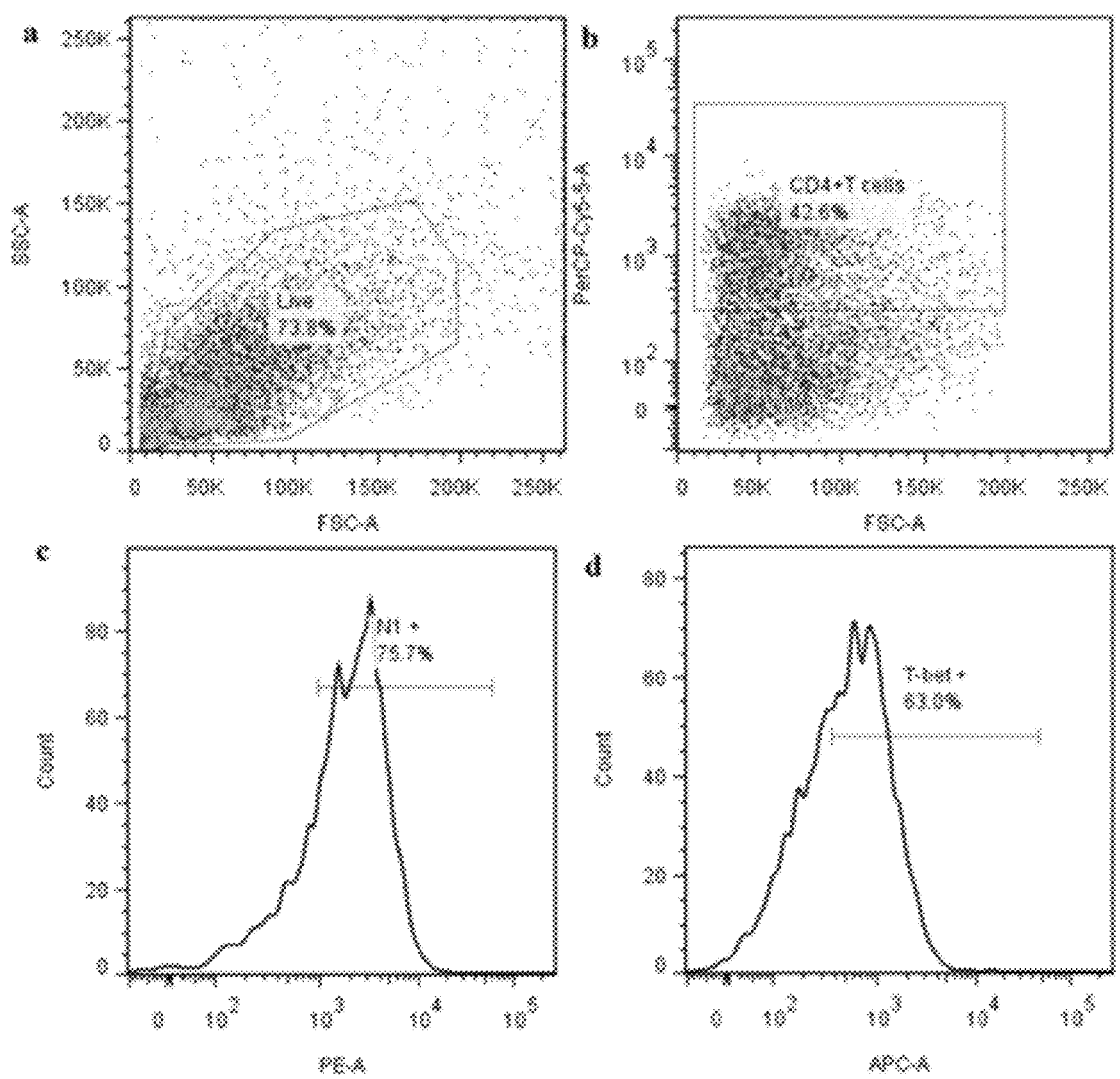
FIG. 55: PTDM-2/siCont treated human PBMCs were polarized under $T_H1$ conditions for 72 h. a) Live population was gated on side scatter (SSC) and forward scatter (FCS) dot plot. b) CD4$^+$T cells were gated on live population according to their reactivity to PerCP-Cy5.5-labeled anti-CD4. c) Notch 1 expressing CD4$^+$T cells were identified according to their reactivity to PE-labeled anti-Notch 1. d) T-bet expressing CD4$^+$T cells were identified according to their reactivity to eFluor 660-labeled anti-T-bet.

To investigate the effect of Notch 1 expression on $CD4^+T$ cell differentiation under $T_H1$ polarization conditions; first PBMCs were treated with PTDM-2/siN1 or PTDM-2/siCont for 4 hours, then the cells were polarized with interleukin-12 (IL-12) and anti-interleukin-4 (IL-4 mAb), then stimulated with plate bound anti-CD3 and anti-CD28. At 48 h (FIG. 49) or 72 h (FIG. 46) time points, the $CD4^+T$ cells were identified according to their reactivity to anti-CD4 monoclonal antibody. In $CD4^+T$ cells, Notch 1 and T-bet were also analyzed by anti-Notch 1 and anti-T-bet monoclonal antibodies, respectively. In addition, the cells were restimulated 6 h with Brefeldin A and stained for IFN-γ which is a signature cytokine of $T_H1$ polarized cells. At the end, cells were analyzed by FACS which is a powerful technique to determine both the percentage of cells undergoing gene-silencing and the amounts of protein downregulation in the cells of interest. (Chan, et al. 2005 *Cytometry Part A*, 69A, 59-65.)

At 48 h time point, the down regulation of Notch 1 by siN1 inhibited the expression of T-bet in CD4+T cells (FIG. 49*d-f*), also inhibited the IFN-γ production compared to untreated and siCont treated cells (FIG. 49*j-k*). However, at 48 h time point there was a low level of IFN-γ production in the untreated cells as well (FIG. 49*g-i*). Further, the cells were harvested at 72 h time point at which more IFN-γ production was observed in control groups (untreated and siCont treated cells) in accordance with their higher expression of Notch 1 (FIG. 46*a-c*) and T-bet (FIG. 46*d-f*). IFN-γ production in siN1 treated cells was significantly lower than control groups (FIG. 46*j-k*).

One of the major limitations to use of RNA interference to study unknown gene functions in primary cells is the inefficient delivery strategies. Here, the system is based on PTDMs generated by ROMP for a safe and efficient delivery of siRNA. PTDM-1, which is a mimic of polyarginine, successfully delivered functional siRNA molecules into hard to transfect cell types, Jurkat T cells and PBMCs, even though it has been reported that homopolymers of arginines are not able to deliver siRNA via non-covalent complexation. (Kim, et al. 2006 *Mol. Ther.* 14, 343-350; Kumar, et al. 2008 *Cell* 134, 577-586.) Furthermore, in order to test the effect of hydrophobicity in addition to arginine functionalities on the carrier efficiency, PTDM-2 was generated using hydrophobic phenyl and hydrophilic guanidinium functionalities. There was no significant difference on delivery efficiencies of the PTDM-1 and PTDM-2 in the absence of serum. On the other hand, PTDM-2 showed a superior efficiency in the presence of serum where PTDM-1 did not work at all. This demonstrates that the introduction of hydrophobic groups in the structure of PTDMs improved the stability of complexes and also made them better candidates for in vivo experiments. Down regulation Notch 1 in Jurkat T cells and primary human PBMCs is chosen as a model system. Notch 1 is known to have an important role in T cell development and differentiation. Therefore, the role of Notch 1 on cell proliferation and T cell differentiation in human PBMCs was successfully demonstrated via silencing Notch 1 by novel PTDM-based siRNA delivery system.

Experimental

General

Maleic anhydride, furan, 4-dimethyl aminopyridine (DMAP), 1-(3-Dimethylaminopropyl)-3-ethylcarbodiimide hydrochloride (EDC), methanol, 1,3-Di-Boc-2-(2-hydroxyethyl)guanidine, benzyl alcohol, ethylvinyl ether and trifluoroacetic acid (TFA) were obtained as reagent grade from Aldrich, Fluka or Acros and used as received.

3rd generation Grubbs catalyst (Dichloro-di(3-bromopyridino)-N,N'-Dimesitylenoimidazolino-Ru=CHPh; G3) was synthesized as described previously by Grubbs et al. (Love, et al. 2002 *Angew. Chem. Int. Ed.* 41, 4035-4037.) The HPLC grade solvents ethyl acetate, pentane and hexane were purchased from Aldrich, Fisher Scientific or Acros and used as received. Tetrahydrofuran (THF) (HPLC grade, Fisher Scientific) was distilled from sodium/benzophenone under nitrogen. Dichloromethane (DCM) (HPLC grade, Fisher Scientific) was distilled from $CaH_2$ under nitrogen.

Gel permeation chromatography (THF, calibrated with polystyrene standards, toluene as flow marker, 50° C.) was measured on a PL50 GPC setup (Polymer Laboratories, Amherst, Mass.) with a PL Gel 5 μm pre-column and two 10 μm analytical Mixed-D columns (Polymer Laboratories, Amherst, Mass.). NMR spectra were recorded on a Bruker DPX300 spectrometer (Bruker, Madison, Wis.). High resolution mass spectra were obtained from a JEOL JMS 700 instrument (JEOL, Peabody, Mass.); Matrix Assisted Laser Desorption and Ionization Time of Flight Mass Spectra (MALDI-TOF MS) were measured on a Bruker Daltonics Reflex III (Bruker, Madison, Wis.).

Monomer Synthesis

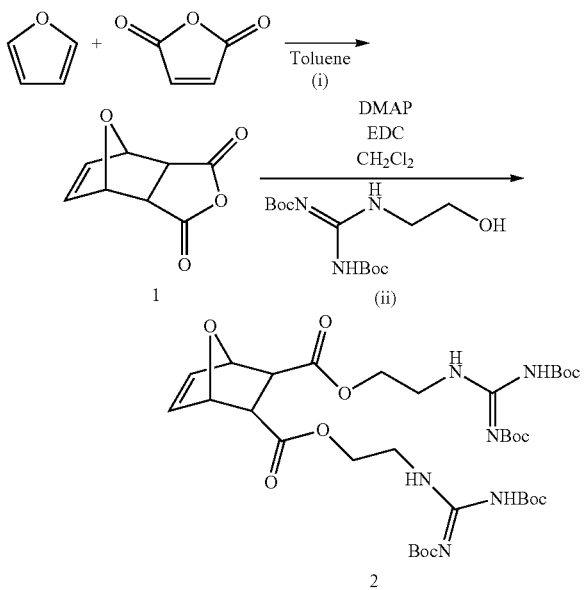

Scheme 8: Synthesis of monomer 2.

Synthesis of 2: (i) Maleic anhydride (100 g, 1.02 mol) was dissolved in 1 L toluene, 150 mL (140.7 g, 2.05 mol) furan was added, and then the solution was stirred for 3 days according to the literature. The product (1) was then filtered, washed with hexanes and dried under vacuum. A colorless powder was obtained. Spectroscopic data and yield are the same as reported earlier. (Mantovani, et. al. 2005 *J. Am. Chem. Soc.* 127, 2966-2973.) (ii) The same procedure was followed as Lienkamp et al. with minor modifications. (Lienkamp, et al. 2008 *J. Am. Chem. Soc.* 130, 9836-9843.) Compound 1, 10 mol % DMAP and 1.9 equivalents of the 1,3-Di-Boc-2-ethyl guanidine were dissolved in DCM. After all components dissolved, the solution was cooled down to 0° C. in an ice bath, and 1 equivalent of EDC was added. The solution was stirred over night. The reaction mixture was diluted with DCM and washed with 10% $KHSO_4$ (3×25 mL) and sat. $NaHCO_3$ solution (3×25 mL). Next, the organic phase was dried over $Na_2SO_4$ and filtered. The volume of solution was reduced by vacuum evaporation, and the product was run through a short alumina column. Vacuum evaporation of the solvent yielded the pure product 2. The yield ranged from ~80%.

2: colorless solid. $^1$H-NMR (300 MHz, $CDCl_3$): δ=11.50 (2H, s), 8.55 (2H, s), 6.42 (2H, s), 5.3 (2H, d, J=6.0 Hz), 4.26

(4H, m), 3.71 (4H, m), 2.85 (2H, s), 1.49 (18H, s), 1.48 (18H, s) $^{13}$C-NMR (75 MHz, CDCl$_3$): δ=171.3, 163.4, 156.3, 153.1, 136.7, 83.2, 80.9, 63.6, 46.7, 39.4, 28.3, 28.2, HR-MS (FAB): calc. 754.37, found 755.3.

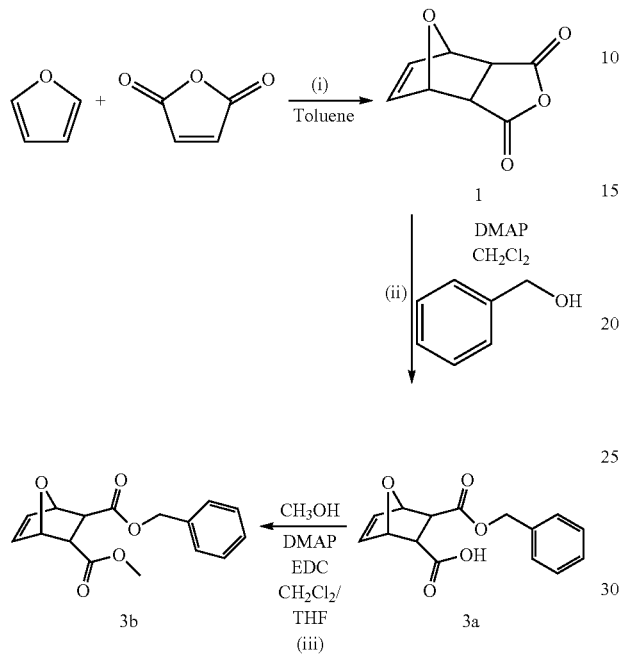

Synthesis of 3a: Compound 1 and 1.5 equivalents of the benzyl alcohol were dissolved in DCM, and the reaction mixture was stirred 3 days after the addition of 10 mol % DMAP. The product 3a precipitated as a result of reaction in DCM, the precipitate was filtered and vacuum evaporation of residual solvent yielded the pure product 3a. The yield ranged from ~70%.

3a: Colorless Solid. $^1$H-NMR (300 MHz, DMSO-d6): δ=12.48 (1H, s), 7.41 (5H, s), 6.46 (2H, d, J=3.9 Hz), 5.11 (2H, m), 5.02 (2H, m), 2.78 (2H, d, J=2.7 Hz).

Synthesis of 3b: One equivalent of compound 3a, two equivalents of methanol and 10% DMAP was dissolved in 1:1 mixture of DCM: THF. After all components dissolved, the solution was cooled down to 0° C. in an ice bath, and one equivalent of EDC was added. The solution was stirred over night. All the solvent was evaporated and reaction mixture was dissolved in DCM, then washed with 10% KHSO$_4$ (3×25 mL) and sat. NaHCO$_3$ solution (3×25 mL). Next, the organic phase was dried over Na$_2$SO$_4$ and filtered. The volume of solution was reduced by vacuum evaporation, and the product was run through a short alumina column. Vacuum evaporation of the solvent yielded the pure product 3b. The yield ranged from ~80%.

3b: colorless oil. $^1$H-NMR (300 MHz, DMSO-d6): δ=7.35 (5H, m), 6.45 (2H, s), 5.13 (2H, m), 5.06 (2H, m), 3.44 (3H, s), 2.84 (2H, m). $^{13c}$-NMR (75 MHz, DMSO-d6): δ=172.1, 171.6, 137.1, 137.0, 128.9, 80.3, 80.2, 66.4, 51.9, 46.7. HR-MS (FAB): calc. 288.3, found 289.11.

3-Polymer Synthesis
Synthesis of PTDM-1

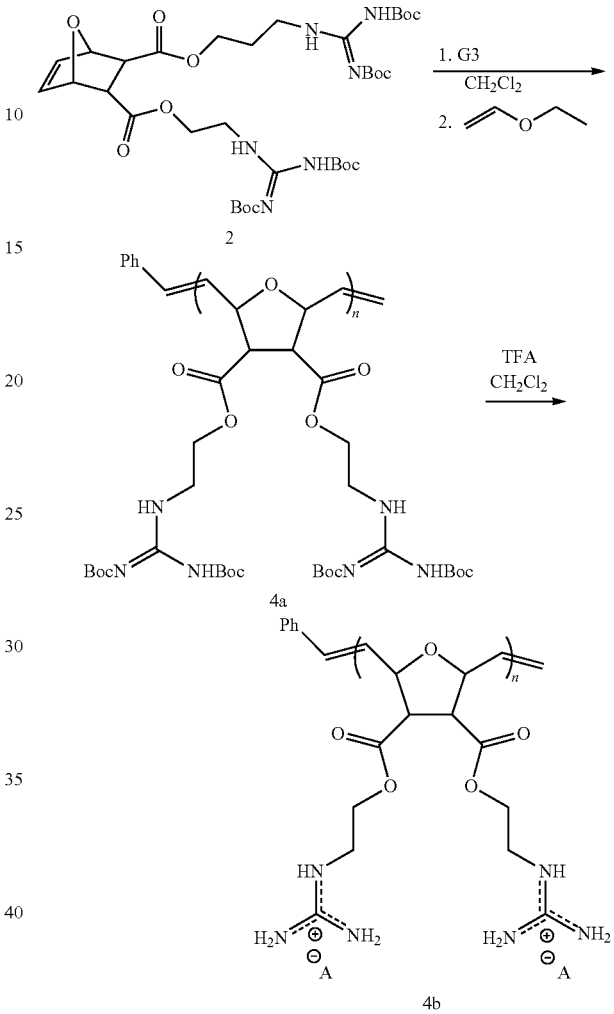

The monomer 2 and G3-catalyst were dissolved in 1 mL DCM each and subject to three freeze-thaw cycles. The monomer was added in one shot to the vigorously stirring catalyst solution at room temperature. After 60 min, the living polymer chain was end-capped with an excess of ethylvinyl ether (1 mL, 754 mg, 10.5 mmol). The solution was allowed to stir 2 h. After evaporation of the solvent, the crude product was dissolved in 1 mL THF and precipitated in pentane. The pentane solution was stirred for an additional 15 min and left standing unperturbed for an hour at 0° C. Then, the precipitate was collected by a fine sinter funnel to yield product 4a. Polymer 4a were dissolved in 2 mL DCM and 2 mL TFA for deprotection. After stirring overnight, the excess acid was removed by azeotropic distillation with methanol. After complete evaporation of the acid, samples were dissolved in water and dialyzed against RO water until the conductivity of water was ~0.1 μS. Then deprotected polymers were recovered by lyophilization. The final deprotected polymer 4b were protected from moisture and stored at 4° C.

4a: $^1$H NMR (300 MHz, CD$_3$CN): δ=11.54 (2H, br), 8.36 (2H, br), 7.33 (0.5H, br), 5.87 (trans) and 5.61 (cis) (2H total, br), 5.06 (cis) and 4.67 (trans) (2H total, br), 4.18 (4H, br), 3.56 (4H, br), 3.15 (2H, br), 1.48 (18H, s), 1.42 (18H, s).

4b: $^1$H NMR (300 MHz, CD$_3$OD): 7.34 (0.5H, br), 5.92 (trans) and 5.69 (cis) (2H total, br), 5.09 (cis) and 4.72 (trans) (2H total, br), 4.23 (4H, br), 3.48 (4H, br).

Synthesis of PTDM-2

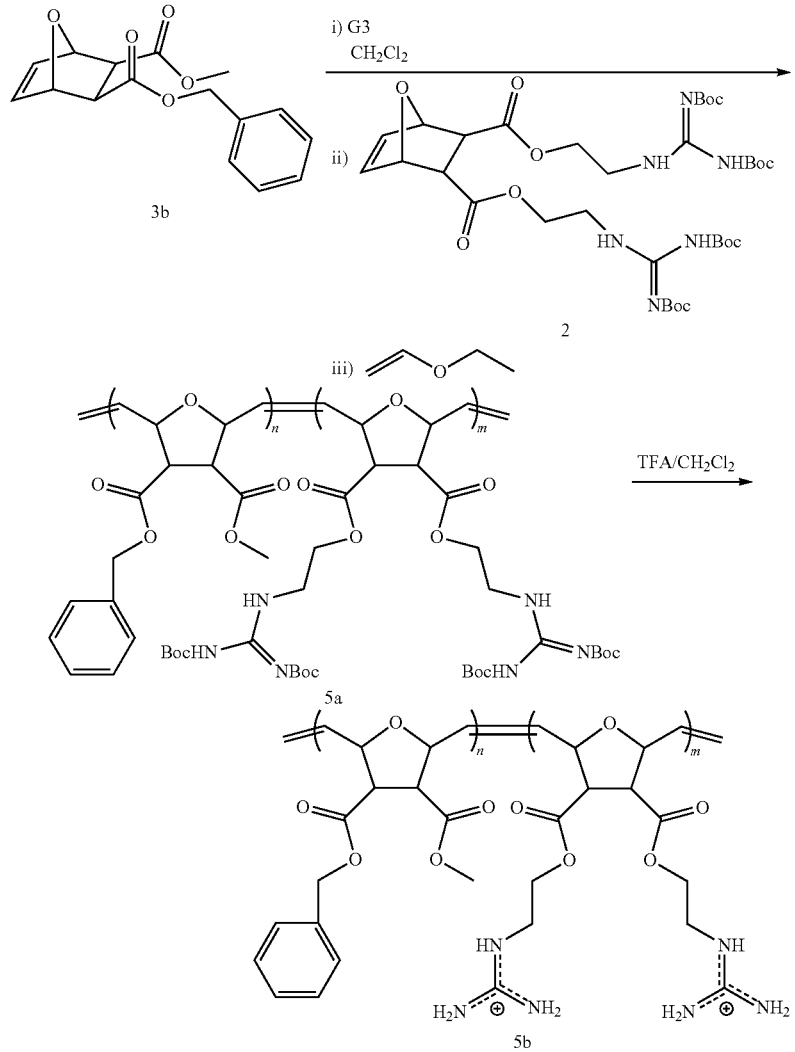

Scheme 11: Synthesis of Polymer 5b.

The monomers 2, 3b and G3-catalyst were dissolved in 1 mL DCM each and subjected to three freeze-thaw cycles. First, the monomer 3b was added in one shot to the vigorously stirring catalyst solution at room temperature. After 5 min, the monomer 2 was added in the reaction mixture as a second block and reacted for 60 min. After 60 min, the living polymer chain was end-capped with an excess of ethylvinyl ether (1 mL, 754 mg, 10.5 mmol). The solution was allowed to stir 2 h. After evaporation of the solvent, the crude product was dissolved in 1 mL THF and precipitated in pentane. The pentane solution was stirred for an additional 15 min and left standing unperturbed for an hour at 0° C. Then, the precipitate was collected by a fine sinter funnel to yield product 5a.

Polymer 5a were dissolved in 2 mL DCM and 2 mL TFA for deprotection. After stirring overnight, the excess acid was removed by azeotropic distillation with methanol. After complete evaporation of the acid, samples were dissolved in water and dialyzed against RO water until the conductivity of water was ~0.1 µS. Then deprotected polymers were recovered by lyophilization. The final deprotected polymer 5b were protected from moisture and stored at 4° C.

5a: $^1$H NMR (300 MHz, CD$_3$CN): δ=11.53 (2H, br), 8.35 (2H, br), 7.34 (6H, br), 5.86 (trans) and 5.60 (cis) (4H total, br), 5.07 (2H, br), 5.07 (cis) and 4.77 (trans) (4H total, br), 4.66 (2H, br), 4.17 (4H, br), 3.55 (4H, br), 3.48 (3H, br), 3.15 (4H, br), 1.46 (18H, s), 1.41 (18H, s).

5b: $^1$H NMR (300 MHz, CD$_3$CN): 6⁻7.09 (2H, br), 7.33 (6H, br), 7.01 (8H, br), 5.85 (trans) and 5.62 (cis) (4H total, br), 5.04 (2H, br), 5.04 (cis) and 4.64 (trans) (4H total, br), 4.12 (4H, br), 3.46 (4H, br), 3.40 (3H, br), 3.20 (4H, br).

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A composition comprising:
a polymer comprising the structural unit of Formula (IV):

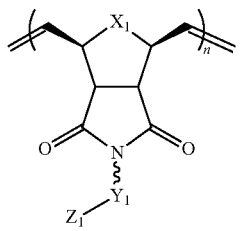

(IV)

wherein $X_1$ is O, $CH_2$ or substituted $CH_2$;

$Y_1$ is a linking group;

$Z_1$ is a group that comprises $N(R_z)_2$ or

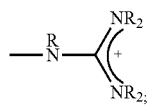

$R_z$ is hydrogen, an alkyl, substituted alkyl, aryl, or substituted aryl group;

R is hydrogen, a C1-$C_{12}$, alkyl group, or a poly(ethylene oxide); and n is independently an integer from about 2 to about 300; and a therapeutic agent having a biological effect under physiological conditions, wherein the therapeutic agent comprises an siRNA.

2. The composition of claim 1, wherein the polymer comprises the structural unit of the formula:

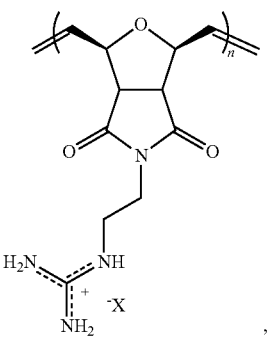

wherein $X^-$ is an anion.

3. The composition of claim 1, wherein $Y_1$ comprising a $(CH_2)_q$— group, wherein q is an integer from about 1 to about 6.

4. A composition comprising:
a polymer comprising the structural unit of Formula (IV):

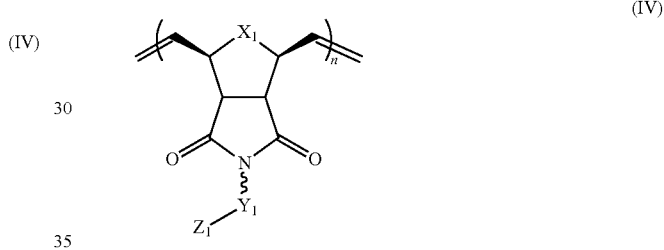

(IV)

wherein $X_1$ is O, $CH_2$ or substituted $CH_2$;

$Y_1$ is a linking group;

$Z_1$ is a group that comprises —$N(R_z)_2$ or

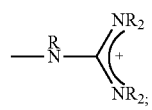

$R_z$ is hydrogen, an alkyl, substituted alkyl, aryl, or substituted aryl group;

R is hydrogen, a $C_1$-$C_{12}$ alkyl group, or a poly(ethylene oxide) group; and n is independently an integer from about 2 to about 300;

a diagnostic agent capable of emitting a detectable signal, wherein $Y_1$ comprises a carbonyl group.

5. The composition of claim 4, wherein the diagnostic agent comprises a fluorescent label.

6. The composition of claim 4, wherein the diagnostic agent comprises a radioactive label.

7. The composition of claim 4, wherein the diagnostic agent comprises a quantum dot label.

8. The composition of claim 4, wherein the polymer comprises the structural unit of the formula:

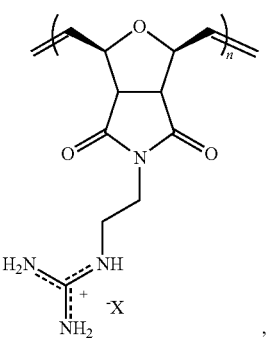

wherein X⁻ is an anion.

9. A composition comprising:
a polymer comprising the structural unit of Formula (IV):

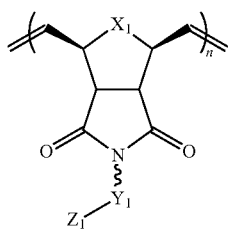

(IV)

wherein $X_1$ is $CH_2$;

$Y_1$ is a linking group;

$Z_1$ is a group that comprises $-N(R_z)_2$ or

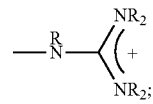

$R_z$ is hydrogen, an alkyl, substituted alkyl, aryl, or substituted aryl group;

R is hydrogen, a $C_1$-$C_{12}$ alkyl group, or a poly(ethylene oxide); and n is independently an integer from about 2 to about 300; and a therapeutic agent having a biological effect under physiological conditions.

10. The composition of claim 9, wherein the therapeutic agent comprises a peptide.

11. The composition of claim 9, wherein the therapeutic agent comprises an antibody.

12. The composition of claim 9, wherein the therapeutic agent comprises a protein.

13. The composition of claim 9, wherein the therapeutic agent comprises a nucleic acid.

* * * * *